(12) United States Patent
Komori

(10) Patent No.: US 7,902,400 B2
(45) Date of Patent: Mar. 8, 2011

(54) AMIDE COMPOUNDS AND THEIR USE

(75) Inventor: Takashi Komori, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 64 days.

(21) Appl. No.: 12/084,130

(22) PCT Filed: Oct. 20, 2006

(86) PCT No.: PCT/JP2006/321440
§ 371 (c)(1),
(2), (4) Date: Aug. 6, 2008

(87) PCT Pub. No.: WO2007/049728
PCT Pub. Date: May 3, 2007

(65) Prior Publication Data
US 2009/0131531 A1      May 21, 2009

(30) Foreign Application Priority Data
Oct. 27, 2005    (JP) ................................ 2005-312428

(51) Int. Cl.
*C07C 233/00*        (2006.01)
(52) U.S. Cl. ........................................................ 564/123
(58) Field of Classification Search ............... 564/123
See application file for complete search history.

(56) References Cited

U.S. PATENT DOCUMENTS

| | | | | |
|---|---|---|---|---|
| 6,984,648 | B2 * | 1/2006 | Lu et al. ........................ | 514/314 |
| 2010/0048701 | A1 * | 2/2010 | Komori et al. ............... | 514/543 |
| 2010/0056640 | A1 * | 3/2010 | Komori et al. ............... | 514/622 |
| 2010/0105647 | A1 * | 4/2010 | Komori et al. ............... | 514/183 |

FOREIGN PATENT DOCUMENTS

| | | |
|---|---|---|
| DE | 199 22 934 | 11/2000 |
| EP | 1 295 868 | 3/2003 |
| EP | 1295868 | * 3/2003 |

OTHER PUBLICATIONS

International Search Report issued Mar. 9, 2007 in the International (PCT) Application PCT/JP2006/321440 of which the present application is the U.S. National Stage.
Office Action issued Apr. 1, 2010 in European Patent Application No. 06 822 409.6 corresponding to present U.S. application.
International Preliminary Report on Patentability issued Apr. 29, 2008 including PCT Written Opinion in the International (PCT) Application PCT/JP2006/321440 of which the present application is the U.S. National Stage.

* cited by examiner

*Primary Examiner* — Susannah Chung
(74) *Attorney, Agent, or Firm* — Wenderoth, Lind & Ponack, L.L.P.

(57) ABSTRACT

Since an amide compound represented by the formula (1)

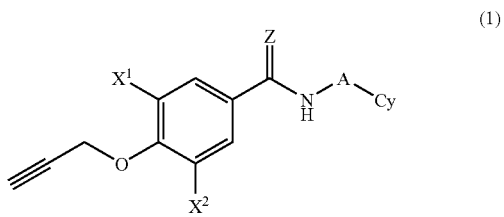

is effectiveness for controlling plant diseases, it is useful as an effective ingredient of a composition for controlling plant diseases.

17 Claims, No Drawings

AMIDE COMPOUNDS AND THEIR USE

TECHNICAL FIELD

The present invention relates to amide compounds and their use.

BACKGROUND ART

Heretofore, the development of compositions for controlling plant diseases has been carried out and many compounds which are effective for controlling plant diseases have been found. However, their activity is not always sufficient. Accordingly, there are further demands for developing novel compounds having plant disease-controlling activity.

DISCLOSURE OF INVENTION

The present invention is intended to provide a compound having superior plant disease-controlling activity.

The present inventor has intensively studied in order to find a compound having superior plant disease-controlling activity and, as a result, has found that an amide compound represented by the formula (I) has superior plant disease-controlling activity. Thus, the present invention has been completed.

That is, the present invention provides:

[1] An amide compound represented by the formula (1)

$$\text{(1)}$$

wherein $X^1$ represents a fluorine atom or a methoxy group, $X^2$ represents a hydrogen atom, a fluorine atom or a methoxy group, Z represents an oxygen atom or a sulfur atom, A represents a single bond or a $CH_2$ group, a $CH(CH_3)$ group, a $C(CH_3)_2$ group or a $CH(CH_2CH_3)$ group, Cy represents a C3 to C6 cycloalkyl group optionally substituted with at least one group selected from the group consisting of a C1 to C4 alkyl group, a C2 to C4 alkenyl group, a C2 to C4 alkynyl group, a halogen atom such as a chlorine atom, a hydroxyl group, a cyano group, a carboxyl group, or a (C1 to C3 alkoxy)carbonyl group;

[2] The amide compound according to the above [1], wherein, in the formula (1), Z is an oxygen atom;

[3] The amide compound according to the above [1] or [2], wherein, in the formula (1), $X^1$ is a fluorine atom and $X^2$ is a hydrogen atom; or $X^1$ is a fluorine atom and $X^2$ is a fluorine atom; $X^1$ is a methoxy group and $X^2$ is a hydrogen atom; or $X^1$ is a methoxy group and $X^2$ is a methoxy group;

[4] The amide compound according to the above [1] or [2], wherein, in the formula (1), $X^1$ is a methoxy group and $X^2$ is a methoxy group;

[5] The amide compound according to the above [1] or [2], wherein, in the formula (1), $X^1$ is a methoxy group and $X^2$ is a hydrogen atom;

[6] The amide compound according to any one of the above [1] to [5], wherein, in the formula (1), A is a single bond, a $CH_2$ group or a $CH(CH_3)$ group and Cy is a C3 to C6 cycloalkyl group optionally substituted with a C1 to C4 alkyl group;

[7] The amide compound according to any one of the above [1] to [5], wherein, in the formula (1), A is a single bond, a $CH_2$ group or a $CH(CH_3)$ group and Cy is a cyclohexyl group optionally substituted with a C1 to C4 alkyl group;

[8] The amide compound according to any one of the above [1] to [5], wherein, in the formula (1), A is a single bond, a $CH_2$ group or a $CH(CH_3)$ group and Cy is a cyclohexyl group optionally substituted with a methyl group;

[9] The amide compound according to the above [1], wherein in the formula (1), $X^1$ is a fluorine atom and $X^2$ is a fluorine atom;

[10] A composition for controlling plant diseases which comprises the amide compound according to any one of the above [1] to [8] as an effective ingredient and an inactive carrier;

[11] A method for controlling plant diseases which comprises a step of treating a plant or soil growing the plant with an effective amount of the amide compound according to any one of the above [1] to [8]; and

[12] Use of the amide compound according to any one of the above [1] to [8] for controlling plant diseases.

In the C3 to C6 cycloalkyl group optionally substituted with a group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group which is represented by Cy, examples of the C1 to C4 alkyl group as the substituent include a methyl group, an ethyl group, a propyl group, an isopropyl group, examples of the C2 to C4 alkenyl group as the substituent include a vinyl group, a 1-propenyl group, a 2-propenyl group, a 2-butenyl group and a 3-butenyl group, examples of the C2 to C4 alkynyl group as the substituent include an ethynyl group, a 1-propynyl group, a 2-propynyl group and a 3-butynyl group, and examples of the (C1 to C3 alkoxy)carbonyl group as the substituent include a methoxycarbonyl group and an ethoxycarbonyl group.

The C3 to C6 cycloalkyl group of the optionally substituted C3 to C6 cycloalkyl group represented by Cy is a cyclopropyl group, a cyclobutyl group, a cyclopentyl group or a cyclohexyl group.

Specific examples of the group represented by Cy-A include a cyclopropyl group, a 2,2,3,3-tetramethylcyclopropyl group, a cyclobutyl group, a cyclopentyl group, a 2-methylcyclopentyl group, a 2-hydroxycyclopentyl group, a 2-ethylcyclohexyl group, a cyclohexyl group, a 1-methylcyclohexyl group, a 2-methylcyclohexyl group, a 3-methylcyclohexyl group, a 4-methylcyclohexyl group, a 2,3-dimethylcyclohexyl group, a 2,6-dimethylcyclohexyl group, a 2,2-dimethylcyclohexyl group, a 2-hydroxycyclohexyl group, a cyclopropylmethyl group, a (1-methylcyclopropyl)methyl group, a (2-methylcyclopropyl)methyl group, a (1-hydroxycyclopropyl)methyl group, a (2-hydroxycyclopropyl)methyl group, a (2,2,3,3-tetramethylcyclopropyl)methyl group, a cyclobutylmethyl group, a (1-methylcyclobutyl)methyl group, a (2-methylcyclobutyl)methyl group, a (3-methylcyclobutyl)methyl group, a (1-hydroxycyclobutyl)methyl group, a (2-hydroxycyclobutyl)methyl group, a (3-hydroxycyclobutyl)methyl group, a cyclopentylmethyl group, a (1-methylcyclopentyl)methyl group, a (2-methylcyclopentyl)methyl group, a (3-methylcyclopentyl)methyl group, a (1-hydroxycyclopentyl)methyl group, a (2-hydroxycyclopentyl)methyl group, a (3-hydroxycyclopentyl)methyl group, a cyclohexylmethyl group, a (1-methylcyclohexyl) methyl group, a (2-methylcyclohexyl)methyl group, a (3-methylcyclohexyl)methyl group, a (4-methylcyclohexyl)methyl group, a (2,3-dimethylcyclohexyl)methyl group, a (1-hydroxycyclohexyl)methyl group, a (2-hydroxycyclohexyl) methyl group, a (3-hydroxycyclohexyl)methyl group, a (4-hydroxycyclohexyl)methyl group, a 2-chlorocyclohexyl group, a 1-(cyclopropyl)ethyl group, a 1-(cyclobutyl)ethyl group, a 1-(cyclopentyl)ethyl group, a 1-(cyclohexyl)ethyl group, a 1-(1-methylcyclohexyl)ethyl group, a 1-(1-hydroxycyclohexyl)ethyl group, a 1-methyl-1-(cyclopropyl)ethyl group, a 1-methyl-1-(cyclopropyl)ethyl group, a 1-methyl-1-(cyclobutyl)ethyl group, a 1-methyl-1-(cyclopentyl)ethyl group, a 1-methyl-1-(cyclohexyl)ethyl group and a 1-(cyclohexyl)propyl group.

As an aspect of the compounds of the present invention, for example, the following compounds are mentioned:

The amide compound represented by the formula (1), wherein Z is an oxygen atom;

The amide compound represented by the formula (1), wherein $X^1$ is a fluorine atom and $X^2$ is a hydrogen atom;

The amide compound represented by the formula (1), wherein $X^1$ is a fluorine atom and $X^2$ is a fluorine atom;

The amide compound represented by the formula (1), wherein $X^1$ is a methoxy group and X is a methoxy group;

The amide compound represented by the formula (1), wherein $X^1$ is a methoxy group and $X^2$ is a hydrogen atom;

The amide compound represented by the formula (1), wherein $X^1$ is a methoxy group and $X^2$ is a fluorine atom;

The amide compound represented by the formula (1), wherein Cy is the C5 to C6 cycloalkyl group optionally substituted with at least one group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group;

The amide compound represented by the formula (1), wherein Z is an oxygen atom and Cy is a C5 to C6 cycloalkyl group optionally substituted with at least one group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group;

The amide compound represented by the formula (1), wherein $X^1$ is a fluorine atom, $X^2$ is a hydrogen atom and Cy is a C5 to C6 cycloalkyl group be optionally substituted with at least one group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group;

The amide compound represented by the formula (1), wherein $X^1$ is a fluorine atom, $X^2$ is a fluorine atom and Cy is a C5 to C6 cycloalkyl group optionally substituted with at least one group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group;

The amide compound represented by the formula (1), wherein $X^1$ is a methoxy group, $X^2$ is a methoxy group and Cy is a C5 to C6 cycloalkyl group optionally substituted with at least one group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group;

The amide compound represented by the formula (1), wherein $X^1$ is a methoxy group and $X^2$ is a hydrogen atom and Cy is a C5 to C6 cycloalkyl group optionally substituted with at least one group selected from the group consisting of a C1 to C4 alkyl group, a C2 to C4 alkenyl group, a C2 to C4 alkynyl group, a chlorine atom, a hydroxyl group, a cyano group, a carboxyl group, or a (C1 to C3 alkoxy)carbonyl group;

The amide compound represented by the formula (1), wherein A is a single bond, a $CH_2$ group or a $CH(CH_3)$ group and Cy is a C3 to C6 cycloalkyl group optionally substituted with a C1 to C4 alkyl group;

The amide compound represented by the formula (1), wherein A is a single bond, a $CH_2$ group or a $CH(CH_3)$ group and Cy is a C5 to C6 cycloalkyl group optionally substituted with a C1 to C4 alkyl group;

The amide compound represented by the formula (1), wherein A is a single bond, a $CH_2$ group or a $CH(CH_3)$ group and Cy is a cyclohexyl group optionally substituted with a C1 to C4 alkyl group;

The amide compound represented by the formula (1), wherein A is a single bond, a $CH_2$ group or a $CH(CH_3)$ group and Cy is a cyclopentyl group optionally substituted with a C1 to C4 alkyl group;

The amide compound represented by the formula (1), wherein A is a single bond, a $CH_2$ group or a $CH(CH_3)$ group and Cy is a cyclohexyl group optionally substituted with a methyl group;

The amide compound represented by the formula (1), wherein A is a single bond, a $CH_2$ group or a $CH(CH_3)$ group and Cy is a cyclopentyl group optionally substituted with a methyl group;

The amide compound represented by the formula (1), wherein Z is an oxygen atom, A is a single bond, a $CH_2$ group or a $CH(CH_3)$ group and Cy is a C3 to C6 cycloalkyl group optionally substituted with a C1 to C4 alkyl group;

The amide compound represented by the formula (1), wherein Z is an oxygen atom, A is a single bond, a $CH_2$ group or a $CH(CH_3)$ group and Cy is a C5 to C6 cycloalkyl group optionally substituted with a C1 to C4 alkyl group;

The amide compound represented by the formula (1), wherein Z is an oxygen atom, A is a single bond, a $CH_2$ group or a $CH(CH_3)$ group and Cy is a cyclohexyl group optionally substituted with a C1 to C4 alkyl group;

The amide compound represented by the formula (1), wherein Z is an oxygen atom, A is a single bond, a $CH_2$ group or a $CH(CH_3)$ group and Cy is a cyclopentyl group optionally substituted with a C1 to C4 alkyl group;

The amide compound represented by the formula (1), wherein Z is an oxygen atom, A is a single bond, a $CH_2$ group or a $CH(CH_3)$ group and Cy is a cyclohexyl group optionally substituted with a methyl group;

The amide compound represented by the formula (1), wherein Z is an oxygen atom, A is a single bond, a $CH_2$ group or a $CH(CH_3)$ group and Cy is a cyclopentyl group optionally substituted with a methyl group;

The amide compound represented by the formula (1), wherein Z is an oxygen atom, A is a single bond and Cy is a C3 to C6 cycloalkyl group optionally substituted with a C1 to C4 alkyl group;

The amide compound represented by the formula (1), wherein Z is an oxygen atom, A is a single bond and Cy is a C5 to C6 cycloalkyl group optionally substituted with a C1 to C4 alkyl group;

The amide compound represented by the formula (1), wherein Z is an oxygen atom, A is a single bond and Cy is a cyclohexyl group optionally substituted with a C1 to C4 alkyl group;

The amide compound represented by the formula (1), wherein Z is an oxygen atom, A is a single bond and Cy is a cyclopentyl group optionally substituted with a C1 to C4 alkyl group.

The amide compound represented by the formula (1), wherein Z is an oxygen atom, A is a single bond and Cy is a cyclohexyl group optionally substituted with a methyl group;

The amide compound represented by the formula (1), wherein Z is an oxygen atom, A is a single bond and Cy is a cyclopentyl group optionally substituted with a methyl group;

The amide compound represented by the formula (1), wherein Z is an oxygen atom, A is a $CH_2$ group or a $CH(CH_3)$ group and Cy is a C3 to C6 cycloalkyl group optionally substituted with a C1 to C4 alkyl group;

The amide compound represented by the formula (1), wherein Z is an oxygen atom, A is a $CH_2$ group or a $CH(CH_3)$ group and Cy is a C5 to C6 cycloalkyl group optionally substituted with a C1 to C4 alkyl group;

The amide compound represented by the formula (1), wherein Z is an oxygen atom, A is a $CH_2$ group or a $CH(CH_3)$ group and Cy is a cyclohexyl group optionally substituted with a C1 to C4 alkyl group;

The amide compound represented by the formula (1), wherein Z is an oxygen atom, A is a $CH_2$ group or a $CH(CH_3)$ group and Cy is a cyclopentyl group optionally substituted with a C1 to C4 alkyl group;

The amide compound represented by the formula (1), wherein Z is an oxygen atom, A is a $CH_2$ group or a $CH(CH_3)$ group and Cy is a cyclohexyl group optionally substituted with a methyl group;

The amide compound represented by the formula (1), wherein Z is an oxygen atom, A is a $CH_2$ group or a $CH(CH_3)$ group and Cy is a cyclopentyl group optionally substituted with a methyl group;

The amide compound represented by the formula (1), wherein Z is an oxygen atom, A is a single bond and Cy is a cyclohexyl group.

The amide compound represented by the formula (1), wherein Z is an oxygen atom, A is a single bond and Cy is a 2-methylcyclohexyl group;

The amide compound represented by the formula (1), wherein Z is an oxygen atom, A is a single bond and Cy is a 3-methylcyclohexyl group;

The amide compound represented by the formula (1), wherein Z is an oxygen atom, A is a single bond and Cy is a 4-methylcyclohexyl group;

The amide compound represented by the formula (1), wherein Z is an oxygen atom, A is a $CH_2$ group and Cy is a cyclohexyl group;

The amide compound represented by the formula (1), wherein Z is an oxygen atom, A is a $CH_2$ group and Cy is a 1-methylcyclohexyl group;

The amide compound represented by the formula (1), wherein Z is an oxygen atom, A is a $CH_2$ group and Cy is a 2-methylcyclohexyl group;

The amide compound represented by the formula (1), wherein Z is an oxygen atom, A is a $CH_2$ group and Cy is a 3-methylcyclohexyl group;

The amide compound represented by the formula (1), wherein Z is an oxygen atom, A is a $CH_2$ group and Cy is a 4-methylcyclohexyl group;

The amide compound represented by the formula (1), wherein Z is an oxygen atom, A is a $CH(CH_3)$ group and Cy is a cyclohexyl group;

The amide compound represented by the formula (1), wherein Z is an oxygen atom, A is a $CH(CH_3)$ group and Cy is a 1-methylcyclohexyl group;

The amide compound represented by the formula (1), wherein Z is an oxygen atom, A is a $CH(CH_3)$ group and Cy is a 2-methylcyclohexyl group;

The amide compound represented by the formula (1), wherein Z is an oxygen atom, A is a $CH(CH_3)$ group and Cy is a 3-methylcyclohexyl group;

The amide compound represented by the formula (1), wherein Z is an oxygen atom, A is a $CH(CH_3)$ group and Cy is a 4-methylcyclohexyl group;

The amide compound represented by the formula (1), wherein Z is an oxygen atom, A is a single bond and Cy is a cyclopentyl group;

The amide compound represented by the formula (1), wherein Z is an oxygen atom, A is a single-bond and Cy is a 2-methylcyclopentyl group;

The amide compound represented by the formula (1), wherein Z is an oxygen atom, A is a single bond and Cy is a 3-methylcyclopentyl group;

The amide compound represented by the formula (1), wherein Z is an oxygen atom, A is a single bond and Cy is a 4-methylcyclopentyl group;

The amide compound represented by the formula (1), wherein Z is an oxygen atom, A is a $CH_2$ group and Cy is a cyclopentyl group;

The amide compound represented by the formula (1), wherein Z is an oxygen atom, A is a $CH_2$ group and Cy is a 1-methylcyclopentyl group;

The amide compound represented by the formula (1), wherein Z is an oxygen atom, A is a $CH_2$ group and Cy is a 2-methylcyclopentyl group;

The amide compound represented by the formula (1), wherein Z is an oxygen atom, A is a $CH_2$ group and Cy is a 3-methylcyclopentyl group;

The amide compound represented by the formula (1), wherein Z is an oxygen atom, A is a $CH_2$ group and Cy is a 4-methylcyclopentyl group;

The amide compound represented by the formula (1), wherein Z is an oxygen atom, A is a $CH(CH_3)$ group and Cy is a cyclopentyl group;

The amide compound represented by the formula (1), wherein Z is an oxygen atom, A is a $CH(CH_3)$ group and Cy is a 1-methylcyclopentyl group;

The amide compound represented by the formula (1), wherein Z is an oxygen atom, A is a $CH(CH_3)$ group and Cy is a 2-methylcyclopentyl group;

The amide compound represented by the formula (1), wherein Z is an oxygen atom, A is a $CH(CH_3)$ group and Cy is a 3-methylcyclopentyl group;

The amide compound represented by the formula (1), wherein Z is an oxygen atom, A is a $CH(CH_3)$ group and Cy is a 4-methylcyclopentyl group;

The amide compound represented by the formula (1), Cy is a C3 to C6 cycloalkyl group optionally substituted with a C1 to C4 alkyl group or a hydroxyl group;

The amide compound represented by the formula (1), wherein Cy is a C5 to C6 cycloalkyl group optionally substituted with a C1 to C4 alkyl group or a hydroxyl group;

The amide compound represented by the formula (1), wherein Cy is a C3 to C6 cycloalkyl group optionally substituted with a methyl group or a hydroxyl group;

The amide compound represented by the formula (1), wherein Cy is a C5 to C6 cycloalkyl group optionally substituted with a methyl group or a hydroxyl group;

The amide compound represented by the formula (1), wherein $X^1$ is a fluorine atom, $X^2$ is a hydrogen atom, Z is an oxygen atom and Cy is a C5 to C6 cycloalkyl group optionally substituted with a methyl group or a hydroxyl group;

The amide compound represented by the formula (1), wherein $X^1$ is a fluorine atom, $X^2$ is a fluorine atom, Z is an oxygen atom and Cy is a C5 to C6 cycloalkyl group optionally substituted with a methyl group or a hydroxyl group;

The amide compound represented by the formula (1), wherein $X^1$ is a methoxy group, $X^2$ is a methoxy group, Z is an oxygen atom and Cy is a C5 to C6 cycloalkyl group optionally substituted with a methyl group or a hydroxyl group; and The amide compound represented by the formula (1), wherein $X^1$ is a methoxy group, $X^2$ is a hydrogen atom, Z is an oxygen atom and Cy is a C5 to C6 cycloalkyl group optionally substituted with a methyl group or a hydroxyl group.

Hereinafter, the production process of the compound of the present invention will be illustrated.

The compound of the present invention can be produced by, for example, Production Process 1 to Production Process 7.

Production Process 1

Among the compounds of the present invention, a compound represented by the formula (5) in which Z is an oxygen atom can be produced by reacting a compound represented by the formula (2) with a compound represented by the formula (3) using a dehydration condensation agent.

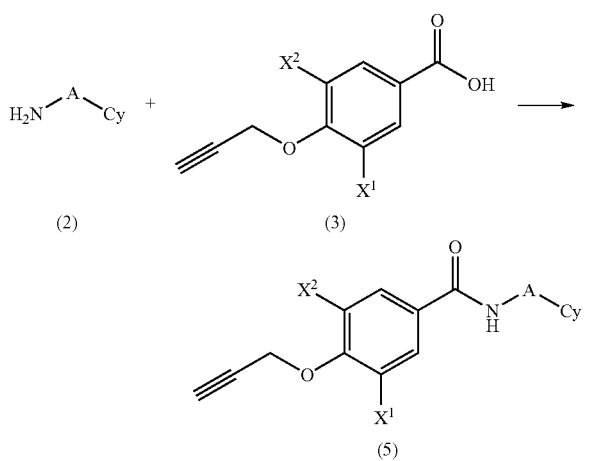

wherein $X^1$ represents a fluorine atom or a methoxy group,
$X^2$ represents a hydrogen atom, a fluorine atom or a methoxy group,
A represents a single bond, a $CH_2$ group, a $CH(CH_3)$ group, a $C(CH_3)_2$ group or a $CH(CH_2CH_3)$ group,
Cy represents a C3 to C6 cycloalkyl group optionally substituted with at least one group selected from the group consisting of a C1 to C4 alkyl group, a C2 to C4 alkenyl group, a C2 to C4 alkynyl group, a halogen atom, a hydroxyl group, a cyano group, a carboxyl group, or a (C1 to C3 alkoxy)carbonyl group.

The reaction is usually carried out in the presence of a solvent.

Examples of the solvent used for the reaction include ethers such as tetrahydrofuran (hereinafter, occasionally described as THF), ethyleneglycol dimethyl ether, tert-butyl methyl ether (hereinafter, occasionally described as MTBE), etc.; aliphatic hydrocarbons such as hexane, heptane, octane, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as N,N-dimethylformamide (hereinafter, occasionally described as DMF), etc.; sulfoxides such as dimethylsulfoxide (hereinafter, occasionally described as DMSO), etc.; and a mixture thereof.

The dehydration condensation agent used for the reaction includes carbodiimides such as 1-ethyl-3-(3-dimethylaminopropyl)carbodiimides hydrochloride (hereinafter, described as WSC), 1,3-dicyclohexylcarbodiimide, etc.

Usually, the compound represented by the formula (3) is used at a proportion of 1 to 3 mol and the dehydration condensation agent is used at a proportion of 1 to 5 mol based on 1 mol of the compound represented by the formula (2).

The reaction temperature is usually in a range of 0 to 140° C. and the reaction time is usually in a range of 1 to 24 hours.

After completion of the reaction, the compound represented by the formula (5) can be isolated by subjecting to post treatment such as filtering a reaction mixture, then extracting the filtrate with an organic solvent, and drying and concentrating the organic layer. The isolated compound represented by the formula (5) can also be further purified by chromatography, recrystallization, and the like.

Production Process 2

Among the compounds of the present invention, the compound represented by the formula (5) in which Z is an oxygen atom can be produced by reacting the compound represented by the formula (2) with the compound represented by the formula (4) in the presence of a base.

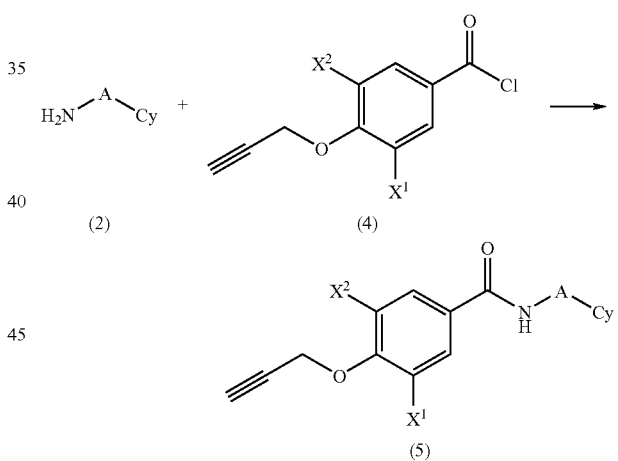

wherein A, Cy, $X^1$ and $X^2$ are as defined above.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as DMF, etc.; sulfoxides such as DMSO, etc.; and a mixture thereof.

The base used for the reaction includes alkali metal carbonates such as sodium carbonate, potassium carbonate, etc.; tertiary amines such as triethylamine, diisopropylethylamine, etc.; nitrogen-containing aromatic compounds such as pyridine, 4-dimethylaminopyridine, etc.; and the like.

Usually, the compound represented by the formula (4) is used at a proportion of 1 to 3 mol and the base is used at a proportion of 1 to 10 mol based on 1 mol of the compound represented by the formula (2).

The reaction temperature is usually in a range of −20 to 100° C. and the reaction time is usually in a range of 0.1 to 24 hours.

After completion of the reaction, the compound represented by the formula (5) can be isolated by subjecting to post treatment such as extracting a reaction mixture with an organic solvent and drying and concentrating the organic layer. The isolated compound represented by the formula (5) can also be further purified by chromatography, recrystallization, and the like.

Production Process 3

Among the compounds of the present invention, a compound represented by the formula (6) in which Z is a sulfur atom can be produced by reacting the compound represented by the formula (5) in which Z is an oxygen atom with 2,4-bis(4-methoxyphenyl)-1,3-dithia-2,4-diphosphetan-2,4-disulfide (hereinafter, described as Lawesson's Reagent).

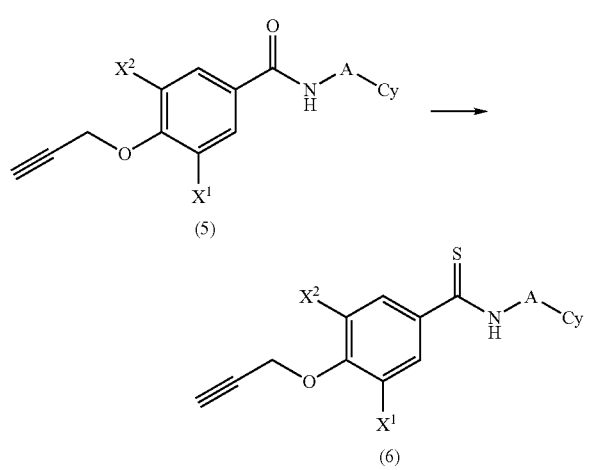

wherein A, Cy, $X^1$ and $X^2$ are as defined above.

The reaction is usually carried out in the presence of a solvent.

Examples of the solvent used for the reaction include ethers such as THF, ethyleneglycol dimethyl ether, MTBE. etc.; aliphatic hydrocarbons such as hexane, heptane, octane, etc.; aromatic hydrocarbons such as toluene, xylene, etc.; halogenated hydrocarbons such as chlorobenzene, etc.; organic nitriles such as acetonitrile, butyronitrile, etc.; sulfoxides such as dimethylsulfoxide, etc.; and a mixture thereof.

Usually, the Lawesson's Reagent is used at a proportion of 1 to 2 mol based on 1 mol of the compound represented by the formula (5).

The reaction temperature is usually in a range of 25 to 150° C. and the reaction time is usually in a range of 0.1 to 24 hours.

After completion of the reaction, the compound represented by the formula (6) can be isolated by subjecting to post treatment such as extracting a reaction mixture with an organic solvent and drying and concentrating the organic layer. The isolated compound represented by the formula (6) can also be further purified by chromatography, recrystallization, and the like.

Production Process 4

Among the compounds of the present invention, a compound represented by the formula (8) in which $X^1$ and $X^2$ are fluorine atoms can be produced according to the following scheme.

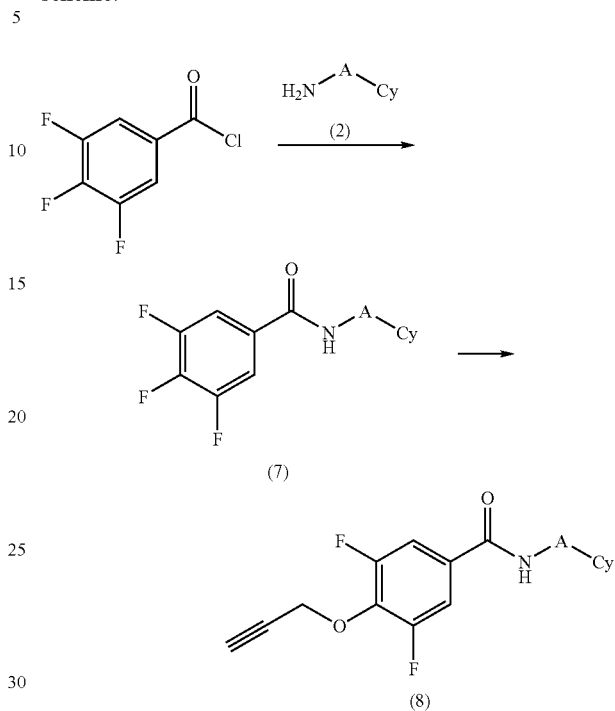

wherein A and Cy are as defined above.

The compound represented by the formula (7) can be produced by reacting 3,4,5-trifluorobenzoyl chloride with the compound represented by the formula (2) in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; tertiary amines such as triethylamine, diisopropylethylamine, etc.; nitrogen-containing aromatic compounds such as pyridine, 4-dimethylaminopyridine, etc.; and the like.

Usually, 3,4,5-trifluorobenzoyl chloride is used at a proportion of 1 to 3 mol and the base is used at a proportion of 1 to 10 mol based on 1 mol of the compound represented by the formula (2).

The reaction temperature is usually in a range of −20 to 100° C. and the reaction time is usually in a range of 0.1 to 24 hours.

After completion of the reaction, the compound represented by the formula (7) can be isolated by subjecting to post treatment such as extracting a reaction mixture with an organic solvent and drying and concentrating the organic layer. The isolated compound represented by the formula (7) can also be further purified by chromatography, recrystallization, and the like.

The compound represented by the formula (8) can be produced by reacting the compound represented by the formula (7) with propargyl alcohol in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; ketones such as acetone, methyl ethyl ketone, methyl isobutyl ketone, etc.; aromatic hydrocarbons such as toluene, xylene, etc.; halogenated hydrocarbons such as chlorobenzene, etc.; esters such as butyl acetate, ethyl acetate, etc.; nitriles such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; alkali metal bicarbonates such as sodium bicarbonate, etc.; alkali metal hydrides such as sodium hydride, etc.; alkali metal hydroxides such as sodium hydroxide, etc.; and the like.

Usually, propargyl alcohol is used at a proportion of 1 to 3 mol and the base is used at a proportion of 1 to 2 mol based on 1 mol of the compound represented by the formula (7).

The reaction temperature is usually in a range of −20 to 100° C. and the reaction time is usually in a range of 0.1 to 24 hours.

After completion of the reaction, the compound represented by the formula (8) can be isolated by subjecting to post treatment such as extracting a reaction mixture with an organic solvent and drying and concentrating the organic layer. The isolated compound represented by the formula (8) can also be further purified by chromatography, recrystallization, and the like.

Production Process 5

Among the compounds of the present invention, the compound represented by the formula (5) in which Z is an oxygen atom can be produced by reacting a compound represented by the formula (9) with propargyl bromide in the presence of a base.

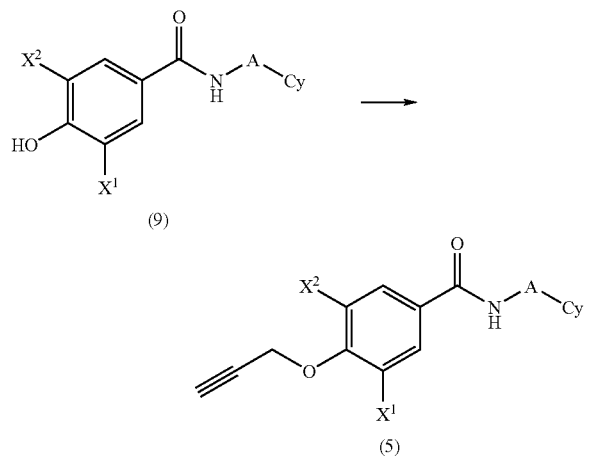

wherein A, Cy, $X^1$ and $X^2$ are as defined above.

The reaction is usually carried out in the presence of a solvent.

Examples of the solvent used for the reaction include ethers such as THF, ethyleneglycol dimethyl ether, tert-butyl methyl ether, etc.; aromatic hydrocarbons such as toluene, xylene, etc.; halogenated hydrocarbons such as chlorobenzene, etc.; nitriles such as acetonitrile, etc.; acid amides such as DMF, etc.; sulfoxides such as dimethylsulfoxide, etc.; water; and a mixture thereof.

The base used for the reaction includes alkali metal carbonates such as sodium carbonate, potassium carbonate, cesium carbonate, etc.; alkali metal hydroxides such as sodium hydroxide, etc.; alkali metal hydrides such as sodium hydride, etc.; and the like.

Usually, propargyl bromide is used at a proportion of 1 to 3 mol and the base is used at a proportion of 1 to 3 mol based on 1 mol of the compound represented by the formula (9).

The reaction temperature is usually in a range of −20 to 100° C. and the reaction time is usually in a range of 0.1 to 24 hours.

After completion of the reaction, the compound represented by the formula (5) can be isolated by subjecting to post treatment such as extracting a reaction mixture with an organic solvent and drying and concentrating the organic layer. The isolated compound represented by the formula (5) can also be further purified by chromatography, recrystallization, and the like.

Production Process 6

Among the compounds of the present invention, a compound represented by the formula (11) in which $X^1$ is a fluorine atom and $X^2$ is a hydrogen atom can be produced according to the following scheme.

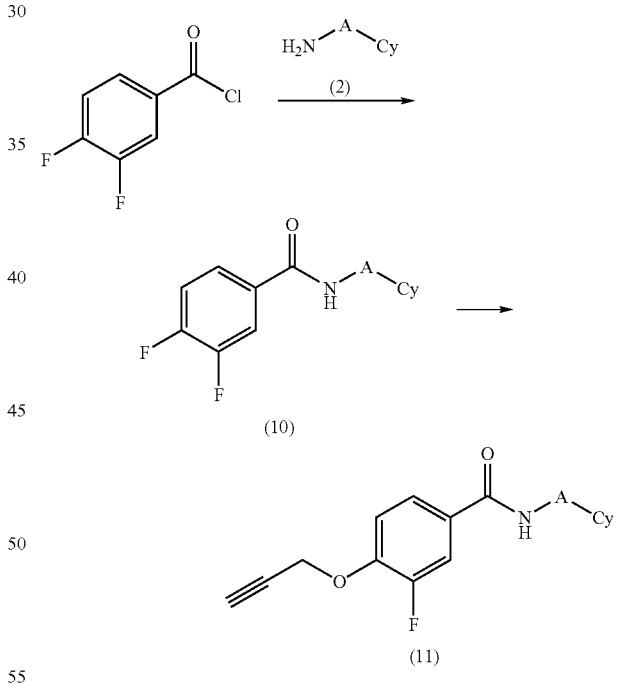

wherein A and Cy are as defined above.

The compound represented by the formula (10) can be produced by reacting 3,4-difluorobenzoyl chloride with the compound represented by the formula (2) in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.;

aromatic hydrocarbons such as toluene, xylene, etc.; halogenated hydrocarbons such as chlorobenzene, etc.; esters such as butyl acetate, ethyl acetate, etc.; nitriles such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; tertiary amines such as triethylamine, diisopropylethylamine, etc.; nitrogen-containing aromatic compounds such as pyridine, 4-dimethylaminopyridine, etc.; and the like.

Usually, 3,4-difluorobenzoyl chloride is used at a proportion of 1 to 3 mol and the base is used at a proportion of 1 to 10 mol based on 1 mol of the compound represented by the formula (2).

The reaction temperature is usually in a range of −20 to 100° C. and the reaction time is usually in a range of 0.1 to 24 hours.

After completion of the reaction, the compound represented by the formula (10) can be isolated by subjecting to post treatment such as extracting a reaction mixture with an organic solvent and drying and concentrating the organic layer. The isolated compound represented by the formula (10) can also be further purified by chromatography, recrystallization, and the like.

The compound represented by the formula (11) can be produced by reacting the compound represented by the formula (10) with propargyl alcohol in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; ketones such as acetone, methyl ethyl ketone, methyl isobutyl ketone, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; alkali metal bicarbonates such as sodium bicarbonate, etc.; alkali metal hydrides such as sodium hydride, etc.; alkali metal hydroxides such as sodium hydroxide, etc.; and the like.

Usually, propargyl alcohol is used at a proportion of 1 to 3 mol and the base is used at a proportion of 1 to 2 mol based on 1 mol of the compound represented by the formula (10).

The reaction temperature is usually in a range of −20 to 100° C. and the reaction time is usually in a range of 0.1 to 24 hours.

After completion of the reaction, the compound represented by the formula (11) can be isolated by subjecting to post treatment such as extracting a reaction mixture with an organic solvent and drying and concentrating the organic layer. The isolated compound represented by the formula (11) can also be further purified by chromatography, recrystallization, and the like.

Production Process 7

Among the compounds of the present invention, a compound represented by the formula (13) can be produced according to a method shown in the following scheme.

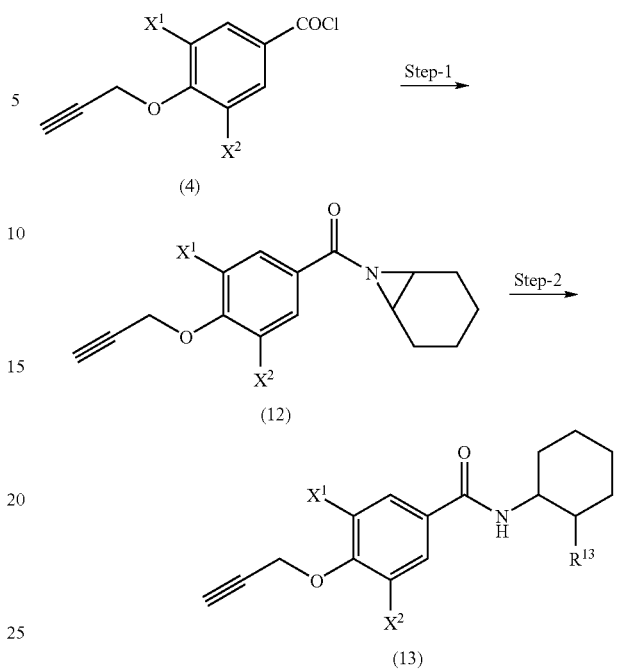

wherein $X^1$ and $X^2$ are as defined above, and $R^{13}$ represents a halogen atom or a cyano group.

Step-1

The compound represented by the formula (12) can be produced from the compound represented by the formula (4) and 7-azabicyclo[4.1.0]heptane according to the method described in Production Process 2.

Step-2

The compound represented by the formula (13) can be produced by reacting the compound represented by the formula (12) and a source of a nucleophile represented by $(R^{13})^-$.

The reaction is usually performed in the presence of a solvent.

Examples of the solvent used in the reaction include ethers such as THF, ethylene glycol dimethyl ether, MTBE, etc.; aromatic hydrocarbons such as toluene, xylene, etc.; halogenated hydrocarbons such as chlorobenzene, chloroform, etc.; esters such as butyl acetate, ethyl acetate, etc.; nitrites such as acetonitrile, etc.; acid amides such as DMF, etc.; and a mixture thereof.

Examples of the source of a nucleophile represented by $(R^{13})^-$ used in the reaction include potassium fluoride, tetrabutylammonium fluoride, sodium chloride, zinc (II) chloride, sodium bromide, zinc(II) bromide, potassium iodide, zinc (II) iodide, potassium cyanide, trimethylsilyl cyanide, and the like, and the source can be appropriately selected depending on a kind of $R^{13}$.

The source of a nucleophile represented by $(R^{13})^-$ is usually used at a proportion of 1 to 10 mol based on 1 mol of the compound represented by the formula (12).

The reaction temperature is usually in a range of −20 to 150° C., and the reaction time is usually in a range of 0.1 to 24 hours.

After completion of the reaction, the compound represented by the formula (13) can be isolated by subjecting to a post-treatment procedure such as by pouring the reaction mixture into water, extracting this with an organic solvent, and drying and concentrating the organic layer, etc. The isolated compound represented by the formula (13) may be further purified by chromatography, recrystallization, or the like.

An intermediate used for the production of the compound of the present invention can be produced by, for example, the following Intermediate Production Process 1 to Intermediate Production Process 7.

Intermediate Production Process 1

The compound represented by the formula (3) and the compound represented by the formula (4) can be produced according to the following scheme.

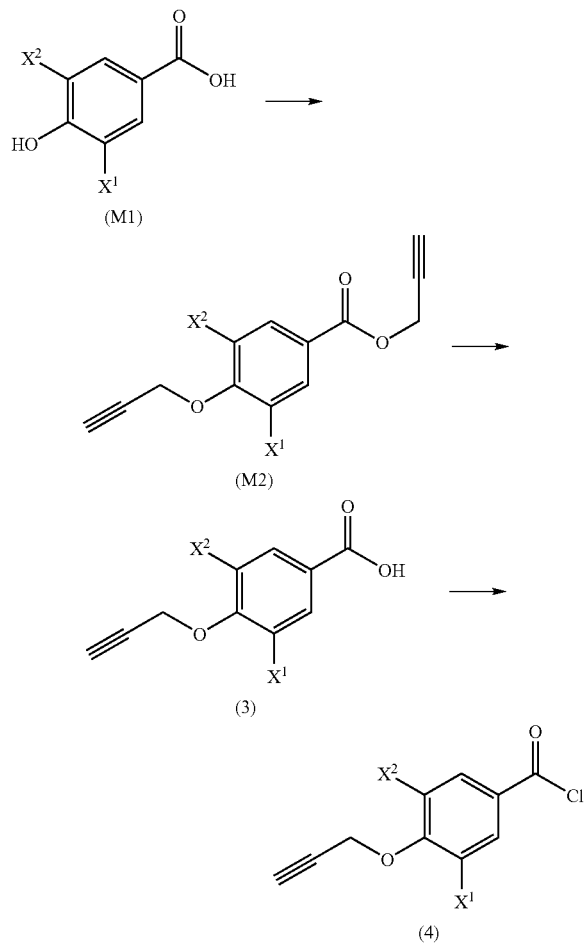

wherein $X^1$ and $X^2$ are as defined above.

The compound represented by the formula (M2) can be produced by reacting the compound represented by the formula (M1) with propargyl bromide in the presence of a base.

The reaction is usually carried out in the presence of a solvent.

Examples of the solvent used for the reaction include acid amides such as DMF, etc.; sulfoxides such as DMSO, etc.

The base used for the reaction includes alkali metal carbonates such as sodium carbonate, potassium carbonate, cesium carbonate, etc.; alkali metal hydroxides such as sodium hydroxide, etc.; and the like.

Usually, propargyl bromide is used at a proportion of 2 to 5 mol and the base is used at a proportion of 2 to 5 mol based on 1 mol of the compound represented by the formula (M1).

The reaction temperature is usually in a range of 0 to 140° C. and the reaction time is usually in a range of 0.5 to 24 hours.

After completion of the reaction, the compound represented by the formula (M2) can be isolated by subjecting to post treatment such as extracting a reaction mixture with an organic solvent and drying and concentrating the organic layer. The isolated compound represented by the formula (M2) can also be further purified by chromatography, recrystallization, and the like.

The compound represented by the formula (3) can be produced by hydrolyzing the compound represented by the formula (M2) in the presence of a base.

The reaction is usually carried out in the presence of a solvent.

The base used for the reaction includes alkali metal hydroxides such as sodium hydroxide, potassium hydroxide, etc.; and the like.

Examples of the solvent used for the reaction include ethers such as tetrahydrofuran, ethyleneglycol dimethyl ether, tert-butyl methyl ether, etc.; alcohols such as methanol, ethanol, etc.; and a mixture thereof.

Water is used at a proportion of 1 mol to an excess amount and the base is usually used at a proportion of 1 to 10 mol based on 1 mol of the compound represented by the formula (M2).

The reaction temperature is usually in a range of 0 to 120° C. and the reaction time is usually in a range of 0.5 to 24 hours.

After completion of the reaction, the compound represented by the formula (3) can be isolated by subjecting to post treatment such as acidifying a reaction mixture, then extracting it with an organic solvent and drying and concentrating the organic layer. The isolated compound represented by the formula (3) can also be further purified by chromatography, recrystallization, and the like.

The compound represented by the formula (4) can be produced by reacting the compound represented by the formula (3) with thionyl chloride.

The reaction is usually carried out in the presence of a solvent.

Examples of the solvent used for the reaction include aliphatic hydrocarbons such as hexane, heptane, octane, etc.; aromatic hydrocarbons such as toluene, xylene, etc.; halogenated hydrocarbons such as chlorobenzene, etc.; acid amides such as DMF, etc.; and a mixture thereof.

Thionyl chloride is usually used at a proportion of 1 to 2 mol based on 1 mol of the compound represented by the formula (3).

The reaction temperature is usually in a range of 20 to 120° C. and the reaction time is usually in a range of 0.1 to 24 hours.

After completion of the reaction, the compound represented by the formula (4) can be isolated by concentrating a reaction mixture as it is.

Intermediate Production Process 2

The compound represented by the formula (9) can be produced according to the following scheme.

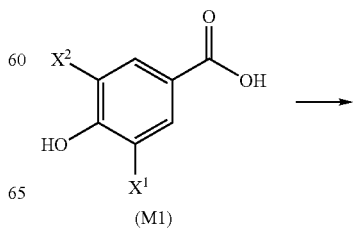

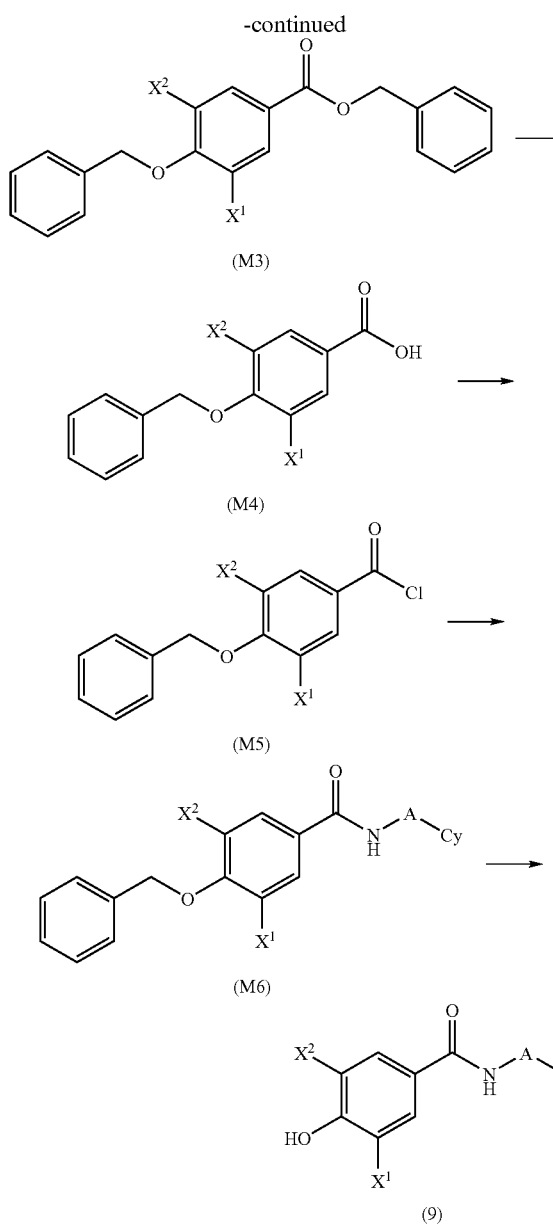

(M3)

(M4)

(M5)

(M6)

(9)

wherein A, Cy, $X^1$ and $X^2$ are as defined above.

The compound represented by the formula (M3) can be produced by reacting the compound represented by the formula (M1) with benzyl bromide in the presence of a base.

The reaction is usually carried out in the presence of a solvent.

Examples of the solvent used for the reaction include acid amides such as DMF, etc.; sulfoxides such as DMSO, etc.

Examples of the base used for the reaction include alkali metal carbonates such as sodium carbonate, potassium carbonate, cesium carbonate, etc.; alkali metal hydroxides such as sodium hydroxide, etc.; and the like.

Usually, benzyl bromide is used at a proportion of 2 to 5 mol and the base is used at a proportion of 2 to 5 mol based on 1 mol of the compound represented by the formula (Ml).

The reaction temperature is usually in a range of 0 to 140° C. and the reaction time is usually in a range of 0.5 to 24 hours.

After completion of the reaction, the compound represented by the formula (M3) can be isolated by subjecting to post treatment such as extracting a reaction mixture with an organic solvent and drying and concentrating the organic layer. The isolated compound represented by the formula (M3) can also be further purified by chromatography, recrystallization, and the like.

The compound represented by the formula (M4) can be produced by hydrolyzing the compound represented by the formula (M3) in the presence of a base.

The reaction is usually carried out in the presence of a solvent.

Examples of the base used for the reaction include alkali metal hydroxides such as sodium hydroxide, potassium hydroxide, etc.; and the like.

Examples of the solvent used for the reaction include ethers such as tetrahydrofuran, ethyleneglycol dimethyl ether, tert-butyl methyl ether, etc.; alcohols such as methanol, ethanol, etc.; and a mixture thereof.

Water is used at a proportion of 1 mol to an excessive amount and the base is usually used at a proportion of 1 to 10 mol based on 1 mol of the compound represented by the formula (M3).

The reaction temperature is usually in a range of 0 to 120° C. and the reaction time is usually in a range of 0.5 to 24 hours.

After completion of the reaction, the compound represented by the formula (M4) can be isolated by subjecting to post treatment such as acidifying a reaction mixture, then extracting it with an organic solvent and drying and concentrating the organic layer. The isolated compound represented by the formula (M4) can also be further purified by chromatography, recrystallization, and the like.

The compound represented by the formula (M5) can be produced by reacting the compound represented by the formula (M4) with thionyl chloride.

The reaction is usually carried out in the presence of a solvent.

Examples of the solvent used for the reaction include aliphatic hydrocarbons such as hexane, heptane, octane, etc.; aromatic hydrocarbons such as toluene, xylene, etc.; halogenated hydrocarbons such as chlorobenzene, etc.; acid amides such as DMF, etc.; and a mixture thereof.

Thionyl chloride is usually used at a proportion of 1 to 2 mol based on 1 mol of the compound represented by the formula (M4).

The reaction temperature is usually in a range of 20 to 120° C. and the reaction time is usually in a range of 0.1 to 24 hours.

After completion of the reaction, the compound represented by the formula (M5) can be isolated by concentrating a reaction mixture as it is.

The compound represented by the formula (M6) can be produced by reacting the compound represented by the formula (M5) with the compound represented by the formula (2) in the presence of a base according to the method described in Production Process 2.

The compound represented by the formula (9) can be produced by reacting the compound represented by the formula (M6) with hydrogen in the presence of palladium-carbon.

The reaction is usually carried out in the presence of a solvent.

Examples of the solvent used for the reaction include aliphatic hydrocarbons such as hexane, heptane, octane, etc.; aromatic hydrocarbons such as toluene, xylene, etc.; alcohols such as methanol, ethanol, etc.; esters such as ethyl acetate, etc.; ethers such as THF, MTBE, etc.; water; and a mixture thereof.

Usually, palladium carbon is used at a proportion of 0.01 to 0.1 mol and hydrogen is used at a proportion of 1 to 2 mol based on 1 mol of the compound represented by the formula (M6).

The reaction temperature is usually in a range of 0 to 50° C. and the reaction time is usually in a range of 0.1 to 24 hours.

After completion of the reaction, the compound represented by the formula (9) can be isolated by subjecting to post treatment such as filtering a reaction mixture, extracting it with an organic solvent and drying and concentrating the organic layer. The isolated compound represented by the formula (9) can also be further purified by chromatography, recrystallization, and the like.

Among the compounds represented by the formula (3), the compound in which $X^1$ and $X^2$ are a fluorine atom, i.e., 3,5-difluoro-4-(2-propynyloxy)benzoic acid, can be produced by the process described in Intermediate Production Process 3 or Intermediate Production Process 4 from 3,4,5-trifluorobenzaldehyde.

Intermediate Production Process 3

3,5-Difluoro-4-(2-propynyloxy)benzoic acid can be produced according to the following scheme.

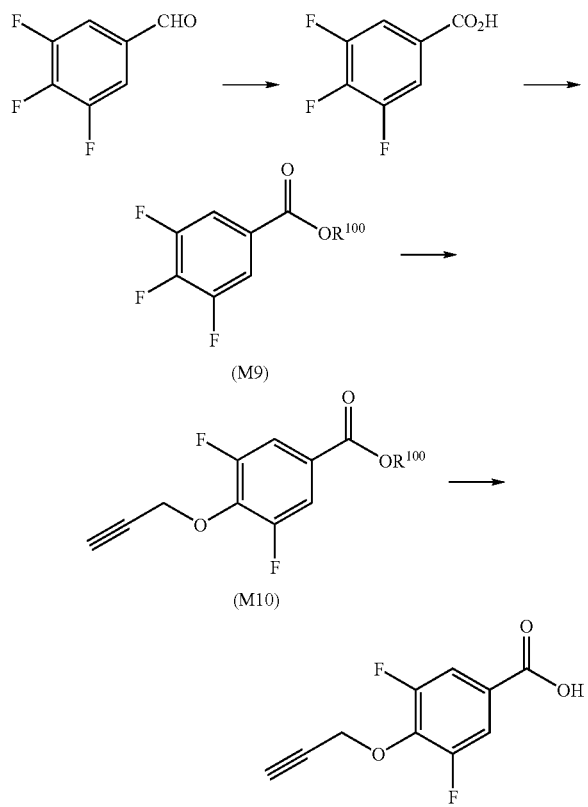

wherein $R^{100}$ represents a C1-C4 alkyl group, a 2-propynyl group or a benzyl group.

3,4,5-Trifluorobenzoic acid can be produced by reacting 3,4,5-trifluorobenzaldehyde with an oxidizing agent.

The reaction is usually carried out in the presence of a solvent.

Examples of the solvent used for the reaction include ketones such as acetone, isobutyl ketone, etc.; nitriles such as acetonitrile, etc.; acid amides such as DMF, etc.; halogenated hydrocarbons such as chloroform, etc.; water; and a mixture thereof.

Examples of the oxidizing agent used for the reaction include potassium permanganate, 3-chloroperbenzoic acid and potassium peroxymono sulfate.

The oxidizing agent is usually used at a proportion of 1 to 5 mol based on 1 mol of 3,4,5-trifluorobenzaldehyde.

The reaction temperature is usually in a range of 0 to 100° C. and the reaction time is usually in a range of 0.5 to 24 hours.

After completion of the reaction, 3,4,5-trifluorobenzoic acid can be isolated by subjecting to post treatment such as extracting a reaction mixture with an organic solvent and drying and concentrating the organic layer. The isolated 3,4,5-trifluorobenzoic acid can also be further purified by chromatography, recrystallization, and the like.

The compound represented by the formula (M9) can be produced by reacting 3,4,5-trifluorobenzoic acid with $R^{100}$-$L^1$ [wherein $L^1$ represents a chlorine atom, a bromine atom, an iodine atom or a methanesulfonyloxy group] in the presence of a base.

The reaction is usually carried out in the presence of a solvent.

Examples of the solvent used for the reaction include nitrites such as acetonitrile, etc.; acid amides such as DMF, etc.; sulfoxides such as DMSO, etc.; water; and a mixture thereof.

Examples of the base used for the reaction include alkali metal carbonates such as sodium carbonate, potassium carbonate, cesium carbonate, etc.; alkali metal hydroxides such as sodium hydroxide, etc.; and the like.

Usually, the compound represented by $R^{100}$-$L^1$ is used at a proportion of 1 to 5 mol and the base is used at a proportion of 1 to 5 mol based on 1 mol of 3,4,5-trifluorobenzoic acid.

The reaction temperature is usually in a range of 0 to 140° C. and the reaction time is usually in a range of 0.5 to 24 hours.

After completion of the reaction, the compound represented by the formula (M9) can be isolated by subjecting to post treatment such as extracting a reaction mixture with an organic solvent and drying and concentrating the organic layer. The isolated compound represented by the formula (M9) can also be further purified by chromatography, recrystallization, and the like.

The compound represented by the formula (M10) can be produced by reacting the compound represented by the formula (M9) with propargyl alcohol in the presence of a base.

The reaction is usually carried out in the presence of a solvent.

Examples of the solvent used for the reaction include nitrites such as acetonitrile, etc.; acid amides such as DMF, etc.; sulfoxides such as DMSO, etc.

The base used for the reaction includes alkali metal carbonates such as sodium carbonate, potassium carbonate, cesium carbonate, etc.; alkali metal hydroxides such as sodium hydroxide, etc.; alkali metal hydrides such as sodium hydride, etc.; and the like.

Usually, propargyl alcohol is used at a proportion of 1 to 5 mol and the base is used at a proportion of 1 to 5 mol based on 1 mol of the compound represented by the formula (M9).

The reaction temperature is usually in a range of 0 to 140° C. and the reaction time is usually in a range of 0.5 to 24 hours.

After completion of the reaction, the compound represented by the formula (M10) can be isolated by subjecting to post treatment such as extracting a reaction mixture with an organic solvent and drying and concentrating the organic layer. The isolated compound represented by the formula (M10) can also be further purified by chromatography, recrystallization, and the like.

3,5-Difluoro-4-(2-propynyloxy)benzoic acid can be produced by hydrolyzing the compound represented by the formula (M10) in the presence of a base.

The reaction is usually carried out in the presence of a solvent.

Examples of the base used for the reaction include alkali metal hydroxides such as sodium hydroxide, potassium hydroxide, etc.; and the like.

Examples of the solvent used for the reaction include ethers such as tetrahydrofuran, ethyleneglycol dimethyl ether, tert-butyl methyl ether, etc.; alcohols such as methanol, ethanol, etc.; and a mixture thereof.

Usually, water is used at a proportion of 1 mol to an excessive amount and the base is used at a proportion of 1 to 10 mol based on 1 mol of the compound represented by the formula (M10).

The reaction temperature is usually in a range of 0 to 120° C. and the reaction time is usually in a range of 0.5 to 24 hours.

After completion of the reaction, 3,5-difluoro-4-(2-propynyloxy)benzoic acid can be isolated by subjecting to post treatment such as acidifying a reaction mixture, then extracting it with an organic solvent and drying and concentrating the organic layer. The isolated 3,5-difluoro-4-(2-propynyloxy)benzoic acid can also be further purified by chromatography, recrystallization, and the like.

Intermediate Production Process 4

3,5-Difluoro-4-(2-propynyloxy)benzoic acid can be produced according to the following scheme.

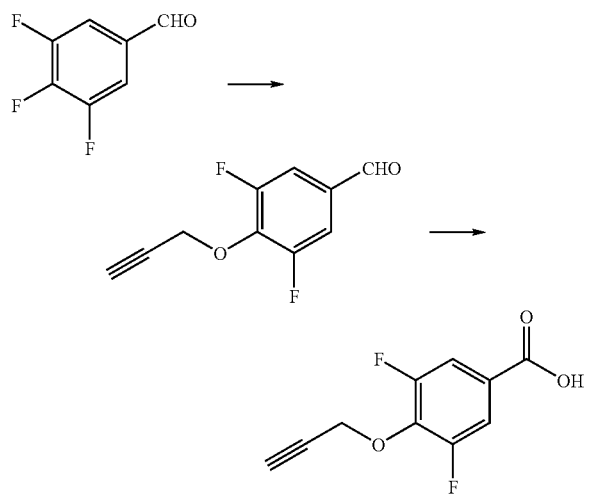

3,5-Difluoro-4-(2-propynyloxy)benzaldehyde can be produced by reacting 3,4,5-trifluorobenzaldehyde with propargyl alcohol in the presence of a base.

The reaction is usually carried out in the presence of a solvent.

Examples of the solvent used for the reaction include hydrocarbons such as toluene, etc.; nitrites such as acetonitrile, etc.; acid amides such as DMF, etc.; sulfoxides such as DMSO, etc.; ketones such as acetone, methyl isobutyl ketone, etc.; water; and a mixture thereof.

The base used for the reaction include alkali metal carbonates such as sodium carbonate, potassium carbonate, cesium carbonate, etc.; alkali metal hydroxides such as sodium hydroxide, etc.; alkali metal hydrides such as sodium hydride, etc.; and the like.

Usually, propargyl alcohol is used at a proportion of 1 to 5 mol and the base is used at a proportion of 1 to 5 mol based on 1 mol of 3,4,5-trifluorobenzaldehyde.

The reaction temperature is usually in a range of 0 to 100° C. and the reaction time is usually in a range of 0.5 to 24 hours.

After completion of the reaction, 3,5-difluoro-4-(2-propynyloxy)benzaldehyde can be isolated by subjecting to post treatment such as extracting a reaction mixture with an organic solvent and drying and concentrating the organic layer. The isolated 3,5-difluoro-4-(2-propynyloxy)benzaldehyde can also be further purified by chromatography, recrystallization, and the like.

3,5-Difluoro-4-(2-propynyloxy)benzoic acid can be produced by reacting 3,5-difluoro-4-(2-propynyloxy)benzaldehyde with an oxidizing agent.

The reaction is usually carried out in the presence of a solvent.

Examples of the solvent used for the reaction include ketones such as acetone, isobutyl ketone, etc.; nitrites such as acetonitrile, etc.; acid amides such as DMF, etc.; halogenated hydrocarbons such as chloroform, etc.; water and a mixture thereof.

Examples of the oxidizing agent used for the reaction include potassium permanganate, 3-chloroperbenzoic acid and potassium peroxymono sulfate.

The oxidizing agent is usually used at a proportion of 1 to 5 mol based on 1 mol of 3,5-difluoro-4-(2-propynyloxy)benzaldehyde.

The reaction temperature is usually in a range of 0 to 100° C. and the reaction time is usually in a range of 0.5 to 24 hours.

After completion of the reaction, 3,5-difluoro-4-(2-propynyloxy)benzoic acid can be isolated by subjecting to post treatment such as extracting a reaction mixture with an organic solvent and drying and concentrating the organic layer to post treatment operations such as drying and concentration. The isolated 3,5-difluoro-4-(2-propynyloxy)benzoic acid can also be further purified by chromatography, recrystallization, and the like.

Intermediate Production Process 6

Among the compounds represented by the formula (2), the compound in which A is a $CH_2$ group can be produced by reacting the compound represented by the formula $Cy$-$CONH_2$ (wherein Cy is as defined above) or the compound represented by the formula Cy-CN (wherein Cy is as defined above) with a reducing agent (for example, lithium aluminum hydride).

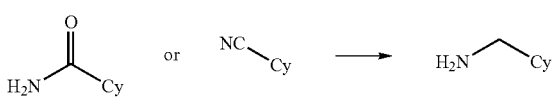

wherein Cy is as defined above.

The reaction is usually carried out in the presence of a solvent.

Examples of the solvent used for the reaction include ethers such as THF, ethyleneglycol dimethyl ether, MTBE, and the like.

Usually, the reducing agent is used at a proportion of 1 to 3 mol based on 1 mol of the starting compound.

The reaction temperature is usually in a range of −20 to 100° C. and the reaction time is usually in a range of 0.1 to 24 hours.

After completion of the reaction, the objective compound can be isolated by subjecting to post treatment such as extracting a reaction mixture with an organic solvent and drying and concentrating the organic layer. The objective compound isolated can also be further purified by chromatography, recrystallization, and the like.

Intermediate Production Process 7

Among the compounds represented by the formula (2), the compound in which A is a $CH(CH_3)$ group can be produced by reacting the compound represented by the formula Cy-$COCH_3$ (wherein Cy is as defined above) with ammonium formate in the presence of a transition metal catalyst (for example, palladium carbon).

wherein Cy is as defined above.

The reaction is usually carried out in the presence of a solvent.

Example of the solvent used for the reaction include ethers such as THF, ethyleneglycol dimethyl ether, MTBE, etc.; alcohols such as methanol, ethanol, etc.; esters such as ethyl acetate, etc.; water and the like.

Usually, ammonium formate is used at a proportion of 1 to 10 mol and the catalyst is used at a proportion of 0.001 to 0.1 mol based on 1 mol of the starting compound.

The reaction temperature is usually in a range of 0 to 100° C. and the reaction time is usually in a range of 0.1 to 24 hours.

After completion of the reaction, the objective compound can be isolated by subjecting to post treatment such as extracting a reaction mixture with an organic solvent and drying and concentrating the organic layer. The isolated objective compound can also be further purified by chromatography, recrystallization, and the like.

The compound represented by the formula (2) can be also produced according to a method described in "Experimental Chemistry Course" 4$^{th}$ Edition 20, pp 279-318 (published by MARUZEN).

Then, specific examples of the compounds of the present invention are shown below. Hereinafter, a methyl group is occasionally described as Me and an ethyl group is occasionally described as Et.

The Compound Represented by the Formula (E1)

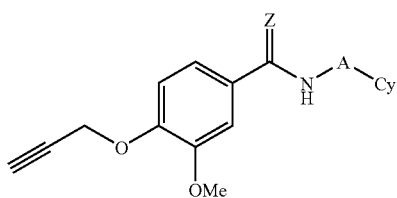

(E1)

In the above-mentioned formula (E1), the respective substituents of A, Cy and Z are the combinations described in Table 1 to Table 4.

TABLE 1

| A | Z | Cy |
|---|---|---|
| — | O | cyclopropyl |
| — | O | cyclobutyl |
| — | O | cyclopentyl |
| — | O | cyclohexyl |
| — | O | 1-methylcyclopentyl |
| — | O | 2-methylcyclopentyl |
| — | O | 3-methylcyclopentyl |
| — | O | 1-methylcyclohexyl |
| — | O | 2-methylcyclohexyl |
| — | O | 3-methylcyclohexyl |
| — | O | 4-methylcyclohexyl |
| — | O | 1-ethynylcyclohexyl |
| — | O | 2-chlorocyclohexyl |
| — | O | 3-chlorocyclohexyl |
| — | O | 4-chlorocyclohexyl |
| — | O | 1-hydroxycyclohexyl |
| — | O | 2-hydroxycyclohexyl |
| — | O | 3-hydroxycyclohexyl |
| — | O | 4-hydroxycyclohexyl |
| — | O | 2,2-dimethylcyclohexyl |
| — | O | 2,3-dimethylcyclohexyl |
| — | O | 2,6-dimethylcyclohexyl |
| $CH_2$ | O | cyclopropyl |
| $CH_2$ | O | cyclobutyl |

TABLE 2

| A | Z | Cy |
|---|---|---|
| $CH_2$ | O | cyclopentyl |
| $CH_2$ | O | cyclohexyl |
| $CH_2$ | O | 1-methylcyclopentyl |
| $CH_2$ | O | 1-methylcyclohexyl |
| $CH_2$ | O | 1-hydroxycyclohexyl |
| CH(Me) | O | cyclopropyl |
| CH(Me) | O | cyclobutyl |
| CH(Me) | O | cyclopentyl |
| CH(Me) | O | cyclohexyl |
| CH(Me) | O | 1-methylcyclopentyl |
| CH(Me) | O | 1-methylcyclohexyl |
| CH(Me) | O | 1-hydroxycyclohexyl |
| $C(Me)_2$ | O | cyclopropyl |
| $C(Me)_2$ | O | cyclobutyl |
| $C(Me)_2$ | O | cyclopentyl |
| $C(Me)_2$ | O | cyclohexyl |
| $C(Me)_2$ | O | 1-methylcyclopentyl |
| $C(Me)_2$ | O | 1-methylcyclohexyl |
| CH(Et) | O | cyclopropyl |
| CH(Et) | O | cyclobutyl |
| CH(Et) | O | cyclopentyl |
| CH(Et) | O | cyclohexyl |
| CH(Et) | O | 1-methylcyclopentyl |
| CH(Et) | O | 1-methylcyclohexyl |

TABLE 3

| A | Z | Cy |
|---|---|---|
| — | S | cyclopropyl |
| — | S | cyclobutyl |
| — | S | cyclopentyl |
| — | S | cyclohexyl |
| — | S | 1-methylcyclopentyl |
| — | S | 2-methylcyclopentyl |
| — | S | 3-methylcyclopentyl |
| — | S | 1-methylcyclohexyl |
| — | S | 2-methylcyclohexyl |
| — | S | 3-methylcyclohexyl |
| — | S | 4-methylcyclohexyl |
| — | S | 1-ethynylcyclohexyl |
| — | S | 2-chlorocyclohexyl |
| — | S | 3-chlorocyclohexyl |
| — | S | 4-chlorocyclohexyl |

TABLE 3-continued

| A | Z | Cy |
|---|---|---|
| — | S | 1-hydroxycyclohexyl |
| — | S | 2-hydroxycyclohexyl |
| — | S | 3-hydroxycyclohexyl |
| — | S | 4-hydroxycyclohexyl |
| — | S | 2,2-dimethylcyclohexyl |
| — | S | 2,3-dimethylcyclohexyl |
| — | S | 2,6-dimethylcyclohexyl |
| CH$_2$ | S | cyclopropyl |
| CH$_2$ | S | cyclobutyl |

TABLE 4

| A | Z | Cy |
|---|---|---|
| CH$_2$ | S | cyclopentyl |
| CH$_2$ | S | cyclohexyl |
| CH$_2$ | S | 1-methylcyclopentyl |
| CH$_2$ | S | 1-methylcyclohexyl |
| CH$_2$ | S | 1-hydroxycyclohexyl |
| CH(Me) | S | cyclopropyl |
| CH(Me) | S | cyclobutyl |
| CH(Me) | S | cyclopentyl |
| CH(Me) | S | cyclohexyl |
| CH(Me) | S | 1-methylcyclopentyl |
| CH(Me) | S | 1-methylcyclohexyl |
| CH(Me) | S | 1-hydroxycyclohexyl |
| C(Me)$_2$ | S | cyclopropyl |
| C(Me)$_2$ | S | cyclobutyl |
| C(Me)$_2$ | S | cyclopentyl |
| C(Me)$_2$ | S | cyclohexyl |
| C(Me)$_2$ | S | 1-methylcyclopentyl |
| C(Me)$_2$ | S | 1-methylcyclohexyl |
| CH(Et) | S | cyclopropyl |
| CH(Et) | S | cyclobutyl |
| CH(Et) | S | cyclopentyl |
| CH(Et) | S | cyclohexyl |
| CH(Et) | S | 1-methylcyclopentyl |
| CH(Et) | S | 1-methylcyclohexyl |

The Compound Represented by the Formula (E2)

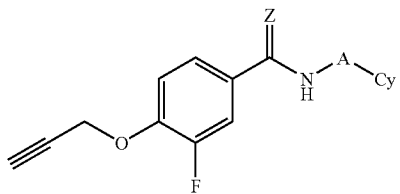

(E2)

In the above-mentioned formula (E2), the respective substituents of A, Cy and Z are the combinations described in Table 1 to Table 4.

The Compound Represented by the Formula (E3)

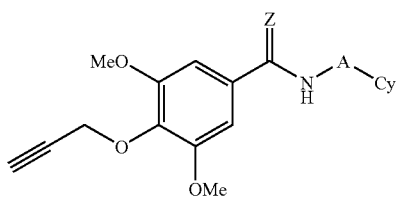

(E3)

In the above-mentioned formula (E3), the respective substituents of A, Cy and Z are the combinations described in Table 1 to Table 4.

The Compound Represented by the Formula (E4)

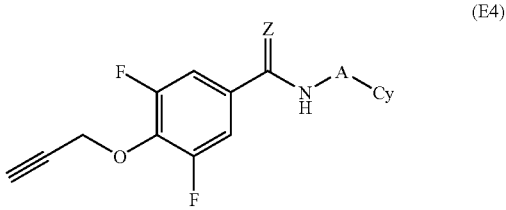

(E4)

In the above-mentioned formula (E4), the respective substituents of A, Cy and Z are the combinations described in Table 1 to Table 4.

The Compound Represented by the Formula (E5)

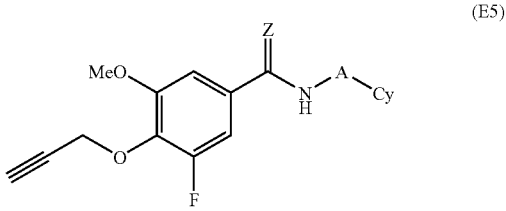

(E5)

In the above-mentioned formula (E5), the respective substituents of A, Cy and Z are the combinations described in Table 1 to Table 4.

Examples of plant diseases for which the compound of the present invention has controlling activity include plant diseases by *Pycomycetes* (*Oomycetes*), plant diseases by fungi and plant diseases by bacteria and specifically include the followings:

*Pyricularia oryzae*, *Cochliobolus miyabeanus* and *Rhizoctonia solani* of rice plant;

*Erysiphe graminis*, *Gibberella zeae*, *Puccinia striiformis*, *P. graminis*, *P. recondita*, *P. hordei*, *Typhula* sp., *Micronectriella nivalis*, *Ustilago tritici*, *U. nuda*, *Tilletia caries*, *Pseudocercosporella herpotrichoides*, *Rhynchosporium secalis*, *Septoria tritici* and *Leptosphaeria nodorum* of wheat, barley, rye and oats;

*Diaporthe citri*, *Elsinoe fawcetti*, *Penicillium digitatum* and *P. italicum* of citrus;

*Sclerotinia mali*, *Valsa mali*, *Podosphaera leucotricha*, *Alternaria mali* and *Venturia inaequalis* of apple;

*Venturia nashicola*, *V. pirina*, *Alternaria kikuchiana* and *Gymnosporangium haraeanum* of pear;

*Sclerotinia cinerea*, *Cladosporium carpophilum* and *Phomopsis* sp. of peach;

*Elsinoe ampelina*, *Glomerella cingulata*, *Uncinula necator*, *Phakopsora ampelopsidis*, *Guignardia bidwellii* and *Plasmopara viticola* of grape;

*Gloeosporium kaki*, *Cercospora kaki* and *Mycosphaerella nawae* of Japanese persimmon;

*Colletotrichum lagenarium*, *Sphaerotheca fuliginea*, *Mycosphaerella melonis*, *Fusarium oxysporum*, *Pseudoperonospora cubensis*, *Phytophthora* sp. and *Pythium* sp. of gourd;

*Alternaria solani*, *Cladosporium fulvum* and *Phytophthora infestans* of tomato;

*Phomopsis vexans* and *Erysiphe cichoracearum* of eggplant;

*Alternaria japonica* and *Cercosporella brassicae* of Cruciferae;
*Puccinia allii* of leek;
*Cercospora kikuchii*, *Elsinoe glycines* and *Diaporthe phaseolorum* var. *sojae* of soybean;
*Colletotrichum lindemthianum* of butter bean;
*Cercospora personata* and *Cercospora arachidicola* of peanut;
*Erysiphe pisi* of pea;
*Alternaria solani* and *Phytophthora infestans* of potato;
*Sphaerotheca humuli* of strawberry;
*Exobasidium reticulatum* and *Elsinoe leucospila* of tea;
*Alternaria longipes*, *Erysiphe cichoracearum*, *Colletotrichum tabacum*, *Peronospora tabacina* and *Phytophthora nicotianae* of tobacco;
*Cercospora beticola* of sugar beet;
*Diplocarpon rosae* and *Sphaerotheca pannosa* of rose;
*Septoria chrysanthemi-indici* and *Puccinia horiana* of crythansumum; and
*Botrytis cinerea* and *Sclerotinia sclerotiorum* of various crops.

The composition for controlling plant diseases of the present invention comprises the compound of the present invention as an effective ingredient and an inactive carrier. Usually, the composition for controlling plant diseases of the present invention is a preparation in the form of emulsion, wettable powder, water dispersible granule, flowable agent, dusts, granules, etc., which is prepared by mixing the compound of the present invention, an inactive carrier (solid carrier, liquid carrier and the like), and, if necessary, a surfactant and other adjuvants for preparation. These preparations contain usually 0.1 to 90% by weight of the compound of the present invention.

Examples of the solid carrier used for the preparation include fine powder or granules composed of minerals such as kaoline clay, attabalgite clay, bentonite, montmorillonite, acidic white clay, pyrofillite, talc, diatom earth, lime stones, etc.; natural organic materials such as corn cob powder, walnut shell powder, etc.; synthetic organic materials such as urea, etc.; salts such as calcium carbonate, ammonium sulfate, etc.; synthetic inorganic materials such as synthetic hydrated silicon oxide, etc. Examples of the liquid carrier include aromatic hydrocarbons such as xylene, alkylbenzene, methylnaphthalene, etc.; alcohols such as 2-propanol, ethylene glycol, propylene glycol, ethylene glycol monomethyl ether, etc.; ketones such as acetone, cyclohexane, isophorone, etc.; vegetable oils such as soy bean oil, cotton seed oil, etc.; aliphatic hydrocarbons; esters; dimethylsulfoxide; acetonitrile; and water.

Examples of the surfactant include anionic surfactants such as a salt of alkyl sulfate, a salt of alkylaryl sulfonate, a salt of dialkylsulfo succinate, a salt of polyoxyethylenealkylaryl ether phosphoric acid ester, a salt of lignin sulfonate, a naphthalene sulfonate and formaldehyde polycondensation, etc.; and nonionic surfactants such as polyoxyethylenealkyl aryl ether, polyoxyethylenealkyl polyoxypropylene block copolymer, a fatty acid ester of sorbitan, etc.

Examples of other adjuvants for preparation include water-soluble polymers such as polyvinyl alcohol, polyvinyl pyrrolidone, etc.; polysaccharides such as gum arabic, arginic acid and its salt, CMC (carboxymethylcellulose), xanthan gum, etc.; inorganic substances such as aluminum magnesium silicate, alumina sol, etc.; an antiseptic agent; a colorant; and stabilizers such as PAP (acidic isopropyl phosphate), BHT, etc.

The composition for controlling plant diseases of the present invention is used, for example, for protecting a plant from plant diseases by treating the plant itself, and by treating soil from which used for protecting a plant grown in soil where the plant is growing.

When the composition for controlling plant diseases of the present invention is used for treating the stem or leaves of a plant, or when it is used for treating soil, the amount to be used can be changed depending on the kind of an objective crop, the kind and severity of an objective disease to be treated, the form of a preparation, the treatment timing, weather conditions, and the like, but the amount is usually 1 to 5000 g, preferably 5 to 1000 g per 10,000 $m^2$ in terms of the compound of the present invention.

In case of using emulsion, wettable powder, flowable agent or the like for treatment, it is diluted with water and sprayed. In this case, the concentration of the compound of the present invention is usually in a range of 0.0001 to 3% by weight and preferably 0.0005 to 1% by weight. Dusts and granules are usually treated as they are without being diluted.

Further, the composition for controlling plant diseases of the present invention can also be used in a seed disinfection method, and the like. Examples of the seed disinfection method include immersion of seeds of a plant in the composition for controlling plant diseases of the present invention at concentration of 1 to 1,000 ppm in terms of the compound of the present invention; spraying or coating of the composition for controlling plant diseases of the present invention on seeds of a plant at concentration of 1 to 1,000 ppm in terms of the compound of the present invention; and coating on seeds of a plant with the composition for controlling plant diseases of the present invention in the form of dust.

Usually, the method of controlling plant diseases of the present invention is carried out by treating a plant which is suspected of contraction of a plant disease or soil where such a plant is growing, and/or a plant which is confirmed to contract a plant disease or soil where such a plant is growing with an effective amount of the composition for controlling plant diseases of the present invention.

The composition for controlling plant diseases of the present invention is usually used as a plant disease-controlling preparation for agricultural gardening, that is, a plant disease-controlling plant disease preparation for controlling plant diseases of a field, a paddy field, a fruit orchard, a tea field, a meadow, a turf glass field, and the like.

The composition for controlling plant diseases of the present invention can also be used together with other plant disease-controlling preparations, insecticidal preparations, acaricidal preparations, nematicidal preparations, herbicides, plant growth regulating preparations and/or fertilizers.

Examples of the effective ingredient of such plant disease-controlling preparation include chlorothalonil, fluazinam, dichlofluanide, phosetyl-A1, cyclic imido derivatives (captan, captafol, folpet, and the like), dithiocarbamate derivatives (maneb, mancozeb, thiram, ziram, zineb, propineb, and the like), inorganic or organic copper derivatives (basic copper sulfate, basic copper chloride, copper hydroxide, oxine-copper, and the like), acyl alanine derivatives (metalaxyl, furalaxyl, ofurace, cyprofuram, benalaxyl, oxadixyl, and the like), strobilurin like compounds (kresoxim-methyl, azoxystrobin, trifloxystrobin, picoxystrobin, pyraclostrobin, dimoxystrobin, and the like), anilinopyridine derivatives (cyprodinil, pyrimethanil, mepanipyrim, and the like), phenylpyrrole derivative (fenpiclonil, fludioxonil, and the like), imido derivatives (procymidone, iprodione, vinclozolin, and the like), benzimidazole derivatives (carbendazime, benomyl, thiabendazole, thiophanate-methyl, and the like), amine derivatives (fenpropimorph, tridemorph, fenpropidine, spiroxamine, and the like), azole derivatives (propiconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, prothioconazole, and the like), propamocarbe, cymoxanil, dimethomorph, famoxadone, fenamidone, pyribencarb, iprovalicarb, benthiavalicarb, mandipropamide, cyazofamid, amisulbrom, zoxamide, ethaboxam, boscalid, fenhexamid, quinoxyfen, proquinazid, metraphenone, cyflufenamid, diethofencarb, fluopicolide and acibenzolar-S-methyl.

Hereinafter, the present invention will be illustrated in more detail by Production Examples, Preparation Examples, Test Examples and the like, but the present invention is not limited thereto.

First, the production of the compounds of the present invention will be illustrated by Production Examples.

PRODUCTION EXAMPLE 1

A mixture of 3.6 g of cyclohexylmethylamine, 3.5 g of triethylamine and 10 ml of ethyl acetate was added dropwise under ice cooling to a mixture of 75 ml of ethyl acetate and 7.4 g of 4-(2-propynyloxy)-3,5-dimethoxybenzoyl chloride. The mixture obtained was stirred at room temperature for 4 hours. Then, ethyl acetate was added to the reaction mixture and it was filtered through Celite. The filtrate was concentrated under reduced pressure. The residue was subjected to silica gel column chromatography to obtain 7.7 g of N-cyclohexylmethyl-4-(2-propynyloxy)-3,5-dimethoxybenzamide (hereinafter, described as the compound 1 of the present invention) represented by the formula:

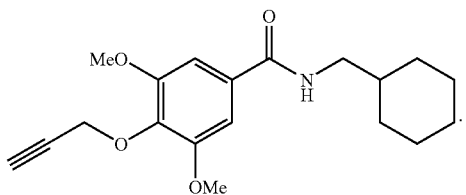

The Compound 1 of the Present Invention:

$^1$H-NMR (CDCl$_3$) δ: 0.92-1.08 (2H, m), 1.10-1.32 (3H, m), 1.48-1.89 (6H, m), 2.43 (1H, t, J=2.4 Hz), 3.29 (2H, t, J=6.4 Hz), 3.90 (6H, s), 4.76 (2H, d, J=2.4 Hz), 6.18 (1H, br s), 6.99 (2H, s)

PRODUCTION EXAMPLE 2

To a mixture of 3 ml of THF and 0.3 g of 3-methoxy-4-(2-propynyloxy)benzoyl chloride were added dropwise 0.19 g of 2-methylcyclohexylamine and 0.16 g of triethylamine in order under ice cooling. The mixture obtained was stirred at room temperature for 4 hours. Then, ethyl acetate was added to the reaction mixture and it was filtered through Celite. The filtrate was concentrated under reduced pressure. The residue was subjected to silica gel column chromatography to obtain 0.36 g of N-(2-methylcyclohexyl)-3-methoxy 4-(2-propynyloxy)benzamide (hereinafter, described as the compound 2 of the present invention) represented by the formula:

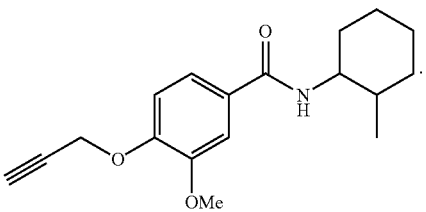

The Compound 2 of the Present Invention:

$^1$H-NMR (CDCl$_3$) δ: 0.94 (1.0H, d, J=6.8 Hz), 0.99 (2.0H, d, J=6.6 Hz), 1.08-1.83 (8.0H, m), 1.91-2.10 (1.0H, m), 2.47-2.52 (1.0H, m), 3.69 (0.7H, ddd, J=20.2, 10.4, 3.6 Hz), 3.92 (3.1H, s), 4.21-4.29 (0.3H, m), 4.79 (2.0H, d, J=2.4 Hz), 5.76 (0.7H, d, J=8.5 Hz), 6.04 (0.3H, d, J=7.1 Hz), 7.00-7.05 (1.0H, m), 7.22 (1.0H, dd, J=8.3, 1.7 Hz), 7.43-7.47 (1.0H, m).

PRODUCTION EXAMPLE 3

According to the same method as that of Production Example 2,3-methylcyclohexylamine was used in place of 2-methylcyclohexylamine to obtain N-(3-methylcyclohexyl)-4-(2-propynyloxy)-3-methoxybenzamide (hereinafter, described as the compound 3 of the present invention) represented by the formula:

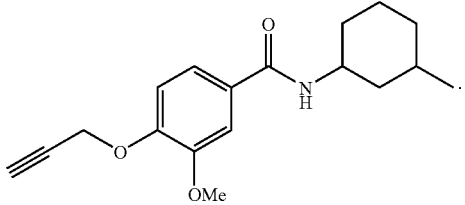

The Compound 3 of the Present Invention:

$^1$H-NMR (CDCl$_3$) δ: 0.77-1.84 (10.0H, m), 2.02-2.16 (2.0H, m), 2.52 (1.0H, t, J=2.2 Hz), 3.90-3.98 (3.8H, m), 4.28-4.38 (0.2H, m), 4.81 (2.0H, t, J=2.2 Hz), 5.88 (0.8H, d, J=7.2 Hz), 6.16 (0.2H, d, J=7.0 Hz), 7.01 (0.8H, d, J=8.5 Hz), 7.03 (0.2H, d, J=8.2 Hz), 7.22 (1.0H, dd, J=8.5, 1.9 Hz), 7.43 (0.8H, d, J=1.7 Hz), 7.46 (0.2H, d, J=1.9 Hz).

PRODUCTION EXAMPLE 4

According to the same method as that of Production Example 2,4-methylcyclohexylamine was used in place of 2-methylcyclohexylamine to obtain N-(4-methylcyclohexyl)-4-(2-propynyloxy)-3-methoxybenzamide (hereinafter, described as the compound 4 of the present invention) represented by the formula:

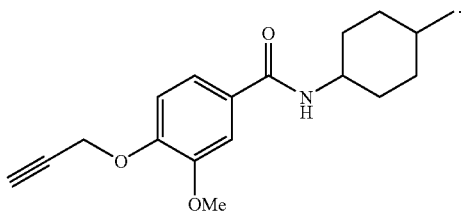

The Compound 4 of the Present Invention:
¹H-NMR (CDCl₃) δ: 0.92 (1.8H, d, J=6.6 Hz), 0.95 (1.2H, d, J=6.3 Hz), 1.04-1.43 (4.0H, m), 1.50-1.83 (4.0H, m), 2.03-2.12 (1.0H, m), 2.49-2.55 (1.0H, m), 3.83-3.99 (3.6H, m), 4.15-4.24 (0.4H, m), 4.79-4.82 (2.0H, m), 5.86 (0.6H, d, J=7.3 Hz), 6.14 (0.4H, d, J=6.8 Hz), 7.01 (0.6H, d, J=8.4 Hz), 7.03 (0.4H, d, J=8.4 Hz), 7.20-7.25 (1.0H, m), 7.43 (0.6H, d, J=2.0 Hz), 7.46 (0.4H, d, J=2.0 Hz).

PRODUCTION EXAMPLE 5

According to the same method as that of Production Example 2, cyclohexylamine was used in place of 2-methylcyclohexylamine to obtain N-(cyclohexyl)-4-(2-propynyloxy)-3-methoxybenzamide (hereinafter, described as the compound 5 of the present invention) represented by the formula:

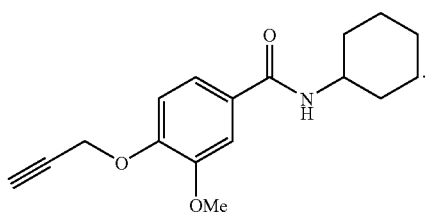

The Compound 5 of the Present Invention:
¹H-NMR (CDCl₃) δ: 1.13-1.31 (3H, m), 1.35-1.51 (2H, m), 1.59-1.81 (3H, m), 1.97-2.07 (2H, m), 2.52 (1H, t, J=2.4 Hz), 3.89-4.00 (4H, m), 4.80 (2H, d, J=2.4 Hz), 5.98 (1H, d, J=7.6 Hz), 7.01 (1H, d, J=8.3 Hz), 7.23 (1H, dd, J=8.3, 2.2 Hz), 7.44 (1H, d, J=2.0 Hz).

PRODUCTION EXAMPLE 6

According to the same method as that of Production Example 2,1-(cyclohexyl)ethylamine was used in place of 2-methylcyclohexylamine to obtain N-(1-cyclohexyl)ethyl-4-(2-propynyloxy)-3-methoxybenzamide (hereinafter, described as the compound 6 of the present invention) represented by the formula:

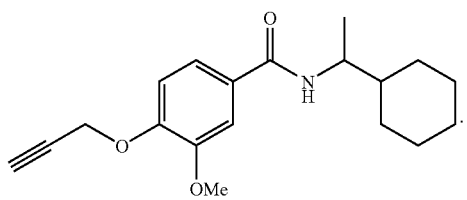

The Compound 6 of the Present Invention:
¹H-NMR (CDCl₃) δ: 0.95 (3H, t, J=7.4 Hz), 0.99-1.31 (4H, m), 1.36-1.53 (2H, m), 1.58-1.85 (5H, m), 2.53 (1H, t, J=2.3 Hz), 3.87-3.99 (4H, m), 4.81 (2H, d, J=2.2 Hz), 5.79 (1H, d, J=9.5 Hz), 7.03 (1H, d, J=8.3 Hz), 7.23 (1H, dd, J=8.3, 2.0 Hz), 7.49 (1H, d, J=2.0 Hz).

PRODUCTION EXAMPLE 7

According to the same method as that of Production Example 2,1-(cyclohexyl)propylamine was used in place of 2-methylcyclohexylamine to obtain N-(1-cyclohexyl)propyl-4-(2-propynyloxy)-3-methoxybenzamide (hereinafter, described as the compound 7 of the present invention) represented by the formula:

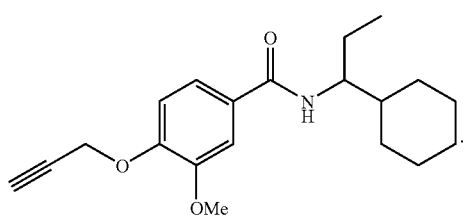

The Compound 7 of the Present Invention:
¹H-NMR (CDCl₃) δ: 0.96-1.48 (10H, m), 1.55-1.91 (6H, m), 2.52 (1H, t, J=2.4 Hz), 3.93 (3H, s), 4.00-4.13 (1H, m), 4.81 (2H, d, J=2.4 Hz), 5.92 (1H, d, J=8.8 Hz), 7.02 (1H, d, J=8.3 Hz), 7.23 (1H, dd, J=8.3, 2.2 Hz), 7.47 (1H, d, J=2.0 Hz).

PRODUCTION EXAMPLE 8

According to the same method as that of Production Example 2, (2-methylcyclohexyl)methylamine was used in place of 2-methylcyclohexylamine to obtain N-(2-methylcyclohexyl)methyl-4-(2-propynyloxy)-3-methoxybenzamide (hereinafter, described as the compound 8 of the present invention) represented by the formula:

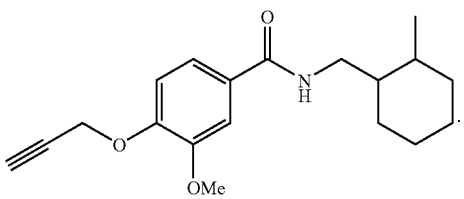

The Compound 8 of the Present Invention:
¹H-NMR (CDCl₃) δ: 0.82-1.57 (10H, m), 1.60-1.84 (2H, m), 1.87-1.97 (1H, m), 2.51-2.54 (1H, m), 3.23-3.38 (2H, m), 3.92 (3H, s), 4.80 (2H, d, J=2.4 Hz), 6.09 (1H, br s), 7.02 (1H, d, J=8.3 Hz), 7.23 (1H, dd, J=8.4, 2.1 Hz), 7.46 (1H, d, J=2.0 Hz)

PRODUCTION EXAMPLE 9

According to the same method as that of Production Example 2, (3-methylcyclohexyl)methylamine was used in place of 2-methylcyclohexylamine to obtain N-(3-methylcyclohexyl)methyl-4-(2-propynyloxy)-3-methoxybenzamide (hereinafter, described as the compound 9 of the present invention) represented by the formula:

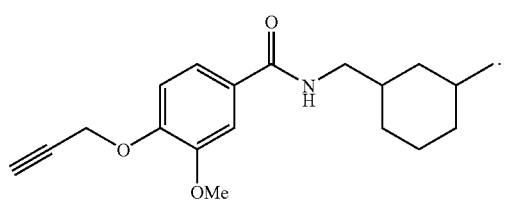

The Compound 9 of the Present Invention:
$^1$H-NMR (CDCl$_3$) δ: 0.58-0.95 (5H, m), 1.12-1.96 (8H, m), 2.53 (1H, t, J=2.4 Hz), 3.25-3.41 (2H, m), 3.93 (3H, s), 4.81 (2H, d, J=2.2 Hz), 6.07-6.21 (1H, m), 7.02 (1H, d, J=8.3 Hz), 7.20-7.28 (1H, m), 7.44-7.48 (1H, m)

PRODUCTION EXAMPLE 10

According to the same method as that of Production Example 2, cyclopropylmethylamine was used in place of 2-methylcyclohexylamine to obtain N-cyclopropylmethyl-4-(2-propynyloxy)-3-methoxybenzamide (hereinafter, described as the compound 10 of the present invention) represented by the formula:

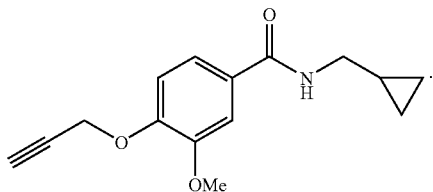

The Compound 10 of the Present Invention:
$^1$H-NMR (CDCl$_3$) δ: 0.24-0.30 (2H, m), 0.52-0.59 (2H, m), 1.00-1.11 (1H, m), 2.53 (1H, t, J=2.4 Hz), 3.30 (2H, dd, J=7.1, 5.6 Hz), 3.92 (3H, s), 4.81 (2H, d, J=2.4 Hz), 6.28 (1H, br s), 7.02 (1H, d, J=8.5 Hz), 7.29 (1H, dd, J=8.3, 2.0 Hz), 7.46 (1H, d, J=2.0 Hz).

PRODUCTION EXAMPLE 11

To a mixture of 10 ml of THF and 0.3 g of 3-methoxy-4-(2-propynyloxy)benzoyl chloride were added dropwise 0.15 g of cyclopentylmethylamine and 0.16 g of triethylamine in order under ice cooling. The mixture obtained was stirred at room temperature for 4 hours. Then, ethyl acetate was added to the reaction mixture and it was filtered through Celite. The filtrate was concentrated under reduced pressure. The residue was subjected to silica gel column chromatography to obtain 0.31 g of N-cyclopentylmethyl-4-(2-propynyloxy)-3-methoxybenzamide (hereinafter, described as the compound 11 of the present invention) represented by the formula:

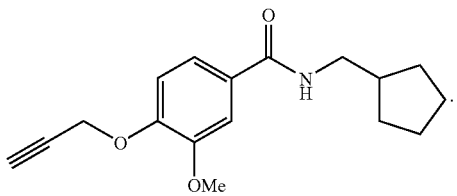

The Compound 11 of the Present Invention:
$^1$H-NMR (CDCl$_3$) δ: 1.21-1.32 (2H, m), 1.50-1.85 (6H, m), 2.09-2.22 (1H, m), 2.53 (1H, t, J=2.3 Hz), 3.38 (2H, dd, J=7.1, 5.9 Hz), 3.92 (3H, s), 4.80 (2H, d, J=2.4 Hz), 6.20 (1H, br s), 7.02 (1H, d, J=8.3 Hz), 7.25 (1H, dd, J=8.3, 2.0 Hz), 7.46 (1H, d, J=2.0 Hz).

PRODUCTION EXAMPLE 12

According to the same method as that of Production Example 2, (4-methylcyclohexyl)methylamine was used in place of 2-methylcyclohexylamine to obtain N-(4-methylcyclohexyl)methyl-4-(2-propynyloxy)-3-methoxybenzamide (hereinafter, described-as the compound 12 of the present invention) represented by the formula:

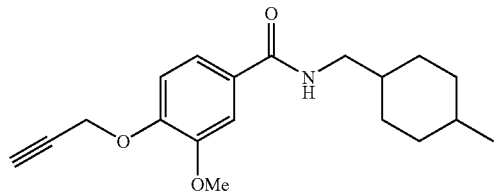

The Compound 12 of the Present Invention:
$^1$H-NMR (CDCl$_3$) δ: 0.81-1.08 (4H, m), 1.22-1.57 (6H, m), 1.59-1.82 (3H, m), 2.53 (1H, t, J=2.4 Hz), 3.26-3.42 (2H, m), 3.91 (3H, s), 4.80 (2H, d, J=2.4 Hz), 6.14-6.27 (1H, br m), 7.01 (1H, d, J=8.3 Hz), 7.25 (1H, dd, J=8.3, 2.0 Hz), 7.46 (1H, d, J=1.7 Hz).

PRODUCTION EXAMPLE 13

According to the same method as that of Production Example 2, cyclobutylmethylamine was used in place of 2-methylcyclohexylamine to obtain N-cyclobutylmethyl-4-(2-propynyloxy)-3-methoxybenzamide (hereinafter, described as the compound 13 of the present invention) represented by the formula:

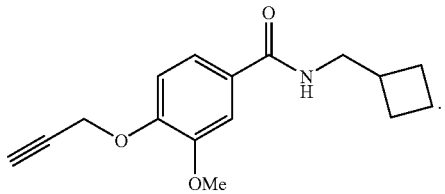

The Compound 13 of the Present Invention:
$^1$H-NMR (CDCl$_3$) δ: 1.69-1.81 (2H, m), 1.85-1.98 (2H, m), 2.03-2.15 (2H, m), 2.53 (1H, t, J=2.4 Hz), 2.54-2.64 (1H, m), 3.47 (2H, dd, J=7.2, 5.7 Hz), 3.91 (3H, s), 4.80 (2H, d, J=2.2 Hz), 6.17 (1H, br s), 7.01 (1H, d, J=8.3 Hz), 7.24 (1H, dd, J=8.4, 2.1 Hz), 7.45 (1H, d, J=2.0 Hz).

PRODUCTION EXAMPLE 14

According to the same method as that of Production Example 2, (1-methylcyclohexyl)methylamine was used in place of 2-methylcyclohexylamine to obtain N-(1-methylcyclohexyl)methyl-4-(2-propynyloxy)-3-methoxybenzamide (hereinafter, described as the compound 14 of the present invention) represented by the formula:

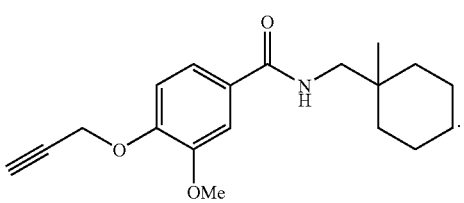

The Compound 14 of the Present Invention:
¹H-NMR (CDCl₃) δ: 0.96 (3H, s), 1.23-1.63 (10H, m), 2.52 (1H, t, J=2.4 Hz), 3.32 (2H, d, J=6.3 Hz), 3.93 (3H, s), 4.81 (2H, d, J=2.2 Hz), 6.09 (1H, br s), 7.03 (1H, d, J=8.2 Hz), 7.23 (1H, dd, J=8.5, 1.9 Hz), 7.47 (1H, d, J=1.9 Hz).

PRODUCTION EXAMPLE 15

According to the same method as that of Production Example 2, cyclopentylamine was used in place of 2-methylcyclohexylamine to obtain N-cyclopentyl-4-(2-propynyloxy)-3-methoxybenzamide (hereinafter, described as the compound 15 of the present invention) represented by the formula:

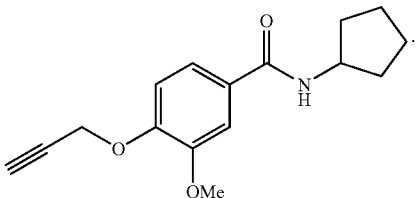

The Compound 15 of the Present Invention:
¹H-NMR (CDCl₃) δ: 1.42-1.55 (2H, m), 1.56-1.80 (4H, m), 2.00-2.15 (2H, m), 2.52 (1H, t, J=2.3 Hz), 3.91 (3H, s), 4.38 (1H, td, J=14.0, 7.0 Hz), 4.80 (2H, d, J=2.4 Hz), 6.08 (1H, d, J=6.5 Hz), 7.00 (1H, d, J=8.5 Hz), 7.23 (1H, dd, J=8.2, 1.9 Hz), 7.45 (1H, d, J=1.9 Hz).

PRODUCTION EXAMPLE 16

According to the same method as that of Production Example 2,2-hydroxycyclohexylamine was used in place of 2-methylcyclohexylamine to obtain N-(2-hydroxycyclohexyl)-4-(2-propynyloxy)-3-methoxybenzamide (hereinafter, described as the compound 16 of the present invention) represented by the formula:

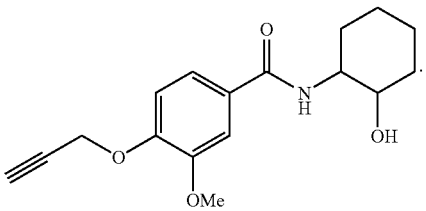

The Compound 16 of the Present Invention:
¹H-NMR (CDCl₃) δ: 1.22-1.45 (4H, m), 1.70-1.81 (2H, m), 2.01-2.15 (2H, m), 2.53 (1H, t, J=2.4 Hz), 3.43 (1H, td, J=10.0, 4.3 Hz), 3.51-3.69 (1H, m), 3.77-3.88 (1H, m), 3.91-3.95 (3H, m), 4.81 (2H, d, J=2.4 Hz), 6.10 (1H, d, J=6.5 Hz), 7.03 (1H, d, J=8.5 Hz), 7.27 (1H, dd, J=8.2, 2.2 Hz), 7.44 (1H, d, J=1.9 Hz).

PRODUCTION EXAMPLE 17

To a mixture of 10 ml of THF and 0.20 g of 3-methoxy-4-(2-propynyloxy)benzoyl chloride were added dropwise 0.22 g of cyclohexylmethylamine and 0.20 g of triethylamine in order under ice cooling The mixture obtained was stirred at room temperature for 4 hours. Then, the reaction mixture was concentrated under reduced pressure. The residue was subjected to silica gel column chromatography to obtain 0.22 g of N-cyclohexylmethyl-4-(2-propynyloxy)-3-methoxybenzamide (hereinafter, described as the compound 17 of the present invention) represented by the formula:

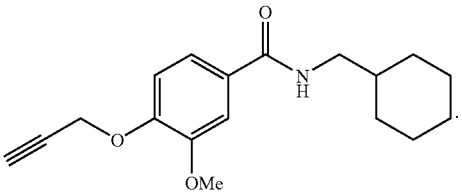

The Compound 17 of the Present Invention:
¹H-NMR (CDCl₃) δ: 0.92-1.08 (2H, m), 1.10-1.32 (3H, m), 1.51-1.83 (6H, m), 2.52 (1H, t, J=2.4 Hz), 3.29 (2H, t, J=6.5 Hz), 3.93 (3H, s), 4.81 (2H, d, J=2.4 Hz), 6.14 (1H, br s), 7.02 (1H, d, J=8.2 Hz), 7.24 (1H, dd, J=8.3, 2.1 Hz), 7.46 (1H, d, J=2.2 Hz).

PRODUCTION EXAMPLE 18

To a mixture of 20 ml of THF, 0.50 g of 2-methylcyclopentylamine hydrochloride and 1.0 g of triethylamine was added 0.50 g of 3-methoxy-4-(2-propynyloxy)benzoyl chloride. The mixture obtained was stirred at room temperature for 3 hours. Then, water was added to the reaction mixture and the mixture was extracted with ethyl acetate. The organic layer was dried and concentrated under reduced pressure. The residue was subjected to silica gel column chromatography to obtain 235 mg of N-(2-methylcyclopentyl)-3-methoxy-4-(2-propynyloxy)benzamide (hereinafter, described as the compound 18 of the present invention) represented by the formula:

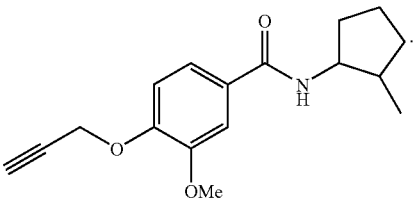

The Compound 18 of the Present Invention:
¹H-NMR (CDCl₃) δ: 0.95 (1.1H, d, J=7.0 Hz), 1.09 (1.9H, d, J=6.5 Hz), 1.21-2.32 (7.0H, m), 2.51-2.53 (1.0H, m), 3.92-4.02 (0.7H, m), 3.93 (3.0H, s), 4.40-4.48 (0.3H, m), 4.81 (2.0H, d, J=2.4 Hz), 5.92-5.94 (1.0H, br m), 7.00-7.04 (1.0H, m), 7.20-7.25 (1.0H, m), 7.45-7.48 (1.0H, m).

PRODUCTION EXAMPLE 19

To a mixture of 15 ml of THF and 0.45 g of 3,5-dimethoxy-4-(2-propynyloxy)benzoyl chloride were added 0.24 g of 2-methylcyclohexylamine and 0.27 g of triethylamine in order at room temperature. The mixture obtained was stirred at room temperature for 4 hours. Then, ethyl acetate was added to the reaction mixture and the mixture was filtered through Celite. The filtrate was concentrated under reduced pressure. The residue obtained was washed with methyl tert-butyl ether and hexane to obtain 0.49 g of N-(2-methylcyclohexyl)-3,5-dimethoxy-4-(2-propynyloxy)benzamide (hereinafter, described as the compound 19 of the present invention) represented by the formula:

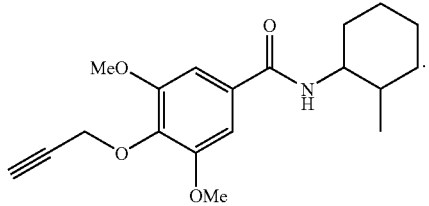

The Compound 19 of the Present Invention:

$^1$H-NMR (CDCl$_3$) δ: 0.93-0.96 (0.8H, m), 0.97-1.00 (2.2H, m), 1.09-2.09 (9.0H, m), 2.40-2.46 (1.0H, m), 3.64-3.75 (1.0H, m), 3.90 (6.6H, s), 3.91 (2.4H, s), 4.72-4.81 (2.0H, m), 5.83 (0.7H, d, J=9.2 Hz), 6.03 (0.3H, d, J=8.0 Hz), 6.97 (0.5H, s), 6.98 (1.5H, s).

PRODUCTION EXAMPLE 20

According to the same method as that of Production Example 2, (1R)-1-(cyclohexyl)ethylamine was used in place of 2-methylcyclohexylamine to obtain N-((1R)-1-cyclohexyl)ethyl-4-(2-propynyloxy)-3-methoxybenzamide (hereinafter, described as the compound 20 of the present invention) represented by the formula:

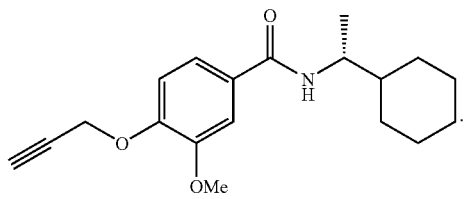

The Compound 20 of the Present Invention:

$^1$H-NMR (CDCl$_3$) δ: 0.97-1.31 (5H, m), 1.19 (3H, d, J=6.8 Hz), 1.38-1.49 (1H, m), 1.62-1.85 (5H, m), 2.52 (1H, t, J=2.4 Hz), 3.93 (3H, s), 4.02-4.12 (1H, m), 4.81 (2H, d, J=2.4 Hz), 5.87 (1H, d, J=8.5 Hz), 7.02 (1H, d, J=8.5 Hz), 7.22 (1H, dd, J=8.3, 2.1 Hz), 7.47 (1H, d, J=1.9 Hz).

PRODUCTION EXAMPLE 21

To a mixture of 10 ml of THF and 0.30 g of 3-methoxy-4-(2-propynyloxy)benzoyl chloride were added 0.21 g of (1S)-1-(cyclohexyl)ethylamine and 0.20 g of triethylamine in order at room temperature. The mixture obtained was stirred at room temperature for 4 hours. Then, ethyl acetate was added to the reaction mixture and the mixture was filtered through Celite. The filtrate was concentrated under reduced pressure. The residue was washed with methyl tert-butyl ether and hexane to obtain 0.33 g of N-((1S)-1-cyclohexylethyl)-4-(2-propynyloxy)-3-methoxybenzamide (hereinafter, described as the compound 21 of the present invention) represented by the formula:

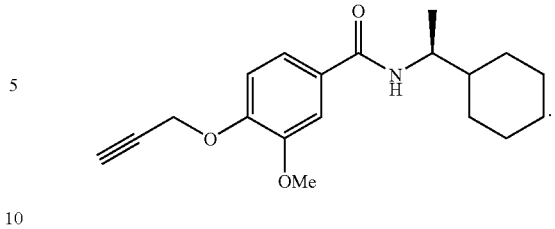

The Compound 21 of the Present Invention:

$^1$H-NMR (CDCl$_3$) δ: 0.97-1.31 (5H, m), 1.19 (3H, d, J=6.8 Hz), 1.38-1.48 (1H, m), 1.63-1.85 (5H, m), 2.52 (1H, t, J=2.3 Hz), 3.93 (3H, s), 4.01-4.13 (1H, m), 4.81 (2H, d, J=2.4 Hz), 5.88 (1H, d, J=8.7 Hz), 7.02 (1H, d, J=8.2 Hz), 7.22 (2H, dd, J=8.3, 2.1 Hz), 7.47 (1H, d, J=1.9 Hz)

PRODUCTION EXAMPLE 22

To a mixture of 10 ml of THF and 0.40 g of 3-fluoro-4-(2-propynyloxy)benzoyl chloride were added 0.45 g of cyclohexylmethylamine and 0.50 g of triethylamine in order at room temperature. The mixture obtained was stirred at room temperature for 1 hour. Then, ethyl acetate was added to the reaction mixture and the mixture was filtered through Celite. The filtrate was concentrated under reduced pressure. The residue was subjected to silica gel column chromatography to obtain 0.35 g of N-cyclohexylmethyl-3-fluoro-4-(2-propynyloxy)benzamide (hereinafter, described as the compound 22 of the present invention) represented by the formula:

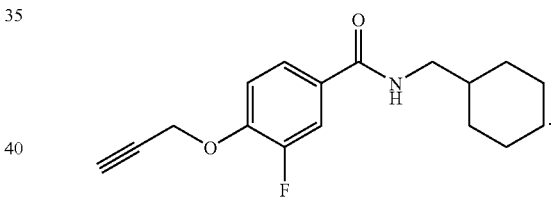

The Compound 22 of the Present Invention:

$^1$H-NMR (CDCl$_3$) δ: 0.92-1.06 (2H, m), 1.09-1.33 (3H, m), 1.49-1.82 (6H, m), 2.56 (1H, t, J=2.1 Hz), 3.28 (2H, t, J=6.4 Hz), 4.81 (2H, d, J=2.2 Hz), 6.09 (1H, br s), 7.13 (1H, t, J=8.2 Hz), 7.48-7.58 (2H, m).

PRODUCTION EXAMPLE 23

To a mixture of 5 ml of THF and 0.38 g of 3,5-dimethoxy-4-(2-propynyloxy)benzoyl chloride were added 0.21 g of (1S)-1-(cyclohexyl)ethylamine and 0.23 g of triethylamine in order at room temperature. The mixture obtained was stirred at room temperature for 4 hours. Then, ethyl acetate was added to the reaction mixture and the mixture was filtered through Celite. The filtrate was concentrated under reduced pressure. The residue was subjected to silica gel column chromatography to obtain 0.42 g of N-((1S)-1-cyclohexylethyl)-4-(2-propynyloxy)-3,5-dimethoxybenzamide (hereinafter, described as the compound 23 of the present invention) represented by the formula:

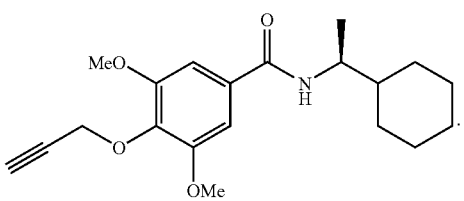

The Compound 23 of the Present Invention:
¹H-NMR (CDCl₃) δ: 0.85-1.31 (5H, m), 1.19 (3H, d, J=6.8 Hz), 1.37-1.50 (1H, m), 1.61-1.86 (5H, m), 2.43 (1H, t, J=2.4 Hz), 3.89-3.91 (6H, m), 3.99-4.12 (1H, m), 4.76 (2H, d, J=2.4 Hz), 5.90 (1H, d, J=8.7 Hz), 6.98 (2H, s).

PRODUCTION EXAMPLE 24

N-(2-Methylcyclohexyl)-4-(2-propynyloxy)-3-methoxybenzamide obtained according to the same method as that of Production Example 2 was subjected to gel permeation chromatography to obtain trans-N-(2-methylcyclohexyl)-4-(2-propynyloxy)-3-methoxybenzamide (hereinafter, described as the compound 24 of the present invention) represented by the formula:

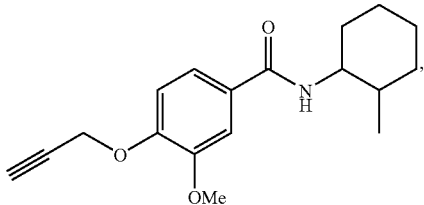

The Compound 24 of the Present Invention:
¹H-NMR (CDCl₃) δ: 0.99 (3H, dd, J=6.5, 2.9 Hz), 1.09-1.48 (5H, m), 1.67-1.84 (3H, m), 2.01-2.10 (1H, m), 2.52 (1H, t, J=2.7 Hz), 3.65-3.76 (1H, m), 3.93 (3H, d, J=2.9 Hz), 4.79-4.83 (2H, m), 5.82 (1H, d, J=8.0 Hz), 7.03 (1H, dd, J=8.2, 2.9 Hz), 7.21-7.28 (1H, m), 7.46 (1H, s); and cis-N-(2-methylcyclohexyl)-4-(2-propynyloxy)-3-methoxybenzamide (hereinafter, described as the compound 25 of the present invention) represented by the formula:

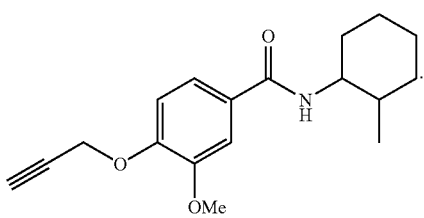

The Compound 25 of the Present Invention:
¹H-NMR (CDCl₃) δ: 0.94 (3H, d, J=7.0 Hz), 1.11-1.69 (7H, m), 1.70-1.83 (1H, m), 1.90-2.01 (1H, m), 2.53 (1H, t, J=2.4 Hz), 3.94 (3H, s), 4.21-4.32 (1H, m), 4.81 (2H, d, J=2.4 Hz), 6.09 (1H, d, J=8.5 Hz), 7.04 (1H, d, J=8.2 Hz), 7.23 (1H, dd, J=8.3, 2.1 Hz), 7.47 (1H, d, J=1.9 Hz).

PRODUCTION EXAMPLE 25

According to the same method as that of Production Example 1, cyclohexylamine was used in place of cyclohexylmethylamine to obtain N-cyclohexyl-4-(2-propynyloxy)-3,5-dimethoxybenzamide (hereinafter, described as the compound 26 of the present invention) represented by the formula:

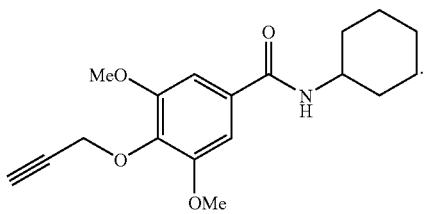

The Compound 26 of the Present Invention:
¹H-NMR (CDCl₃) δ: 1.12-1.32 (3H, m), 1.34-1.52 (2H, m), 1.59-1.83 (3H, m), 1.99-2.10 (2H, m), 2.43 (1H, t, J=2.5 Hz), 3.85-4.02 (1H, m), 3.91 (6H, s), 4.76 (2H, d, J=2.4 Hz), 5.89 (1H, d, J=7.7 Hz), 6.96 (2H, s)

PRODUCTION EXAMPLE 26

According to the same method as that of Production Example 1, cyclopentylamine was used in place of cyclohexylmethylamine to obtain N-cyclopentyl-4-(2-propynyloxy)-3,5-dimethoxybenzamide (hereinafter, described as the compound 27 of the present invention) represented by the formula:

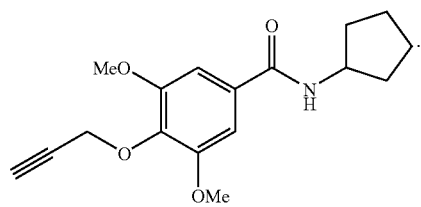

The Compound 27 of the Present Invention:
¹H-NMR (CDCl₃) δ: 1.42-1.56 (2H, m), 1.58-1.80 (4H, m), 2.04-2.16 (2H, m), 2.43 (1H, t, J=2.4 Hz), 3.90 (6H, s), 4.32-4.43 (1H, m), 4.76 (2H, d, J=2.4 Hz), 6.04 (1H, d, J=6.8 Hz), 6.97 (2H, s)

PRODUCTION EXAMPLE 27

According to the same method as that of Production Example 1, cyclobutylamine was used in place of cyclohexylmethylamine to obtain N-cyclobutyl-4-(2-propynyloxy)-3,5-dimethoxybenzamide (hereinafter, described as the compound 28 of the present invention) represented by the formula:

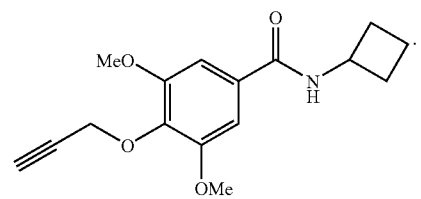

The Compound 28 of the Present Invention:
¹H-NMR (CDCl₃) δ: 1.72-1.82 (2H, m), 1.91-2.05 (2H, m), 2.37-2.49 (3H, m), 3.89 (6H, s), 4.51-4.63 (1H, m), 4.76 (2H, d, J=2.4 Hz), 6.28 (1H, d, J=7.0 Hz), 6.98 (2H, s)

PRODUCTION EXAMPLE 28

According to the same method as that of Production Example 2, 2,3-dimethylcyclohexylamine was used in place of 2-methylcyclohexylamine to obtain N-(2,3-dimethylcyclohexyl)-4-(2-propynyloxy)-3-methoxybenzamide (hereinafter, described as the compound 29 of the present invention) represented by the formula:.

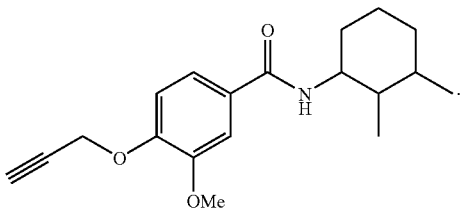

The Compound 29 of the Present Invention:
¹H-NMR (CDCl₃) δ: 0.80 (1H, d, J=7.2 Hz), 0.87-1.03 (6H, m), 1.06-2.21 (7H, m), 2.52 (1H, t, J=2.2 Hz), 3.68-4.37 (1H, m), 3.93 (3H, s), 4.81 (2H, t, J=2.4 Hz), 5.79-6.19 (1H, m), 6.98-7.06 (1H, m), 7.19-7.26 (1H, m), 7.43-7.48 (1H, m).

PRODUCTION EXAMPLE 29

To a mixture of 5 ml of THF and 0.30 g of 3,5-dimethoxy-4-(2-propynyloxy)benzoyl chloride were added 0.15 g of 1-(cyclopentyl)methylamine and 0.21 g of triethylamine in order at room temperature. The mixture obtained was stirred at room temperature for 1 hour. Then, ethyl acetate was added to the reaction mixture and the mixture was filtered through Celite. The filtrate was concentrated under reduced pressure. The residue was subjected to silica gel column chromatography to obtain 0.13 g of N-cyclopentylmethyl-3,5-dimethoxy-(2-propynyloxy)benzamide (hereinafter, described as the compound 30 of the present invention) represented by the formula:

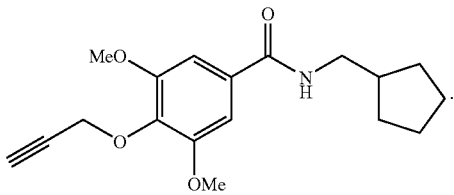

The Compound 30 of the Present Invention:
¹H-NMR (CDCl₃) δ: 1.21-1.34 (2H, m), 1.51-1.72 (4H, m), 1.73-1.87 (2H, m), 2.10-2.24 (1H, m), 2.43 (1H, t, J=2.4 Hz), 3.39 (2H, dd, J=7.4, 5.9 Hz), 3.90 (6H, s), 4.77 (2H, d, J=2.4 Hz), 6.10 (1H, br s), 6.98 (2H, s)

PRODUCTION EXAMPLE 30

According to the same method as that of Production Example 1, (1-methylcyclohexyl)methylamine was used in place of cyclohexylmethylamine to obtain N-(1-methylcyclohexyl)methyl-4-(2-propynyloxy)-3,5-dimethoxybenzamide (hereinafter, described as the compound 31 of the present invention) represented by the formula:

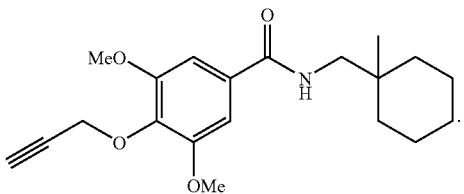

The Compound 31 of the Present Invention:
¹H-NMR (CDCl₃) δ: 0.97 (3H, s), 1.22-1.69 (10H, m), 2.44 (1H, t, J=2.5 Hz), 3.32 (2H, d, J=6.5 Hz), 3.91 (6H, s), 4.77 (2H, d, J=2.4 Hz), 6.08 (1H, br s), 6.98 (2H, s)

PRODUCTION EXAMPLE 31

To 10 ml of ethyl acetate were added 0.50 g of 3,4,5-trifluorobenzoyl chloride, 0.32 g of cyclohexylmethylamine and 0.50 g of triethylamine and the mixture obtained was stirred at room temperature for 3 hours. The reaction mixture was filtered through Celite. The filtrate was concentrated under reduced pressure. Crystals obtained were washed with a mixture of hexane and MTBE to obtain 0.70 g of N-cyclohexylmethyl-3,4,5-trifluorobenzamide. N-cyclohexylmethyl-3,4,5-trifluorobenzamide:
¹H-NMR (CDCl₃) δ: 0.92-1.80 (11H, m), 3.28 (2H, t, J=6.4 Hz), 6.17 (1H, br s), 7.42 (2H, dd, J=7.7, 6.5 Hz).

To 10 ml of DMF were added 0.50 g of N-cyclohexylmethyl-3,4,5-trifluorobenzamide and 0.15 g of propargyl alcohol and to the mixture obtained was added 100 mg of sodium hydride at 0° C. The mixture obtained was stirred at room temperature for 2 hours. Then, the reaction mixture was concentrated. The residue was subjected to silica gel column chromatography to obtain 0.49 g of N-cyclohexylmethyl-4-(2-propynyloxy)-3,5-difluorobenzamide (hereinafter, described as the compound 32 of the present invention) represented by the formula:

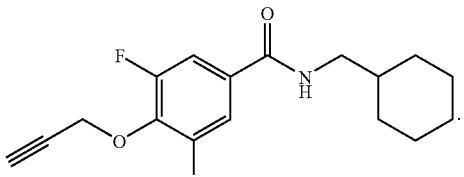

The Compound 32 of the Present Invention:
¹H-NMR (CDCl₃) δ: 0.91-1.31 (5H, m), 1.51-1.81 (6H, m), 2.52 (1H, t, J=2.4 Hz), 3.27 (2H, t, J=6.5 Hz), 4.87 (2H, d, J=2.4 Hz), 6.25 (1H, br s), 7.36 (2H, d, J=8.7 Hz).

PRODUCTION EXAMPLE 32

To 30 ml of toluene were added 1.2 g of N-cyclohexylmethyl-4-(2-propynyloxy)-3,5-dimethoxybenzamide and 1.8 g of Lawesson's Reagent and the mixture obtained was heated under reflux for 2 hours. Then, the reaction mixture was concentrated. The residue was subjected to silica gel column chromatography to obtain 0.80 g of N-cyclohexylmethyl-4-(2-propynyloxy)-3,5-dimethoxybenzenethioamide (hereinafter, described as the compound 33 of the present invention) represented by the formula:

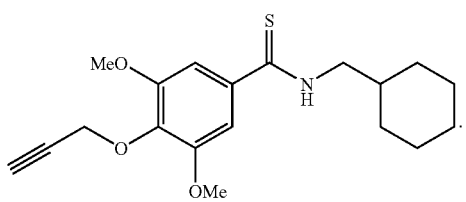

The Compound 33 of the Present Invention:
¹H-NMR (CDCl₃) δ: 1.01-1.36 (6H, m), 1.60-1.89 (5H, m), 2.44 (1H, t, J=2.4 Hz), 3.68 (2H, t, J=6.0 Hz), 3.89 (6H, s), 4.73 (2H, d, J=2.4 Hz), 6.94 (2H, s), 7.64 (1H, br s).

PRODUCTION EXAMPLE 33

To a mixture of 5 ml of ethyl acetate and 0.30 g of 3-fluoro-4-(2-propynyloxy)benzoyl chloride were added 0.19 g of 2-methylcyclohexylamine and 0.20 g of triethylamine in order at room temperature. The mixture obtained was stirred at room temperature for 1 hour. Then, ethyl acetate was added to the reaction mixture and the mixture was filtered through Celite. The filtrate was concentrated under reduced pressure. The residue was washed in order with methyl tert-butyl ether and hexane to obtain 0.38 g of N-(2-methylcyclohexyl)-3-fluoro-4-(2-propynyloxy)benzamide (hereinafter, described as the compound 34 of the present invention) represented by the formula:

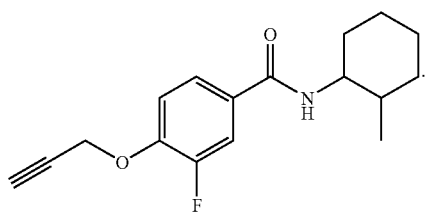

The Compound 34 of the Present Invention:
¹H-NMR (CDCl₃) δ: 0.88-1.00 (3.0H, m), 1.06-1.46 (5.0H, m), 1.53-1.83 (3.0H, m), 1.92-2.10 (1.0H, m), 2.55-2.57 (1.0H, m), 3.62-3.73 (0.7H, m), 4.20-4.29 (0.3H, m), 4.79-4.83 (2.0H, m), 5.83 (0.7H, d, J=8.7 Hz), 6.04 (0.3H, d, J=8.7 Hz), 7.08-7.17 (1.0H, m), 7.46-7.60 (2.0H, m).

PRODUCTION EXAMPLE 34

According to the same method as that of Production Example 22, cyclopentylamine was used in place of cyclohexylmethylamine to obtain N-cyclopentyl-3-fluoro-4-(2-propynyloxy)benzamide (hereinafter, described as the compound 35 of the present invention) represented by the formula:

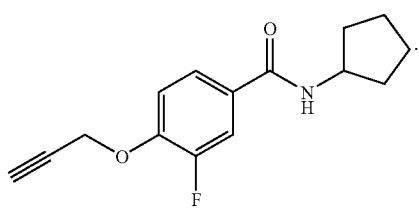

The Compound 35 of the Present Invention:
¹H-NMR (CDCl₃) δ: 1.40-1.56 (2H, m), 1.59-1.79 (4H, m), 2.02-2.15 (2H, m), 2.56 (1H, t, J=2.4 Hz), 4.32-4.43 (1H, m), 4.81 (2H, d, J=2.4 Hz), 5.97 (1H, d, J=5.3 Hz), 7.12 (1H, t, J=8.2 Hz), 7.47-7.56 (2H, m).

PRODUCTION EXAMPLE 35

According to the same method as that of Production Example 22, cyclohexylamine was used in place of cyclohexylmethylamine to obtain N-cyclohexyl-3-fluoro-4-(2-propynyloxy)benzamide (hereinafter, described as the compound 36 of the present invention) represented by the formula:

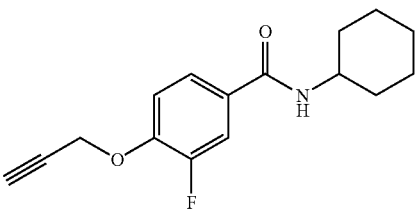

The Compound 36 of the Present Invention:
¹H-NMR (CDCl₃) δ: 1.12-1.31 (3H, m), 1.31-1.50 (2H, m), 1.58-1.83 (3H, m), 1.95-2.08 (2H, m), 2.56 (1H, s), 3.88-4.01 (1H, m), 4.81 (2H, d, J=1.7 Hz), 5.92 (1H, d, J=6.8 Hz), 7.11 (1H, t, J=8.3 Hz), 7.47-7.57 (2H, m).

PRODUCTION EXAMPLE 36

To a mixture of 5 ml of ethyl acetate and 0.30 g of 3-fluoro-4-(2-propynyloxy)benzoyl chloride were added 0.22 g of (1S)-1-(cyclohexyl)ethylamine and 0.20 g of triethylamine in order at room temperature. The mixture obtained was stirred at room temperature for 1 hour. Then, ethyl acetate was added to the reaction mixture and the mixture was filtered through Celite. The filtrate was concentrated under reduced pressure. The residue was washed with hexane to obtain 0.37 g of N-((1S)-1-cyclohexylethyl)-3-fluoro-4-(2-propynyloxy) benzamide (hereinafter, described as the compound 37 of the present invention) represented by the formula:

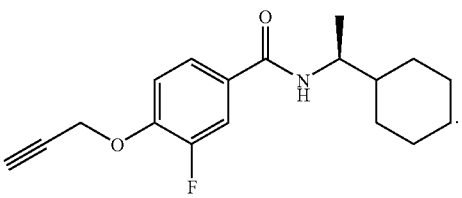

The Compound 37 of the Present Invention:
¹H-NMR (CDCl₃) δ: 0.95-1.48 (9H, m), 1.61-1.85 (5H, m), 2.56 (1H, t, J=2.4 Hz), 4.00-4.15 (1H, m), 4.81 (2H, d, J=2.4 Hz), 5.84 (1H, d, J=8.7 Hz), 7.13 (1H, t, J=8.3 Hz), 7.48-7.57 (2H, m)

PRODUCTION EXAMPLE 37

According to the same method as that of Production Example 22, (1-methylcyclohexyl)methylamine was used in place of cyclohexylmethylamine to obtain N-(1-methylcyclohexyl)methyl-3-fluoro-4-(2-propynyloxy)benzamide (hereinafter, described as the compound 38 of the present invention) represented by the formula:

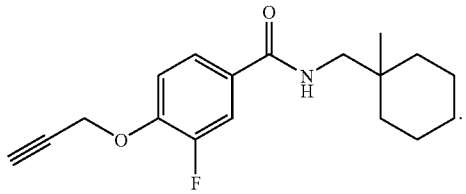

The Compound 38 of the Present Invention:
$^1$H-NMR (CDCl$_3$) δ: 0.96 (3H, s), 1.23-1.61 (10H, m), 2.56 (1H, t, J=2.4 Hz), 3.31 (2H, d, J=6.3 Hz), 4.82 (2H, d, J=2.4 Hz), 6.04 (1H, br s), 7.14 (1H, t, J=8.2 Hz), 7.48-7.58 (2H, m).

PRODUCTION EXAMPLE 38

According to the same method as that of Production Example 1,2-hydroxycyclohexylamine was used in place of cyclohexylmethylamine to obtain N-(2-hydroxycyclohexyl)-3,5-dimethoxy-4-(2-propynyloxy)benzamide (hereinafter, described as the compound 39 of the present invention) represented by the formula:

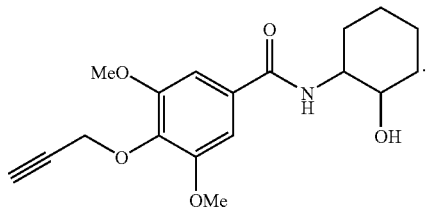

The Compound 39 of the Present Invention:
$^1$H-NMR (CDCl$_3$) δ: 1.21-1.85 (6.0H, m), 1.95-2.16 (2.0H, m), 2.43 (1.0H, t, J=2.4 Hz), 3.38-3.49 (1.3H, m), 3.77-4.16 (7.7H, m), 4.76-4.78 (2.0H, m), 6.08 (0.7H, d, J=7.0 Hz), 6.47 (0.3H, d, J=8.5 Hz), 6.98-7.00 (2.0H, m).

PRODUCTION EXAMPLE 39

According to the same method as that of Production Example 2,2-ethylcyclohexylamine was used in place of 2-methylcyclohexylamine to obtain N-(2-ethylcyclohexyl)-3-methoxy-4-(2-propynyloxy)benzamide (hereinafter, described as the compound 40 of the present invention) represented by the formula:

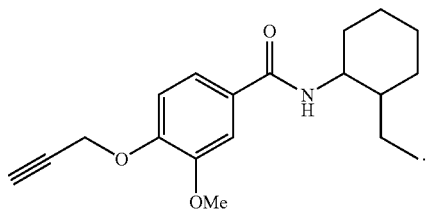

The Compound 40 of the Present Invention:
$^1$H-NMR (CDCl$_3$) δ: 0.85-0.95 (3.0H, m), 1.03-2.09 (11.0H, m), 2.51-2.54 (1.0H, m), 3.75-3.86 (0.4H, m), 3.94 (3.0H, s), 4.35-4.43 (0.6H, m), 4.80-4.82 (2.0H, m), 5.74-5.82 (0.4H, br m), 6.07-6.17 (0.6H, br m), 7.01-7.06 (1.0H, m), 7.19-7.24 (1.0H, m), 7.46-7.49 (1.0H, m).

PRODUCTION EXAMPLE 40

According to the same method as that of Production Example 22, 1-methylcyclohexylamine was used in place of cyclohexylmethylamine to obtain N-(1-methylcyclohexyl)-3-fluoro-4-(2-propynyloxy)benzamide (hereinafter, described as the compound 41 of the present invention) represented by the formula:

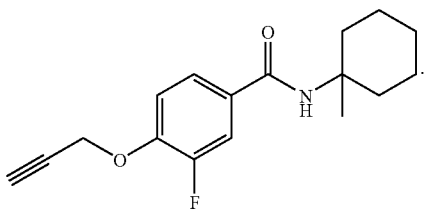

The Compound 41 of the Present Invention:
$^1$H-NMR (CDCl$_3$) δ: 1.28-1.64 (11H, m), 2.07-2.17 (2H, m), 2.56 (1H, t, J=2.4 Hz), 4.81 (2H, d, J=2.4 Hz), 5.72 (1H, br s), 7.12 (1H, t, J=8.2 Hz), 7.46-7.53 (2H, m)

PRODUCTION EXAMPLE 41

A mixture of 346 mg of 3,5-difluoro-4-(2-propynyloxy) benzoyl chloride and 1 ml of tetrahydrofuran was added dropwise under ice cooling to a mixture of 5 ml of tetrahydrofuran, 170 mg of 2-methylcyclohexylamine and 182 mg of triethylamine. The mixture obtained was stirred at room temperature for 0.5 hour. The reaction mixture was filtered. The filtrate was concentrated under reduced pressure. Water was added to the residue and the mixture was extracted with ethyl acetate. The organic layer was dried over anhydrous magnesium sulfate and concentrated under reduced pressure to obtain 295 mg of N-(2-methylcyclohexyl)-3,5-difluoro-4-(2-propynyloxy)benzamide (hereinafter, described as the compound 42 of the present invention) represented by the formula:

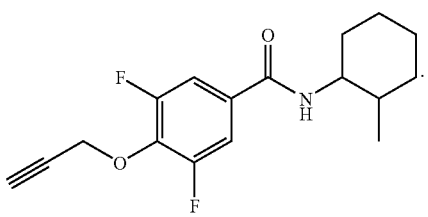

The Compound 42 of the Present Invention:
$^1$H-NMR (CDCl$_3$) δ: 0.93 (0.6H, d, J=7.1 Hz), 0.97 (2.4H, d, J=6.3 Hz), 1.07-2.08 (9.0H, m), 2.49-2.53 (1.0H, m), 3.59-3.73 (0.8H, m), 4.19-4.28 (0.2H, m), 4.85-4.89 (2.0H, m), 5.65-5.76 (0.8H, m), 5.93-6.01 (0.2H, m), 7.30-7.40 (2.0H, m).

PRODUCTION EXAMPLE 42

A mixture of 346 mg of 3,5-difluoro-4-(2-propynyloxy) benzoyl chloride and 1 ml of tetrahydrofuran was added dropwise under ice cooling to a mixture of 5 ml of tetrahydrofuran, 191 mg of ((1S)-1-cyclohexyl)ethylamine and 182 mg of triethylamine. The mixture obtained was stirred at room temperature for 0.5 hour. The reaction mixture was filtered. The filtrate was concentrated under reduced pressure. Water was added to the residue and the mixture was extracted with ethyl acetate. The organic layer was dried over anhydrous magnesium sulfate and concentrated under reduced pressure to obtain 295 mg of N-((1S)-1-cyclohexyl)ethyl-3,5-difluoro-4-(2-propynyloxy)benzamide (hereinafter, described as the compound 43 of the present invention) represented by the formula:

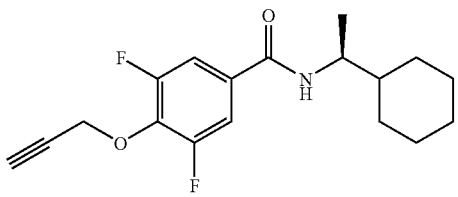

The Compound 43 of the Present Invention:

$^1$H-NMR (CDCl$_3$) δ: 1.00-1.81 (14H, m), 2.51 (1H, t, J=2.3 Hz), 3.98-4.09 (1H, m), 4.87 (2H, d, J=2.3 Hz), 5.79 (1H, d, J=10.7 Hz), 7.30-7.38 (2H, m).

PRODUCTION EXAMPLE 43

According to the same method as that of Production Example 41, cyclohexylamine was used in place of 2-methylcyclohexylamine to obtain N-cyclohexyl-3,5-difluoro-4-(2-propynyloxy)benzamide (hereinafter, described as the compound 44 of the present invention) represented by the formula:

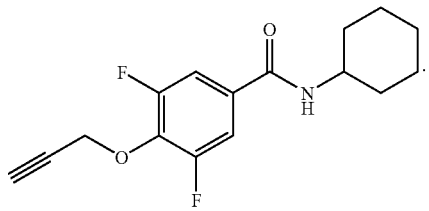

The Compound 44 of the Present Invention:

$^1$H-NMR (CDCl$_3$) δ: 1.15-1.28 (3H, m), 1.37-1.48 (2H, m), 1.62-1.80 (3H, m), 1.98-2.05 (2H, m), 2.51 (1H, t, J=2.4 Hz), 3.88-4.00 (1H, m), 4.87 (2H, d, J=2.4 Hz), 5.82 (1H, d, J=7.1 Hz), 7.29-7.38 (2H, m).

PRODUCTION EXAMPLE 44

A mixture of 200 mg of 3-fluoro-5-methoxy-4-(2-propynyloxy)benzoyl chloride and 1 ml of tetrahydrofuran was added dropwise under ice cooling to a mixture of 5 ml of tetrahydrofuran, 93 mg of cyclohexylmethylamine and 100 mg of triethylamine. Then, the mixture obtained was stirred at room temperature for 0.5 hour. The reaction mixture was filtered. The filtrate was concentrated under reduced pressure. Water was added to the residue and the mixture was extracted with chloroform. The organic layer was dried over anhydrous magnesium sulfate and concentrated under reduced pressure to obtain 223 mg of N-cyclohexylmethyl-3-fluoro-5-methoxy-4-(2-propynyloxy)benzamide (hereinafter, described as the compound 45 of the present invention) represented by the formula:

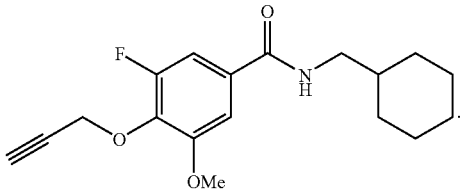

The Compound 45 of the Present Invention:

$^1$H-NMR (CDCl$_3$) δ: 0.94-1.05 (2H, m), 1.15-1.32 (3H, m), 1.52-1.81 (6H, m), 2.46 (1H, t, J=2.4 Hz), 3.29 (2H, t, J=6.5 Hz), 3.93 (3H, s), 4.82 (2H, d, J=2.4 Hz), 6.07 (1H, br s), 7.04 (1H, dd, J=10.3, 2.1 Hz), 7.24-7.27 (1H, m).

PRODUCTION EXAMPLE 45

A mixture of 200 mg of 3-fluoro-5-methoxy-4-(2-propynyloxy)benzoyl chloride and 1 ml of tetrahydrofuran was added dropwise under ice cooling to a mixture of 5 ml of tetrahydrofuran, 105 mg of ((1S)-1-cyclohexyl)ethylamine and 100 mg of triethylamine. The mixture obtained was stirred at room temperature for 0.5 hour. Then, the reaction mixture was filtered. The filtrate was concentrated under reduced pressure. Water was added to the residue and the mixture was extracted with chloroform. The organic layer was dried over anhydrous magnesium sulfate and concentrated under reduced pressure to obtain 268 mg of N-((1S)-1-cyclohexyl)ethyl-3-fluoro-5-methoxy-4-(2-propynyloxy)benzamide (hereinafter, described as the compound 46 of the present invention) represented by the formula:

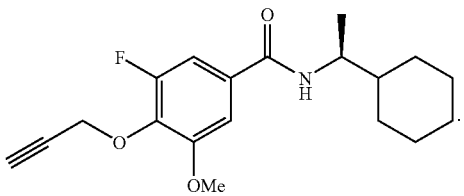

The Compound 46 of the Present Invention:

$^1$H-NMR (CDCl$_3$) δ: 0.96-1.83 (11H, m), 1.19 (3H, d, J=6.8 Hz), 2.47 (1H, t, J=2.4 Hz), 3.93 (3H, s), 4.01-4.10 (1H, m), 4.83 (2H, d, J=2.4 Hz), 5.81 (1H, d, J=8.9 Hz), 7.02 (1H, dd, J=10.3, 2.1 Hz), 7.25-7.26 (1H, m)

PRODUCTION EXAMPLE 46

According to the same method as that of Production Example 44, cyclohexylamine was used in place of cyclohexylmethylamine to obtain N-cyclohexyl-3-fluoro-5-methoxy-4-(2-propynyloxy)benzamide (hereinafter, described as the compound 47 of the present invention) represented by the formula:

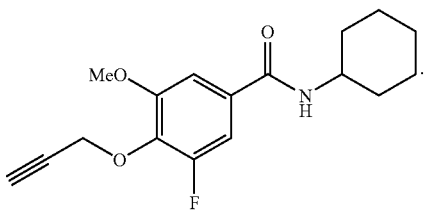

The Compound 47 of the Present Invention:

¹H-NMR (CDCl₃) δ: 1.14-1.49 (5H, m), 1.61-1.81 (3H, m), 1.97-2.07 (2H, m), 2.46 (1H, t, J=2.4 Hz), 3.88-3.99 (1H, m), 3.93 (3H, s), 4.82 (2H, d, J=2.4 Hz), 5.88 (1H, d, J=7.7 Hz), 7.03 (1H, dd, J=10.3, 2.1 Hz), 7.23 (1H, t, J=1.7 Hz)

PRODUCTION EXAMPLE 47

To a mixture of 5 ml of ethyl acetate and 0.30 g of 3-fluoro-5-methoxy-4-(2-propynyloxy)benzoyl chloride were added 0.15 g of 2-methylcyclohexylamine and 0.40 g of triethylamine in order at room temperature. The mixture obtained was stirred at room temperature for 2 hours. Then, the reaction product was subjected to silica gel column chromatography to obtain 0.34 g of N-(2-methylcyclohexyl)-3-fluoro-5-methoxy-4-(2-propynyloxy)benzamide (hereinafter, described as the compound 48 of the present invention) represented by the formula:

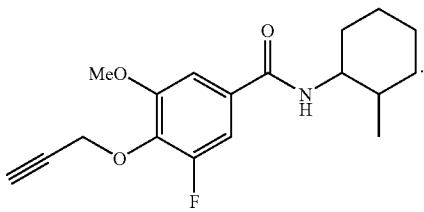

The Compound 48 of the Present Invention:

¹H-NMR (CDCl₃) δ: 0.94 (0.6H, d, J=7.0 Hz), 0.98 (2.4H, d, J=6.5 Hz), 1.08-1.48 (5.0H, m), 1.56-1.84 (3.0H, m), 2.00-2.09 (1.0H, m), 2.46-2.48 (1.0H, m), 3.63-3.73 (0.8H, m), 3.93 (3.0H, s), 4.21-4.28 (0.2H, m), 4.81-4.84 (2.0H, m), 5.76 (0.8H, d, J=8.7 Hz), 6.01 (0.2H, d, J=8.7 Hz), 7.02 (0.2H, dd, J=10.3, 2.1 Hz), 7.03 (0.8H, dd, J=10.1, 1.9 Hz), 7.25 (1.0H, t, J=1.8 Hz).

PRODUCTION EXAMPLE 48

According to the same method as that of Production Example 41, cyclopentylamine was used in place of 2-methylcyclohexylamine to obtain N-cyclopentyl-3,5-difluoro-4-(2-propynyloxy)benzamide (hereinafter, described as the compound 49 of the present invention) represented by the formula:

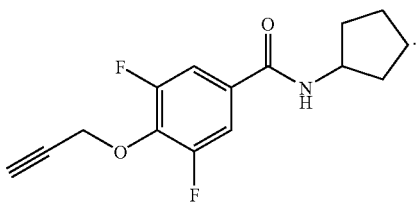

The Compound 49 of the Present Invention:

¹H-NMR (CDCl₃) δ: 1.43-1.52 (2H, m), 1.61-1.78 (4H, m), 2.05-2.14 (2H, m), 2.51 (1H, t, J=2.4 Hz), 4.36 (1H, td, J=13.9, 6.9 Hz), 4.87 (2H, d, J=2.4 Hz), 5.91 (1H, br s), 7.30-7.36 (2H, m)

PRODUCTION EXAMPLE 49

According to the same method as that of Production Example 41, 4-methylcyclohexylamine was used in place of 2-methylcyclohexylamine to obtain N-(4-methylcyclohexyl)-3,5-difluoro-4-(2-propynyloxy)benzamide (hereinafter, described as the compound 50 of the present invention) represented by the formula:

The Compound 50 of the Present Invention:

¹H-NMR (CDCl₃) δ: 0.92 (1.8H, d, J=6.3 Hz), 0.96 (1.2H, d, J=6.8 Hz), 1.08-1.26 (4H, m), 1.62-1.78 (4H, m), 2.03-2.08 (1H, m), 2.50-2.52 (1H, m), 3.82-3.92 (0.6H, m), 4.14-4.21 (0.4H, m), 4.87-4.88 (2H, m), 5.77 (0.6H, d, J=7.0 Hz), 6.04 (0.4H, d, J=7.0 Hz), 7.30-7.37 (2H, m).

PRODUCTION EXAMPLE 50

According to the same method as that of Production Example 41, cyclopropylamine was used in place of 2-methylcyclohexylamine to obtain N-cyclopropyl-3,5-difluoro-4-(2-propynyloxy)benzamide (hereinafter, described as the compound 51 of the present invention) represented by the formula:

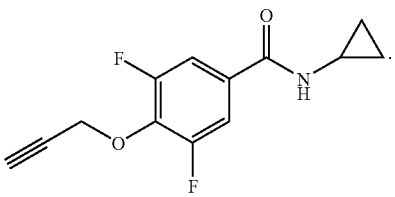

The Compound 51 of the Present Invention:

¹H-NMR (CDCl₃) δ: 0.60-0.64 (2H, m), 0.86-0.91 (2H, m), 2.51 (1H, t, J=2.4 Hz), 2.85-2.91 (1H, m), 4.87 (2H, d, J=2.4 Hz), 6.13 (1H, br s), 7.29-7.36 (2H, m).

PRODUCTION EXAMPLE 51

According to the same method as that of Production Example 41, cyclobutylamine was used in place of 2-methylcyclohexylamine to obtain N-cyclobutyl-3,5-difluoro-4-(2-propynyloxy)benzamide (hereinafter, described as the compound 52 of the present invention) represented by the formula:

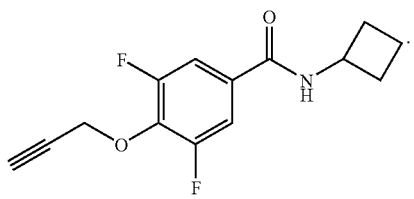

The Compound 52 of the Present Invention:

$^1$H-NMR (CDCl$_3$) δ: 1.74-1.82 (2H, m), 1.90-2.01 (2H, m), 2.40-2.47 (2H, m), 2.51 (1H, t, J=2.4 Hz), 4.55 (1H, td, J=16.2, 8.2 Hz), 4.87 (2H, d, J=2.4 Hz), 6.10 (1H, br s), 7.31-7.37 (2H, m).

PRODUCTION EXAMPLE 52

According to the same method as that of Production Example 41, 3-methylcyclohexylamine was used in place of 2-methylcyclohexylamine to obtain N-(3-methylcyclohexyl)-3,5-difluoro-4-(2-propynyloxy)benzamide (hereinafter, described as the compound 53 of the present invention) represented by the formula:

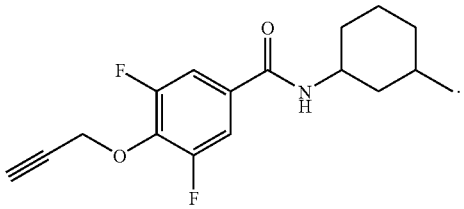

The Compound 53 of the Present Invention:

$^1$H-NMR (CDCl$_3$) δ: 0.79-2.06 (12.0H, m), 2.50-2.52 (1.0H, m), 3.88-3.97 (0.7H, m), 4.28-4.33 (0.3H, m), 4.87-4.88 (2.0H, m), 5.75 (0.7H, br s), 6.04 (0.3H, br s), 7.30-7.36 (2.0H, m).

PRODUCTION EXAMPLE 53

A mixture of 0.12 g of 2-methylcyclopentylamine, 0.2 ml of triethylamine and 1 ml of ethyl acetate was added dropwise under ice cooling to a mixture of 1 ml of ethyl acetate and 0.23 g of 3,5-difluoro-4-(2-propynyloxy)benzoyl chloride. The mixture obtained was stirred at room temperature for 12 hours. Then, the reaction mixture was subjected to silica gel column chromatography to obtain 0.07 g of N-(2-methylcyclopentyl)-3,5-difluoro-4-(2-propynyloxy)benzamide (hereinafter, described as the compound 54 of the present invention) represented by the formula:

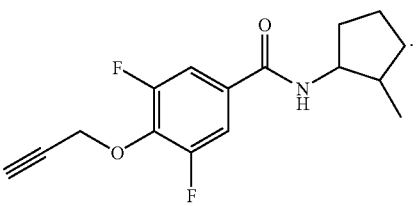

The Compound 54 of the Present Invention:

$^1$H-NMR (CDCl$_3$) δ: 0.94 (1.8H, d, J=7.0 Hz), 1.07 (1.2H, d, J=6.8 Hz), 1.26-2.29 (7.0H, m), 2.51-2.52 (1.0H, m), 3.90-3.98 (0.4H, m), 4.37-4.45 (0.6H, m), 4.87 (2.0H, d, J=2.4 Hz), 5.88-5.94 (1.0H, m), 7.30-7.38 (2.0H, m).

PRODUCTION EXAMPLE 54

N-(2-Methylcyclohexyl)-3,5-difluoro-4-(2-propynyloxy)benzamide was subjected to gel permeation chromatography to obtain cis-N-(2-methylcyclohexyl)-3,5-difluoro-4-(2-propynyloxy)benzamide (hereinafter, described as the compound 55 of the present invention) represented by the formula:

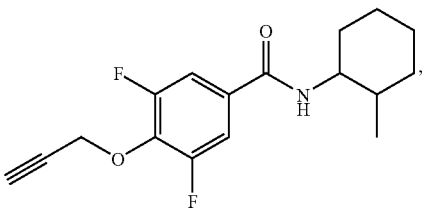

The Compound 55 of the Present Invention:

$^1$H-NMR (CDCl$_3$) δ: 0.93 (3H, d, J=7.0 Hz), 1.26-1.77 (8H, m), 1.92-2.01 (1H, m), 2.52 (1H, t, J=2.4 Hz), 4.20-4.26 (1H, m), 4.88 (2H, d, J=2.4 Hz), 6.02 (1H, d, J=8.2 Hz), 7.30-7.37 (2H, m);

and trans-N-(2-methylcyclohexyl)-3,5-difluoro-4-(2-propynyloxy)benzamide (hereinafter, described as the compound 56 of the present invention) represented by the formula:

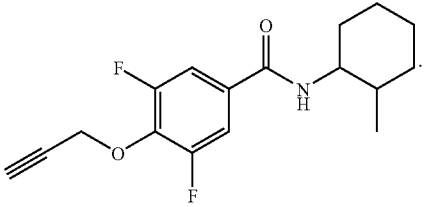

The Compound 56 of the Present Invention:

$^1$H-NMR (CDCl$_3$) δ: 0.96 (3H, d, J=6.6 Hz), 1.07-1.41 (5H, m), 1.68-1.81 (3H, m), 2.00-2.04 (1H, m), 2.52 (1H, t, J=2.4 Hz), 3.61-3.70 (1H, m), 4.86 (2H, d, J=2.2 Hz), 6.02 (1H, d, J=8.8 Hz), 7.33-7.40 (2H, m).

PRODUCTION EXAMPLE 55

According to the same method as that of Production Example 41, 1-methylcyclohexylamine was used in place of 2-methylcyclohexylamine to obtain N-(1-methylcyclohexyl)-3,5-difluoro-4-(2-propynyloxy)benzamide (hereinafter, described as the compound 57 of the present invention) represented by the formula:

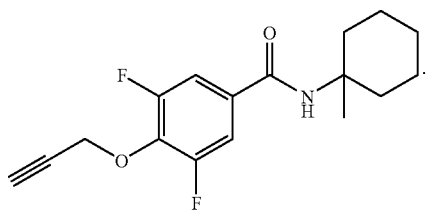

The Compound 57 of the Present Invention:

$^1$H-NMR (CDCl$_3$) δ: 1.43-2.13 (13H, m), 2.51 (1H, t, J=2.4 Hz), 4.87 (2H, d, J=2.4 Hz), 5.68 (1H, br s), 7.27-7.34 (2H, m).

PRODUCTION EXAMPLE 56

A mixture of 0.50 g of cyclopentylmethylamine, 0.4 ml of triethylamine and 2 ml of ethyl acetate was added dropwise under ice cooling to a mixture of 3 ml of ethyl acetate and 0.46 g of 3,5-difluoro-4-(2-propynyloxy)benzyl chloride. The mixture obtained was stirred at room temperature for 12 hours. Then, the reaction mixture was concentrated under reduced pressure. The residue was subjected to silica gel column chromatography to obtain 0.24 g of N-cyclopentylmethyl-3,5-difluoro-4-(2-propynyloxy)benzamide (hereinafter, described as the compound 58 of the present invention) represented by the formula:

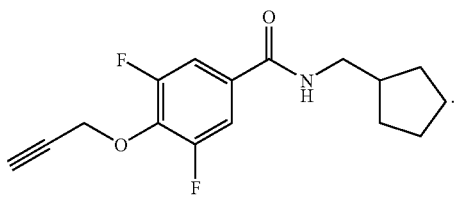

The Compound 58 of the Present Invention:

$^1$H-NMR (CDCl$_3$) δ: 1.21-1.84 (8H, m), 2.10-2.18 (1H, m), 2.52 (1H, t, J=2.4 Hz), 3.37 (2H, dd, J=7.2, 5.8 Hz), 4.87 (2H, d, J=2.4 Hz), 6.11 (1H, br s), 7.31-7.38 (2H, m).

PRODUCTION EXAMPLE 57

According to the same method as that of Production Example 41, 2,2-dimethylcyclohexylamine was used in place of 2-methylcyclohexylamine to obtain N-(2,2-dimethylcyclohexyl)-3,5-difluoro-4-(2-propynyloxy)benzamide (hereinafter, described as the compound 59 of the present invention) represented by the formula:

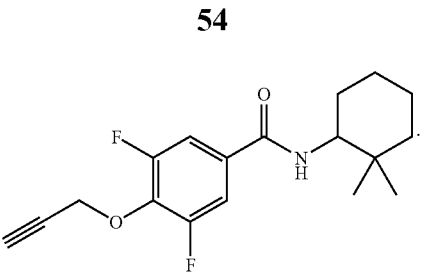

The Compound 59 of the Present Invention:

$^1$H-NMR (CDCl$_3$) δ: 0.93 (3H, s), 0.97 (3H, s), 1.36-1.59 (6H, m), 1.71-1.78 (2H, m), 2.52 (1H, t, J=2.5 Hz), 3.88-3.94 (1H, m), 4.87 (2H, d, J=2.5 Hz), 5.85 (1H, d, J=9.2 Hz), 7.30-7.37 (2H, m).

PRODUCTION EXAMPLE 58

According to the same method as that of Production Example 41, 2-ethylcyclohexylamine was used in place of 2-methylcyclohexylamine to obtain N-(2-ethylcyclohexyl)-3,5-difluoro-4-(2-propynyloxy)benzamide (hereinafter, described as the compound 60 of the present invention) represented by the formula:

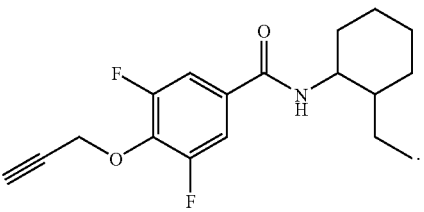

The Compound 60 of the Present Invention:

$^1$H-NMR (CDCl$_3$) δ: 0.84-0.92 (3.0H, m), 1.02-2.04 (11.0H, m), 2.52-2.54 (1.0H, m), 3.71-3.80 (0.3H, m), 4.33-4.36 (0.7H, m), 4.85-4.87 (2.0H, m), 6.23 (0.7H, br s), 6.37 (0.3H, br s), 7.31-7.43 (2.0H, m).

PRODUCTION EXAMPLE 59

According to the same method as that of Production Example 41, 2,3-dimethylcyclohexylamine was used in place of 2-methylcyclohexylamine to obtain N-(2,3-dimethylcyclohexyl)-3,5-difluoro-4-(2-propynyloxy)benzamide (hereinafter, described as the compound 61 of the present invention) represented by the formula:

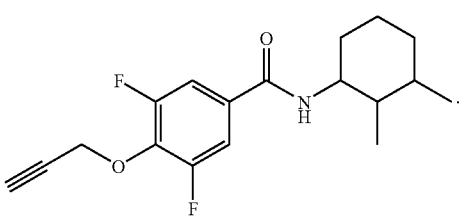

The Compound 61 of the Present Invention:

$^1$H-NMR (CDCl$_3$) δ: 0.79-2.17 (14H, m), 2.52 (1H, t, J=2.4 Hz), 3.67-4.32 (1H, m), 4.87 (2H, d, J=2.4 Hz), 5.99-6.08 (1H, m), 7.32-7.39 (2H, m).

PRODUCTION EXAMPLE 60

According to the same method as that of Production Example 41, (2-methylcyclohexyl)methylamine was used in place of 2-methylcyclohexylamine to obtain N-(2-methylcyclohexyl)methyl-3,5-difluoro-4-(2-propynyloxy)benzamide (hereinafter, described as the compound 62 of the present invention) represented by the formula:

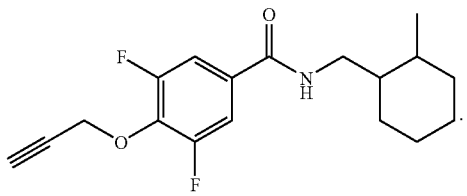

The Compound 62 of the Present Invention:

$^1$H-NMR (CDCl$_3$) δ: 0.91-1.48 (9H, m), 1.63-1.80 (3H, m), 1.88-1.94 (1H, m), 2.52 (1H, t, J=2.4 Hz), 3.24-3.66 (2H, m), 4.87 (2H, d, J=2.4 Hz), 6.18 (1H, s), 7.32-7.39 (2H, m).

PRODUCTION EXAMPLE 61

According to the same method as that of Production Example 41, 1-(cyclopropyl)ethylamine was used in place of 2-methylcyclohexylamine to obtain N-(1-cyclopropyl)ethyl-3,5-difluoro-4-(2-propynyloxy)benzamide (hereinafter, described as the compound 63 of the present invention) represented by the formula:

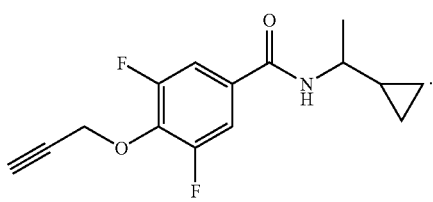

The Compound 63 of the Present Invention:

$^1$H-NMR (CDCl$_3$) δ: 0.25-0.31 (1H, m), 0.36-0.59 (3H, m), 0.87-0.96 (1H, m), 1.29 (3H, d, J=6.5 Hz), 2.53 (1H, t, J=2.4 Hz), 3.49-3.58 (1H, m), 4.87 (2H, d, J=2.4 Hz), 6.36 (1H, d, J=7.2 Hz), 7.35-7.42 (2H, m)

PRODUCTION EXAMPLE 62

According to the same method as that of Production Example 41, 2-hydroxycyclohexylamine was used in place of 2-methylcyclohexylamine to obtain N-(2-hydroxycyclohexyl)-3,5-difluoro-4-(2-propynyloxy)benzamide (hereinafter, described as the compound 64 of the present invention) represented by the formula:

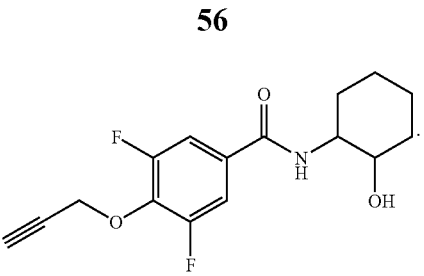

The Compound 64 of the Present Invention:

$^1$H-NMR (CDCl$_3$) δ: 1.25-2.17 (8.0H, m), 2.51 (1.0H, t, J=2.4 Hz), 2.88-4.10 (3.0H, m), 4.87-4.89 (2.0H, m), 6.02 (0.3H, d, J=5.8 Hz), 6.45 (0.7H, d, J=8.7 Hz), 7.34-7.40 (2.0H, m).

PRODUCTION EXAMPLE 63

According to the same method as that of Production Example 41, cyclopropylmethylamine was used in place of 2-methylcyclohexylamine to obtain N-cyclopropylmethyl-3,5-difluoro-4-(2-propynyloxy)benzamide (hereinafter, described as the compound 65 of the present invention) represented by the formula:

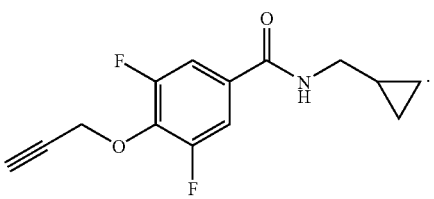

The Compound 65 of the Present Invention:

$^1$H-NMR (CDCl$_3$) δ: 0.25-0.29 (2H, m), 0.54-0.59 (2H, m), 1.02-1.08 (1H, m), 2.52 (1H, t, J=2.3 Hz), 3.29 (2H, dd, J=7.1, 5.4 Hz), 4.87 (2H, d, J=2.3 Hz), 6.28 (1H, s), 7.35-7.41 (2H, m).

PRODUCTION EXAMPLE 64

According to the same method as that of Production Example 41, cyclobutylmethylamine was used in place of 2-methylcyclohexylamine to obtain N-cyclobutylmethyl-3,5-difluoro-4-(2-propynyloxy)benzamide (hereinafter, described as the compound 66 of the present invention) represented by the formula:

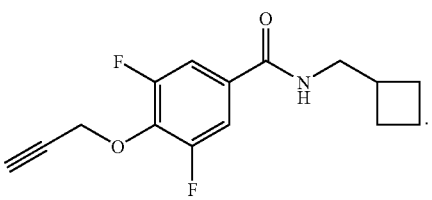

The Compound 66 of the Present Invention:

$^1$H-NMR (CDCl$_3$) δ: 1.69-1.78 (2H, m), 1.87-2.00 (2H, m), 2.06-2.14 (2H, m), 2.51-2.61 (2H, m), 3.46 (2H, dd, J=7.4, 5.7 Hz), 4.87 (2H, d, J=2.4 Hz), 6.10 (1H, br s), 7.31-7.38 (2H, m).

PRODUCTION EXAMPLE 65

According to the same method as that of Production Example 41, 2,6-dimethylcyclohexylamine was used in place of 2-methylcyclohexylamine to obtain N-(2,6-dimethylcyclohexyl)-3,5-difluoro-4-(2-propynyloxy)benzamide (hereinafter, described as the compound 67 of the present invention) represented by the formula:

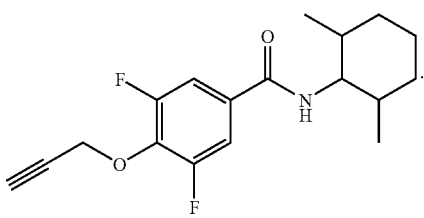

The Compound 67 of the Present Invention:
$^1$H-NMR (CDCl$_3$) δ: 0.89-2.19 (14.0H, m), 2.51-2.54 (1.0H, m), 3.40-3.47 (0.2H, m), 3.83-3.89 (0.3H, m), 4.26-4.30 (0.5H, m), 4.87-4.88 (2.0H, m), 5.73 (0.2H, d, J=10.1 Hz), 5.84 (0.5H, d, J=9.9 Hz), 5.95 (0.3H, d, J=9.2 Hz), 7.31-7.40 (2.0H, m).

PRODUCTION EXAMPLE 66

To a mixture of 1 ml of ethyl acetate and 0.2 g of 2-methylcyclopentylamine hydrochloride was added 0.48 ml of triethylamine and then, a mixture of 0.25 g of 3,5-dimethoxy-4-(2-propynyloxy)benzoyl chloride and 1 ml of ethyl acetate was added dropwise thereto under ice cooling. The mixture obtained was stirred at room temperature for 12 hours. Then, the reaction mixture was concentrated under reduced pressure. The residue was subjected to silica gel column chromatography to obtain 0.21 g of N-(2-methylcyclopentyl)-3,5-dimethoxy-4-(2-propynyloxy)benzamide (hereinafter, described as the compound 68 of the present invention) represented by the formula:

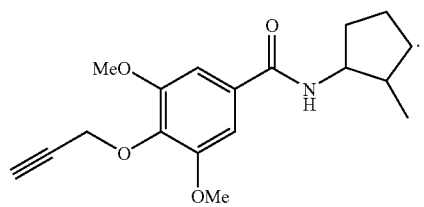

The Compound 68 of the Present Invention:
$^1$H-NMR (CDCl$_3$) δ: 0.95 (1.1H, d, J=7.0 Hz), 1.10 (1.9H, d, J=6.5 Hz), 1.57-2.17 (7.0H, m), 2.43 (1.0H, t, J=2.3 Hz), 3.91-4.01 (6.6H, m), 4.40-4.47 (0.4H, m), 4.77 (2.0H, d, J=2.4 Hz), 5.87 (1.0H, d, J=7.5 Hz), 6.96-6.98 (2.0H, m).

PRODUCTION EXAMPLE 67

To a mixture of 10 ml of THF and 0.60 g of 3,4-difluorobenzoyl chloride were added 0.37 g of 2-methylcyclopentylamine hydrochloride and 1.0 g of triethylamine, and the mixture obtained was stirred at room temperature for 3 hours. Then, ethyl acetate was added to the reaction mixture and filtered through Celite. The filtrate was concentrated under reduced pressure. The residue was subjected to silica gel column chromatography to obtain 0.55 g of N-(2-methylcyclopentyl)-3,4-difluorobenzamide.

To 2 ml of DMF were added 0.23 g of N-(2-methylcyclopentyl)-3,4-difluorobenzamide and 0.11 g of propargyl alcohol. To the mixture obtained was added 60 mg of 60% sodium hydride (oily) at 0° C. The mixture was stirred at room temperature for 2 hours. Then, dilute hydrochloric acid was added to the reaction mixture and extracted with ethyl acetate. The organic layer was washed with brine, dried on magnesium sulfate and concentrated under reduced pressure. The residue was subjected to silica gel column chromatography to obtain 0.11 g of N-(2-methylcyclopentyl)-3-fluoro-4-(2-propynyloxy)benzamide (hereinafter, described as the compound 69 of the present invention) represented by the formula:

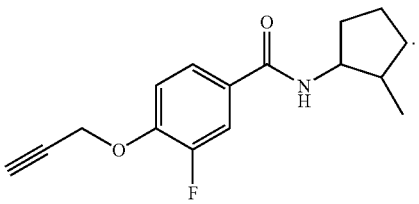

The Compound 69 of the Present Invention:
$^1$H-NMR (CDCl$_3$) δ: 0.94 (1.2H, dd, J=7.0, 0.7 Hz), 1.07 (1.8H, dd, J=6.5, 1.0 Hz), 1.26-2.27 (7.0H, m), 2.55-2.57 (1.0H, m), 3.91-3.99 (0.6H, m), 4.39-4.46 (0.4H, m), 4.81-4.81 (2.0H, m), 5.94 (1.0H, br s), 7.10-7.15 (1.0H, m), 7.49-7.56 (2.0H, m).

PRODUCTION EXAMPLE 68

To a mixture of 1 ml of ethyl acetate and 0.2 g of 2-methylcyclopentylamine hydrochloride was added 0.48 ml of triethylamine and then, a mixture of 0.24 g of 3-fluoro-5-methoxy-4-(2-propynyloxy)benzoyl chloride and 1 ml of ethyl acetate was added dropwise thereto under ice cooling. The mixture obtained was stirred at room temperature for 12 hours. Then, the reaction mixture was concentrated under reduced pressure. The residue obtained was subjected to silica gel column chromatography to obtain 0.21 g of N-(2-methylcyclopentyl)-3-fluoro-5-methoxy-4-(2-propynyloxy)benzamide (hereinafter, described as the compound 70 of the present invention) represented by the formula:

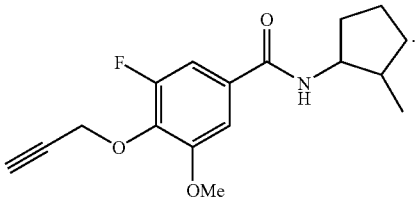

The Compound 70 of the Present Invention:
$^1$H-NMR (CDCl$_3$) δ: 0.93-0.96 (1.0H, m), 1.05-1.09 (2.0H, m), 1.24-2.28 (7.0H, m), 2.47-2.48 (1.0H, m), 3.89-3.97 (3.7H, m), 4.37-4.45 (0.3H, m), 4.81-4.82 (2.0H, m), 6.13-6.27 (1.0H, m), 7.04-7.11 (1.0H, m), 7.24-7.26 (1.0H, m).

PRODUCTION EXAMPLE 69

According to the same method as that of Production Example 1, N-(1-cyclopentyl)ethyl-3,5-difluoro-4-(2-propynyloxy)benzamide (hereinafter, described as the compound 71 of the present invention) represented by the formula:

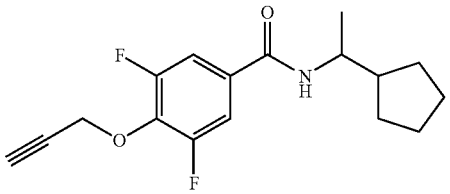

was obtained.
The Compound 71 of the Present Invention:
$^1$H-NMR (CDCl$_3$) δ: 1.21-1.82 (11H, m), 1.92 (1H, td, J=16.7, 8.5 Hz), 2.51 (1H, t, J=2.4 Hz), 3.99-4.08 (1H, m), 4.87 (2H, d, J=2.4 Hz), 5.87 (1H, d, J=8.7 Hz), 7.30-7.36 (2H, m).

PRODUCTION EXAMPLE 70

According to the same method as that of Production Example 1, N-(1-methoxycarbonylcyclohexyl)-3,5-difluoro-4-(2-propynyloxy)benzamide (hereinafter, described as the compound 72 of the present invention) represented by the formula:

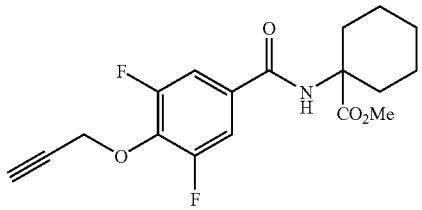

was obtained.
The Compound 72 of the Present Invention:
$^1$H-NMR (CDCl$_3$) (: 1.36-1.74 (6H, m), 1.91-1.99 (2H, m), 2.11-2.16 (2H, m), 2.52 (1H, t, J=2.4 Hz), 3.73 (3H, s), 4.88 (2H, d, J=2.4 Hz), 6.14 (1H, br s), 7.33-7.39 (2H, m).

PRODUCTION EXAMPLE 71

According to the same method as that of Production Example 1, N-(1-carboxycyclohexyl)-3,5-difluoro-4-(2-propynyloxy)benzamide (hereinafter, described as the compound 73 of the present invention) represented by the formula:

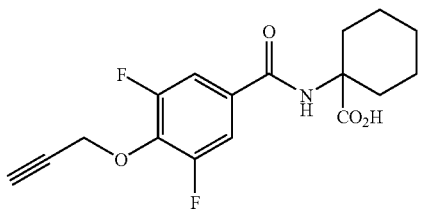

was obtained.
The Compound 73 of the Present Invention:
$^1$H-NMR (DMSO-d$_6$) δ: 1.26-1.31 (1H, m), 1.51-1.56 (5H, m), 1.71-1.77 (2H, m), 2.09-2.12 (2H, m), 3.66 (1H, t, J=2.4 Hz), 4.95 (2H, d, J=2.4 Hz), 7.64-7.70 (2H, m), 8.28 (1H, br s), 12.24 (1H, br s).

PRODUCTION EXAMPLE 72

According to the same method as that of Production Example 1, N-(1-methylcyclohexyl)methyl-3,5-difluoro-4-(2-propynyloxy)benzamide (hereinafter, described as the compound 74 of the present invention) represented by the formula:

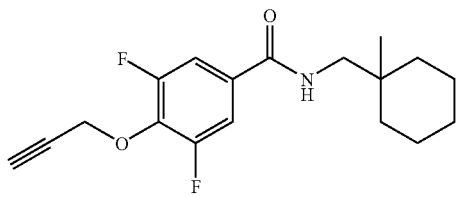

was obtained.
The Compound 74 of the Present Invention:
$^1$H-NMR (CDCl$_3$) δ: 0.96 (3H, s), 1.31-1.34 (5H, m), 1.43-1.61 (5H, m), 2.52 (1H, t, J=2.4 Hz), 3.30 (2H, d, J=6.3 Hz), 4.88 (2H, d, J=2.4 Hz), 6.04 (1H, s), 7.31-7.38 (2H, m).

PRODUCTION EXAMPLE 73

According to the same method as that of Production Example 1, N-(1-hydroxycyclohexyl)methyl-3,5-difluoro-4-(2-propynyloxy)benzamide (hereinafter, described as the compound 75 of the present invention) represented by the formula:

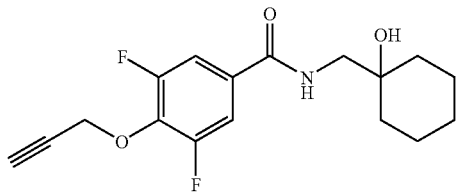

was obtained.
The Compound 75 of the Present Invention:
$^1$H-NMR (CDCl$_3$) δ: 1.35-1.58 (10H, m), 2.50-2.53 (2H, m), 3.47 (2H, d, J=5.9 Hz), 4.87 (2H, d, J=2.4 Hz), 6.75-6.76 (1H, br m), 7.37-7.43 (2H, m).

PRODUCTION EXAMPLE 74

According to the same method as that of Production Example 1, N-(1-cyanocyclohexyl)-3,5-difluoro-4-(2-propynyloxy)benzamide (hereinafter, described as the compound 76 of the present invention) represented by the formula:

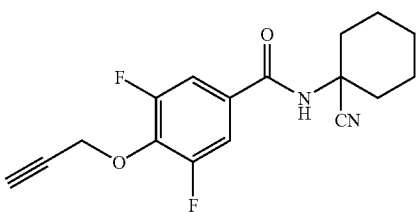

was obtained.
The Compound 76 of the Present Invention:
$^1$H-NMR (CDCl$_3$) δ: 1.31-1.39 (1H, m), 1.73-1.78 (7H, m), 2.49-2.52 (3H, m), 4.90 (2H, d, J=2.4 Hz), 5.99 (1H, br s), 7.33-7.40 (2H, m).

PRODUCTION EXAMPLE 75

According to the same method as that of Production Example 1, N-(2-ethoxycarbonylcyclohexyl)-3,5-difluoro-4-(2-propynyloxy)benzamide (hereinafter, described as the compound 77 of the present invention) represented by the formula:

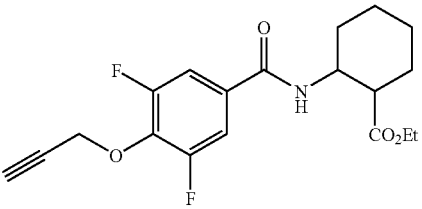

was obtained.
The Compound 77 of the Present Invention:
$^1$H-NMR (CDCl$_3$) δ: 1.18-2.26 (11H, m), 2.52 (1H, t, J=2.4 Hz), 2.85-2.89 (1H, m), 4.10-4.31 (3H, m), 4.87 (2H, d, J=2.4 Hz), 7.31-7.39 (3H, m).

PRODUCTION EXAMPLE 76

According to the same method as that of Production Example 1, N-(1-cyanocyclohexyl)-3,5-dimethoxy-4-(2-propynyloxy)benzamide (hereinafter, described as the compound 78 of the present invention) represented by the formula:

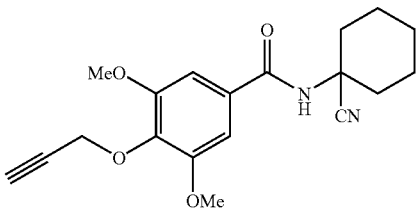

was obtained.
The Compound 78 of the Present Invention:
$^1$H-NMR (CDCl$_3$) δ: 1.19-2.01 (8H, m), 2.44 (1H, t, J=2.4 Hz), 2.50-2.54 (2H, m), 3.88 (6H, s), 4.76 (2H, d, J=2.4 Hz), 6.34 (1H, br s), 6.98 (2H, s).

PRODUCTION EXAMPLE 77

According to the same method as that of Production Example 1, N-(1-ethoxycarbonylcyclohexyl)-3,5-dimethoxy-4-(2-propynyloxy)benzamide (hereinafter, described as the compound 79 of the present invention) represented by the formula:

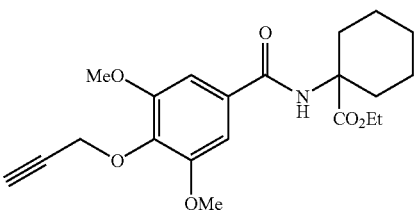

was obtained.
The compound 79 of the present invention:
$^1$H-NMR (CDCl$_3$) δ: 1.26 (3H, t, J=7.1 Hz), 1.37-1.75 (6H, m), 1.93-2.00 (2H, m), 2.15-2.18 (2H, m), 2.44 (1H, t, J=2.4 Hz), 3.91 (6H, s), 4.21 (2H, q, J=7.1 Hz), 4.78 (2H, d, J=2.4 Hz), 6.16 (1H, br s), 7.00 (2H, s)

PRODUCTION EXAMPLE 78

Step 1
A mixture of 1.45 g of 7-azabicyclo[4.1.0]heptane, 2 ml of triethylamine and 3 ml of ethyl acetate was added dropwise to a mixture of 10 ml of ethyl acetate and 2.3 g of 3,5-difluoro-4-(2-propynyloxy)benzoic acid chloride under ice-cooling. The resulting mixture was stirred at room temperature for 4 hours. The reaction mixture was concentrated under reduced pressure. The residue was subjected to silica gel column chromatography to obtain 1.8 g of 7-[3,5-difluoro-4-(2-propynyloxy)benzoyl]-7-azabicyclo[4.1.0]heptane represented by the formula:

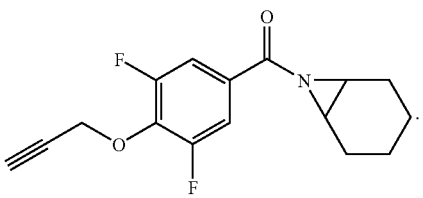

7-[3,5-Difluoro-4-(2-propynyloxy)benzoyl]-7-azabicyclo[4.1.0]heptane $^1$H-NMR (CDCl$_3$) δ: 1.33-1.41 (2H, m), 1.51-1.60 (2H, m), 1.89-1.96 (2H, m), 2.02-2.09 (2H, m), 2.53 (1H, t, J=2.4 Hz), 2.78 (2H, t, J=1.7 Hz), 4.90 (2H, d, J=2.4 Hz), 7.52-7.59 (2H, m)

Step 2
At room temperature, 99 mg of trimethylsilyl cyanide was added dropwise to a mixture of 12 ml of tetrahydrofuran and 291 mg of 7-[3,5-difluoro-4-(2-propynyloxy)benzoyl]-7-azabicyclo[4.1.0]heptane and, further, tetrabutylammonium fluoride (0.05 ml of 1M tetrahydrofuran solution) was added. The resulting mixture was heated with stirring at 40° C. for 8 hours. The reaction mixture was concentrated under reduced pressure. The residue was subjected to silica gel column chromatography to obtain 0.24 g of N-(2-cyanocyclohexyl)-3,5-difluoro-4-(2-propynyloxy)benzamide (hereinafter, described as the compound 80 of the present invention) represented by the formula:

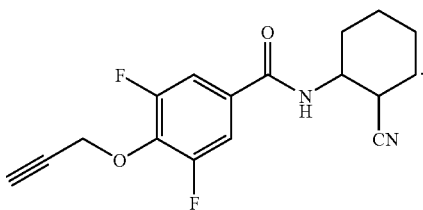

The Compound 80 of the Present Invention:
$^1$H-NMR (CDCl$_3$) δ: 1.26-1.82 (6H, m), 2.08-2.18 (2H, m), 2.53 (1H, t, J=2.3 Hz), 2.76 (1H, td, J=10.5, 3.5 Hz), 4.10-4.18 (1H, m), 4.88 (2H, d, J=2.4 Hz), 6.31 (1H, d, J=8.0 Hz), 7.34-7.41 (2H, m)

PRODUCTION EXAMPLE 79

According to the same method as that of Production Example 1, N-(1-cyclobutyl)ethyl-3,5-difluoro-4-(2-propynyloxy)benzamide (hereinafter, described as the compound 81 of the present invention) represented by the formula:

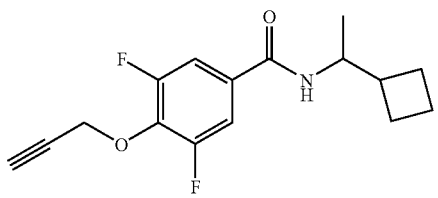

was obtained.
The Compound 81 of the Present Invention:
$^1$H-NMR (CDCl$_3$) δ: 1.12 (3H, d, J=6.5 Hz), 1.72-2.08 (6H, m), 2.31-2.37 (1H, m), 2.52 (1H, t, J=2.4 Hz), 4.08-4.18 (1H, m), 4.87 (2H, d, J=2.4 Hz), 5.87 (1H, d, J=7.7 Hz), 7.31-7.37 (2H, m).

PRODUCTION EXAMPLE 80

According to the same method as that of Production Example 1, N-(2,2,3,3-tetramethylcyclopropyl)methyl-3,5-difluoro-4-(2-propynyloxy)benzamide (hereinafter, described as the compound 82 of the present invention) represented by the formula:

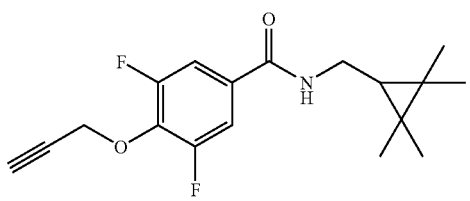

was obtained.
The Compound 82 of the Present Invention:
$^1$H-NMR (CDCl$_3$) δ: 0.50 (1H, t, J=7.7 Hz), 1.04 (6H, s) 1.12 (6H, s), 2.52 (1H, t, J=2.4 Hz), 3.44 (2H, dd, J=7.7, 5.1 Hz), 4.88 (2H, d, J=2.4 Hz), 6.00-6.02 (1H, br m), 7.30-7.37 (2H, m).

PRODUCTION EXAMPLE 81

According to the same method as that of Production Example 1, N-(1-hydroxycyclohexyl)methyl-3,5-dimethoxy-4-(2-propynyloxy)benzamide (hereinafter, described as the compound 83 of the present invention) represented by the formula:

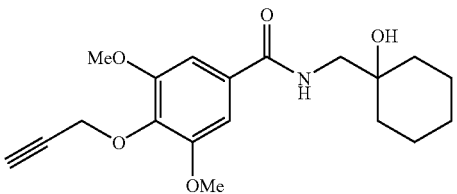

was obtained.
The Compound 83 of the Present Invention:
$^1$H-NMR (CDCl$_3$) δ: 1.25-1.58 (10H, m), 2.45 (1H, t, J=2.4 Hz), 2.75 (1H, br s), 3.46 (2H, d, J=5.9 Hz), 3.86 (6H, s), 4.76 (2H, d, J=2.4 Hz), 6.82 (1H, br s), 7.03 (2H, s).

PRODUCTION EXAMPLE 82

According to the same method as that of Production Example 1, N-(1-hydroxycyclohexyl)methyl-3-methoxy-4-(2-propynyloxy)benzamide (hereinafter, described as the compound 84 of the present invention) represented by the formula:

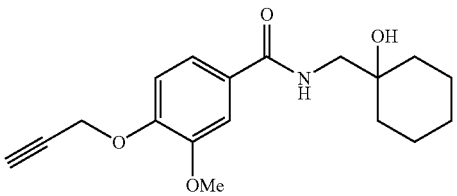

was obtained.
The Compound 84 of the Present Compound:
$^1$H-NMR (CDCl$_3$) δ: 1.24-1.60 (10H, m), 2.56 (1H, t, J=2.4 Hz), 3.06 (1H, br s), 3.45-3.46 (2H, m), 3.85 (3H, s), 4.78 (2H, d, J=2.4 Hz), 6.94-7.00 (2H, m), 7.32 (1H, dd, J=8.4, 2.1 Hz), 7.44 (1H, d, J=2.2 Hz).

PRODUCTION EXAMPLE 83

According to the same method as that of Production Example 1, N-(1-hydroxycyclohexyl)methyl-3-fluoro-5-methoxy-4-(2-propynyloxy)benzamide (hereinafter, described as the compound 85 of the present invention) represented by the formula:

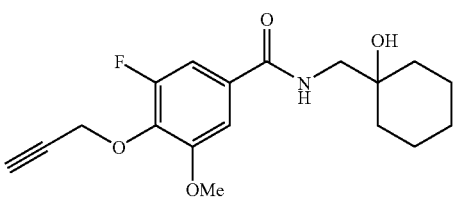

was obtained.

The Compound 85 of the Present Invention:
¹H-NMR (CDCl₃) δ: 1.36-1.60 (10H, m), 2.17 (1H, br s), 2.47 (1H, t, J=2.4 Hz), 3.48 (2H, d, J=5.9 Hz), 3.92 (3H, s), 4.83 (2H, d, J=2.4 Hz), 6.55 (1H, br s), 7.10 (1H, dd, J=10.4, 1.8 Hz), 7.25-7.27 (1H, m).

PRODUCTION EXAMPLE 84

According to the same method as that of Production Example 1, N-(1-hydroxycyclohexyl)methyl-3-fluoro-4-(2-propynyloxy)benzamide (hereinafter, described as the compound 86 of the present invention) represented by the formula:

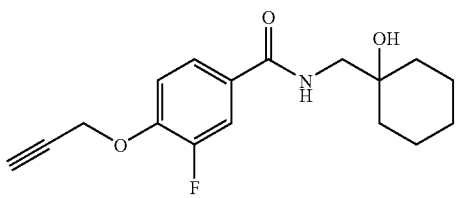

was obtained.
The Compound 86 of the Present Invention:
¹H-NMR (CDCl₃) δ: 1.33-1.55 (10H, m), 2.04 (1H, br s), 2.57 (1H, t, J=2.4 Hz), 3.47 (2H, d, J=5.9 Hz), 4.81 (2H, d, J=2.4 Hz), 6.58 (1H, br s), 7.10-7.14 (1H, m), 7.54-7.60 (2H, m).

PRODUCTION EXAMPLE 85

A mixture of 4 ml of chloroform and 298 mg of zinc (II) chloride was stirred at 60° C. After 5 minutes, a mixture of 291 mg of 7-[3,5-difluoro-4-(2-propynyloxy)benzoyl]-7-azabicyclo[4.1.0]heptane and 2 ml of chloroform was added dropwise thereto at 60° C., and the resulting mixture was heated under reflux for 5 hours. Then, an aqueous saturated ammonium chloride solution was added to the reaction mixture, and this was extracted with chloroform. The organic layer was dried over magnesium sulfate, and concentrated under reduced pressure. The residue was subjected to silica gel column chromatography to obtain 0.22 g of N-(2-chlorocyclohexyl)-3,5-difluoro-4-(2-propynyloxy)benzamide (hereinafter, described as the compound 87 of the present invention) represented by the formula:

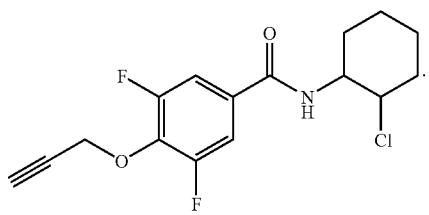

The Compound 87 of the Present Invention:
¹H-NMR (CDCl₃) δ: 1.26-1.53 (3H, m), 1.75-1.86 (3H, m), 2.27-2.34 (2H, m), 2.52 (1H, t, J=2.4 Hz), 3.84 (1H, td, J=10.5, 4.1 Hz), 3.97-4.05 (1H, m), 4.88 (2H, d, J=2.4 Hz), 6.01 (1H, d, J=7.1 Hz), 7.33-7.40 (2H, m).

PRODUCTION EXAMPLE 86

According to the same method as that of Production Example 1, N-(1-cyclobutyl)ethyl-3,5-dimethoxy-4-(2-propynyloxy)benzamide (hereinafter, described as the compound 88 of the present invention) represented by the formula:

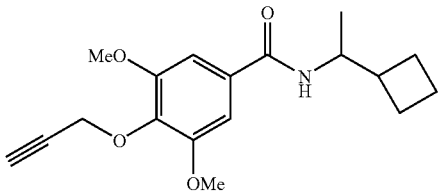

was obtained.
The Compound 88 of the Present Invention:
¹H-NMR (CDCl₃) δ: 1.14 (3H, d, J=6.5 Hz), 1.75-1.92 (4H, m), 1.97-2.10 (2H, m), 2.31-2.39 (1H, m), 2.43 (1H, t, J=2.4 Hz), 3.91 (6H, s), 4.11-4.21 (1H, m), 4.77 (2H, d, J=2.4 Hz), 5.71 (1H, d, J=8.9 Hz), 6.96 (2H, s).

PRODUCTION EXAMPLE 87

According to the same method as that of Production Example 1, N-(1-cyclobutyl)ethyl-3-methoxy-4-(2-propynyloxy)benzamide (hereinafter, described as the compound 89 of the present invention) represented by the formula:

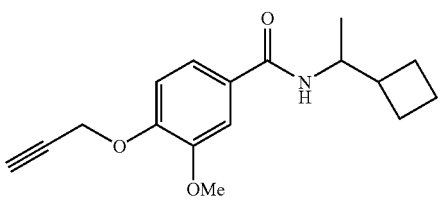

was obtained.
The Compound 89 of the Present Invention:
¹H-NMR (CDCl₃) δ: 1.13 (3H, d, J=6.8 Hz), 1.77-1.90 (4H, m), 1.99-2.08 (2H, m), 2.30-2.40 (1H, m), 2.52 (1H, t, J=2.3 Hz), 3.94 (3H, s), 4.11-4.21 (1H, m), 4.81 (2H, d, J=2.4 Hz), 5.75 (1H, d, J=8.2 Hz), 7.02 (1H, d, J=8.2 Hz), 7.21 (1H, dd, J=8.3, 2.1 Hz), 7.45 (1H, d, J=1.9 Hz)

PRODUCTION EXAMPLE 88

According to the same method as that of Production Example 1, N-(1-cyclopentyl)methyl-3-fluoro-4-(2-propynyloxy)benzamide (hereinafter, described as the compound 90 of the present invention) represented by the formula:

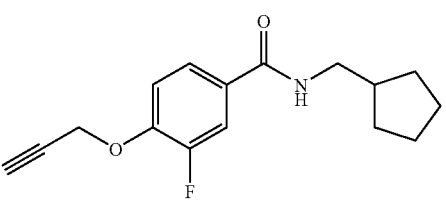

was obtained.

The Compound 90 of the Present Invention:

$^1$H-NMR (CDCl$_3$) δ: 1.23-1.85 (8H, m), 2.10-2.17 (1H, m), 2.56 (1H, t, J=2.3 Hz), 3.38 (2H, dd, J=7.2, 5.8 Hz), 4.82 (2H, d, J=2.4 Hz), 6.05 (1H, br s), 7.11-7.15 (1H, m), 7.49-7.56 (2H, m)

PRODUCTION EXAMPLE 89

According to the same method as that of Production Example 1, N-(1-cyclopentyl)methyl-3-fluoro-5-methoxy-4-(2-propynyloxy)benzamide (hereinafter, described as the compound 91 of the present invention) represented by the formula:

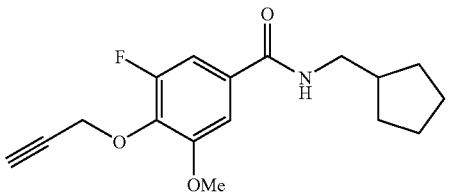

was obtained.

The Compound 91 of the Present Invention:

$^1$H-NMR (CDCl$_3$) δ: 1.24-1.85 (8H, m), 2.11-2.21 (1H, m), 2.47 (1H, t, J=2.3 Hz), 3.38 (2H, dd, J=7.2, 5.8 Hz), 3.93 (3H, s), 4.83 (2H, d, J=2.4 Hz), 6.08 (1H, br s), 7.04 (1H, dd, J=10.1, 1.9 Hz), 7.24-7.25 (1H, m).

PRODUCTION EXAMPLE 90

According to the same method as that of Production Example 1, N-(1-cyclobutyl)methyl-3,5-dimethoxy-4-(2-propynyloxy)benzamide (hereinafter, described as the compound 92 of the present invention) represented by the formula:

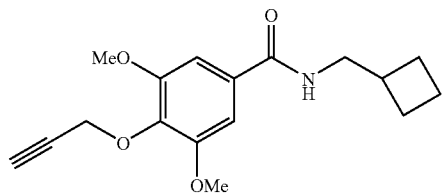

was obtained.

The Compound 92 of the Present Invention:

$^1$H-NMR (CDCl$_3$) δ: 1.69-1.78 (2H, m), 1.86-1.94 (2H, m), 2.03-2.11 (2H, m), 2.44 (1H, t, J=2.4 Hz), 2.53-2.61 (1H, m), 3.44 (2H, t, J=6.5 Hz), 3.85 (6H, s), 4.74-4.75 (2H, m), 6.55 (1H, br s), 7.02 (2H, s).

PRODUCTION EXAMPLE 91

According to the same method as that of Production Example 1, N-(1-cyclobutyl)methyl-3-fluoro-4-(2-propynyloxy)benzamide (hereinafter, described as the compound 93 of the present invention) represented by the formula:

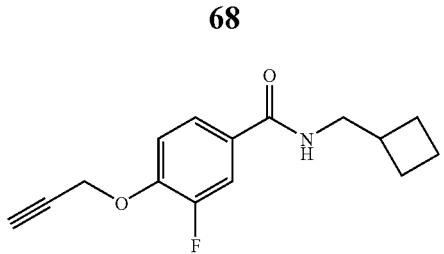

was obtained.

The Compound 93 of the Present Invention:

$^1$H-NMR (CDCl$_3$) δ: 1.69-1.78 (2H, m), 1.86-1.96 (2H, m), 2.04-2.13 (2H, m), 2.53-2.61 (2H, m), 3.45 (2H, dd, J=7.1, 5.9 Hz), 4.80 (2H, d, J=2.4 Hz), 6.25 (1H, br s), 7.09-7.13 (1H, m), 7.51-7.57 (2H, m).

PRODUCTION EXAMPLE 92

According to the same method as that of Production Example 1, N-(1-cyclobutyl)methyl-3-fluoro-5-methoxy-4-(2-propynyloxy)benzamide (hereinafter, described as the compound 94 of the present invention) represented by the formula:

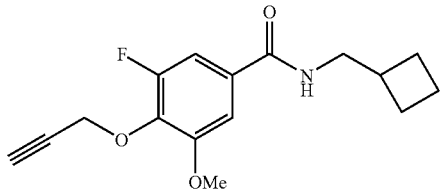

was obtained.

The Compound 94 of the Present Invention:

$^1$H-NMR (CDCl$_3$) δ: 1.69-1.79 (2H, m), 1.85-1.97 (2H, m), 2.06-2.13 (2H, m), 2.47 (1H, t, J=2.4 Hz), 2.51-2.61 (1H, m), 3.45 (2H, dd, J=7.2, 5.8 Hz), 3.91 (3H, s), 4.82 (2H, d, J=2.4 Hz), 6.26 (1H, br s), 7.06 (1H, dd, J=10.4, 1.9 Hz), 7.24 (1H, dd, J=1.9, 1.7 Hz).

PRODUCTION EXAMPLE 93

According to the same method as that of Production Example 1, N-(1-cyclobutyl)ethyl-3-fluoro-4-(2-propynyloxy)benzamide (hereinafter, described as the compound 95 of the present invention) represented by the formula:

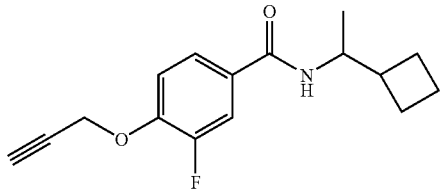

was obtained.

The Compound 95 of the Present Invention:

$^1$H-NMR (CDCl$_3$) δ: 1.12 (3H, d, J=6.5 Hz), 1.73-1.92 (4H, m), 1.97-2.08 (2H, m), 2.29-2.39 (1H, m), 2.56 (1H, t,

J=2.4 Hz), 4.10-4.19 (1H, m), 4.81 (2H, d, J=2.4 Hz), 5.76 (1H, d, J=7.7 Hz), 7.10-7.14 (1H, m), 7.48-7.55 (2H, m).

PRODUCTION EXAMPLE 94

According to the same method as that of Production Example 1, N-(1-cyclobutyl)ethyl-3-fluoro-5-methoxy-4-(2-propynyloxy)benzamide (hereinafter, described as the compound 96 of the present invention) represented by the formula:

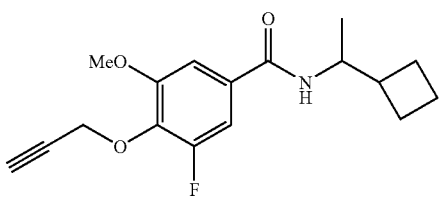

was obtained.

The Compound 96 of the Present Invention:
¹H-NMR (CDCl₃) δ: 1.12 (3H, d, J=6.8 Hz), 1.75-1.90 (4H, m), 1.99-2.08 (2H, m), 2.31-2.38 (1H, m), 2.47 (1H, t, J=2.4 Hz), 3.91 (3H, s), 4.09-4.19 (1H, m), 4.82 (2H, d, J=2.4 Hz), 5.92 (1H, d, J=8.0 Hz), 7.04 (1H, dd, J=10.4, 1.9 Hz), 7.24-7.25 (1H, m).

PRODUCTION EXAMPLE 95

According to the same method as that of Production Example 1, N-(1-cyclopropyl)methyl-3,5-dimethoxy-4-(2-propynyloxy)benzamide (hereinafter, described as the compound 97 of the present invention) represented by the formula:

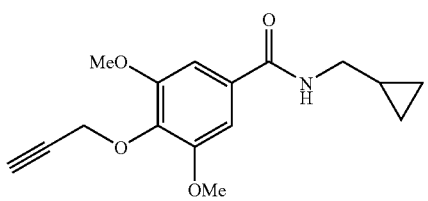

was obtained.

The Compound 97 of the Present Invention:
¹H-NMR (CDCl₃) δ: 0.24-0.28 (2H, m), 0.50-0.56 (2H, m), 1.02-1.12 (1H, m), 2.44-2.46 (1H, m), 3.26-3.30 (2H, m), 3.87-3.87 (6H, m), 4.75 (2H, d, J=2.4 Hz), 6.63 (1H, br s), 7.05 (2H, s).

PRODUCTION EXAMPLE 96

According to the same method as that of Production Example 1, N-(1-cyclopropyl)methyl-3-fluoro-4-(2-propynyloxy)benzamide (hereinafter, described as the compound 98 of the present invention) represented by the formula:

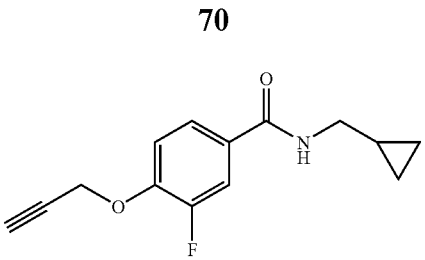

was obtained.

The Compound 98 of the Present Invention:
¹H-NMR (CDCl₃) δ: 0.25-0.29 (2H, m), 0.54-0.58 (2H, m), 1.03-1.07 (1H, m), 2.56 (1H, t, J=2.4 Hz), 3.30 (2H, dd, J=7.2, 5.3 Hz), 4.82 (2H, d, J=2.4 Hz), 6.16 (1H, br s), 7.11-7.16 (1H, m), 7.53-7.59 (2H, m).

PRODUCTION EXAMPLE 97

According to the same method as that of Production Example 1, N-(2-chlorocyclohexyl)-3,5-difluoro-4-(2-propynyloxy)benzamide (hereinafter, described as the compound 99 of the present invention) represented by the formula:

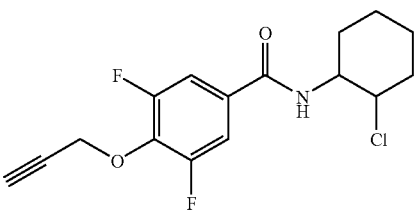

was obtained.

The Compound 99 of the Present Invention:
¹H-NMR (CDCl₃) δ: 1.37-1.58 (2H, m), 1.67-1.95 (5H, m), 2.11-2.17 (1H, m), 2.52 (1H, t, J=2.4 Hz), 4.24-4.31 (1H, m), 4.55-4.57 (1H, m), 4.88 (2H, d, J=2.4 Hz), 6.23 (1H, d, J=8.2 Hz), 7.32-7.39 (2H, m).

PRODUCTION EXAMPLE 98

According to the same method as that of Production Example 1, N-(2-hydroxycyclohexyl)-3,5-difluoro-4-(2-propynyloxy)benzamide (hereinafter, described as the compound 100 of the present invention) represented by the formula:

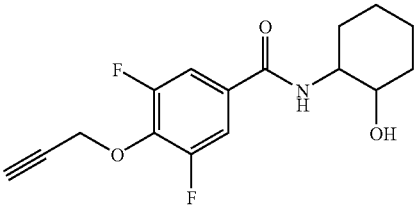

was obtained.

The Compound 100 of the Present Invention:
¹H-NMR (CDCl₃) δ: 1.26-1.44 (4H, m), 1.74-1.80 (2H, m), 2.09-2.13 (2H, m), 2.51 (1H, t, J=2.4 Hz), 3.43 (1H, dt, J=14.6, 5.3 Hz), 3.77-3.86 (1H, m), 4.88 (2H, d, J=2.4 Hz), 6.05 (1H, d, J=6.5 Hz), 7.34-7.40 (2H, m)

PRODUCTION EXAMPLE 99

According to the same method as that of Production Example 1, N-(1-cyclopentyl)ethyl-3-fluoro-4-(2-propynyloxy)benzamide (hereinafter, described as the compound 101 of the present invention) represented by the formula:

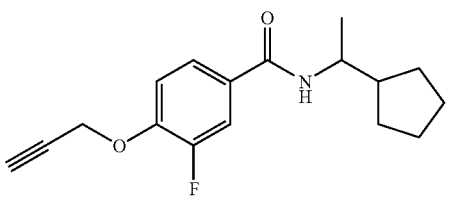

was obtained.
The Compound 101 of the Present Invention:
$^1$H-NMR (CDCl$_3$) δ: 1.21-1.95 (9H, m), 1.22 (3H, d, J=6.5 Hz), 2.55-2.57 (1H, m), 3.99-4.12 (1H, m), 4.81-4.82 (2H, m), 5.89-5.91 (1H, br m), 7.09-7.16 (1H, m), 7.48-7.56 (2H, m).

PRODUCTION EXAMPLE 100

According to the same method as that of Production Example 1, N-(1-cyclopentyl)ethyl-3-fluoro-5-methoxy-4-(2-propynyloxy)benzamide (hereinafter, described as the compound 102 of the present invention) represented by the formula:

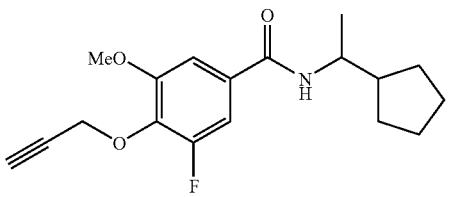

was obtained.
The Compound 102 of the Present Invention:
$^1$H-NMR (CDCl$_3$) δ: 1.22-1.96 (9H, m), 1.23 (3H, d, J=6.8 Hz), 2.47 (1H, t, J=2.4 Hz), 3.93 (3H, s), 4.02-4.13 (1H, m), 4.82 (2H, d, J=2.4 Hz), 5.88-5.90 (1H, br m), 7.02 (1H, dd, J=10.4, 1.8 Hz), 7.25 (1H, dd, J=1.8, 1.8 Hz).

PRODUCTION EXAMPLE 101

According to the same method as that of Production Example 1, N-(1-cyclopentyl)ethyl-3-methoxy-4-(2-propynyloxy)benzamide (hereinafter, described as the compound 103 of the present invention) represented by the formula:

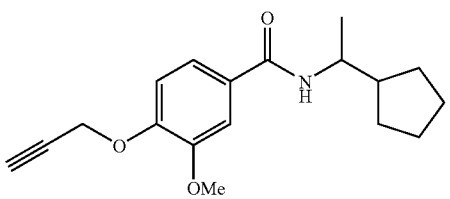

was obtained.
The Compound 103 of the Present Invention:
$^1$H-NMR (CDCl$_3$) δ: 1.23 (3H, d, J=6.5 Hz), 1.23-1.41 (2H, m), 1.47-1.99 (7H, m), 2.52 (1H, t, J=2.4 Hz), 3.93 (3H, s), 4.02-4.13 (1H, m), 4.81 (2H, d, J=2.4 Hz), 5.88-5.90 (1H, br m), 7.02 (1H, d, J=8.4 Hz), 7.21 (1H, dd, J=8.4, 2.0 Hz), 7.46 (1H, d, J=2.0 Hz)

PRODUCTION EXAMPLE 102

According to the same method as that of Production Example 1, N-(1-cyclopentyl)ethyl-3,5-dimethoxy-4-(2-propynyloxy)benzamide (hereinafter, described as the compound 104 of the present invention) represented by the formula:

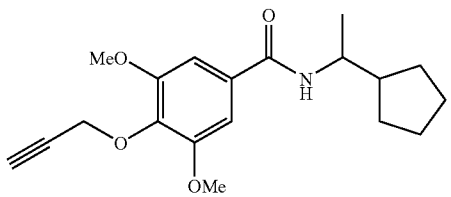

was obtained.
The Compound 104 of the Present Invention:
$^1$H-NMR (CDCl$_3$) δ: 1.22-1.42 (2H, m), 1.24 (3H, d, J=6.5 Hz), 1.50-2.01 (7H, m), 2.43 (1H, t, J=2.4 Hz), 3.91 (6H, s), 4.01-4.12 (1H, m), 4.77 (2H, d, J=2.4 Hz), 5.87-5.89 (1H, br m), 6.96 (2H, s).

PRODUCTION EXAMPLE 103

According to the same method as that of Production Example 1, N-(1-cyclopropyl)ethyl-3-methoxy-4-(2-propynyloxy)benzamide (hereinafter, described as the compound 105 of the present invention) represented by the formula:

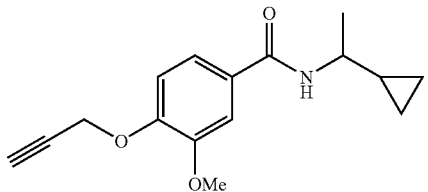

was obtained.
The Compound 105 of the Present Invention:
$^1$H-NMR (CDCl$_3$) δ: 0.26-0.31 (1H, m), 0.37-0.58 (3H, m), 0.87-0.95 (1H, m), 1.30 (3H, d, J=6.6 Hz), 2.53 (1H, t, J=2.3 Hz), 3.53-3.62 (1H, m), 3.91 (3H, s), 4.80 (2H, d, J=2.4 Hz), 6.22 (1H, d, J=7.3 Hz), 7.01 (1H, d, J=8.3 Hz), 7.26-7.29 (1H, m), 7.46 (1H, d, J=2.2 Hz).

PRODUCTION EXAMPLE 104

According to the same method as that of Production Example 1, N-(1-cyclopropyl)ethyl-3,5-dimethoxy-4-(2-propynyloxy)benzamide (hereinafter, described as the compound 106 of the present invention) represented by the formula:

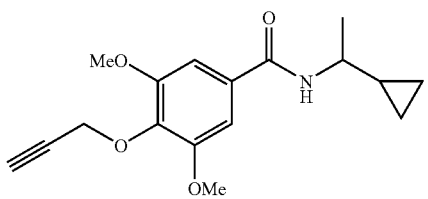

was obtained.
The Compound 106 of the Present Invention:
$^1$H-NMR (CDCl$_3$) δ: 0.27-0.33 (1H, m), 0.38-0.60 (3H, m), 0.88-0.97 (1H, m), 1.32 (3H, d, J=6.6 Hz), 2.43 (1H, t, J=2.4 Hz), 3.51-3.61 (1H, m), 3.91 (6H, s), 4.77 (2H, d, J=2.4 Hz), 6.07 (1H, d, J=5.9 Hz), 6.99 (2H, s)

PRODUCTION EXAMPLE 105

According to the same method as that of Production Example 1, N-(1-cyclopropyl)ethyl-3-fluoro-4-(2-propynyloxy)benzamide (hereinafter, described as the compound 107 of the present invention) represented by the formula:

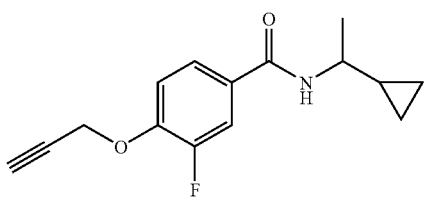

was obtained.
The Compound 107 of the Present Invention:
$^1$H-NMR (CDCl$_3$) δ: 0.25-0.31 (1H, m), 0.36-0.58 (3H, m), 0.86-0.95 (1H, m), 1.29 (3H, d, J=6.5 Hz), 2.57 (1H, t, J=2.4 Hz), 3.51-3.60 (1H, m), 4.81 (2H, t, J=2.8 Hz), 6.19 (1H, d, J=7.2 Hz), 7.09-7.14 (1H, m), 7.52-7.58 (2H, m).

PRODUCTION EXAMPLE 106

Step 1
According to the same method as that of Production Example 78, Step 1,3-methoxy-4-(2-propynyloxy)benzoic acid chloride was used in place of 3,5-difluoro-4-(2-propynyloxy)benzoic acid chloride to obtain 7-[3-methoxy-4-(2-propynyloxy)benzoyl]-7-azabicyclo[4.1.0]heptane represented by the formula:

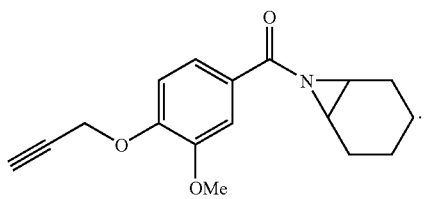

7-[3-Methoxy-4-(2-propynyloxy)benzoyl]-7-azabicyclo[4.1.0]heptane $^1$H-NMR (CDCl$_3$) δ: 1.31-1.40 (2H, m), 1.52-1.61 (2H, m), 1.89-1.96 (2H, m), 2.03-2.10 (2H, m), 2.56 (1H, t, J=2.4 Hz), 2.75-2.76 (2H, m), 3.93 (3H, s), 4.83 (2H, d, J=2.4 Hz), 7.06 (1H, d, J=8.5 Hz), 7.55 (1H, d, J=2.0 Hz), 7.63 (1H, dd, J=8.3, 2.0 Hz).

Step 2
A mixture of 2 ml of chloroform and 224 mg of zinc (II) chloride was stirred at room temperature for 5 minutes. Then, a mixture of 235 mg of 7-[3-methoxy-4-(2-propynyloxy)benzoyl]-7-azabicyclo[4.1.0]heptane and 2 ml of chloroform was added dropwise thereto at room temperature, and the resulting mixture was stirred at room temperature for 5 hours. Then, an aqueous saturated ammonium chloride solution was added to the reaction mixture, and this was extracted with chloroform. The organic layer was dried over magnesium sulfate, and concentrated under reduced pressure. The residue was washed with hexane to obtain 0.25 g of N-(2-chlorocyclohexyl)-3-methoxy-4-(2-propynyloxy)benzamide (hereinafter, described as the compound 108 of the present invention) represented by the formula:

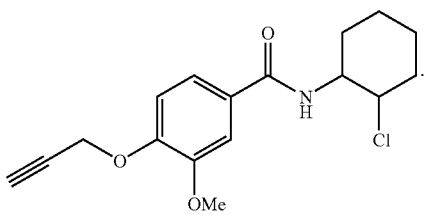

The Compound 108 of the Present Invention:
$^1$H-NMR (CDCl$_3$) δ: 1.33-1.49 (3H, m), 1.75-1.84 (3H, m), 2.29-2.32 (2H, m), 2.53 (1H, t, J=2.3 Hz), 3.84-3.95 (4H, m), 4.00-4.10 (1H, m), 4.81 (2H, d, J=2.4 Hz), 6.22 (1H, d, J=7.8 Hz), 7.02 (1H, d, J=8.3 Hz), 7.27-7.30 (1H, m), 7.46 (1H, d, J=2.0 Hz)

PRODUCTION EXAMPLE 107

Step 1
According to the same method as that of Production Example 78, Step 1, 3,5-dimethoxy-4-(2-propynyloxy)benzoic acid chloride was used in place of 3,5-difluoro-4-(2-propynyloxy)benzoic acid chloride to obtain 7-[3,5-dimethoxy-4-(2-propynyloxdy)benzoyl]-7-azabicyclo[4.1.0]heptane represented by the formula:

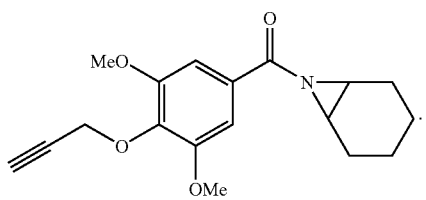

7-[3,5-Dimethoxy-4-(2-propynyloxdy)benzoyl]-7-azabicyclo[4.1.0]heptane $^1$H-NMR (CDCl$_3$) δ: 1.32-1.41 (2H, m), 1.52-1.61 (2H, m), 1.91-1.98 (2H, m), 2.02-2.09 (2H, m), 2.48 (1H, t, J=2.4 Hz), 2.75-2.79 (2H, m), 3.91 (6H, s), 4.79 (2H, d, J=2.4 Hz), 7.27 (2H, s)

Step 2
A mixture of 2 ml of chloroform and 258 mg of zinc (II) chloride was stirred at room temperature for 5 minutes.

Thereafter, a mixture of 300 mg of 7-[3,5-dimethoxy-4-(2-propynyloxy)benzoyl]-7-azabicyclo[4.1.0]heptane and 2 ml of chloroform was added dropwise thereto at room temperature, and the resulting mixture was stirred at room temperature for 5 hours. Then, an aqueous saturated ammonium chloride solution was added to the reaction mixture, and this was extracted with chloroform. The organic layer was dried over magnesium sulfate, and concentrated under reduced pressure. The residue was subjected to silica gel column chromatography to obtain 0.16 g of N-(2-chlorocyclohexyl)-3,5-dimethoxy-4-(2-propynyloxy)benzamide (hereinafter, described as the compound 109 of the present invention) represented by the formula:

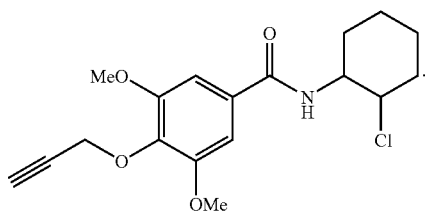

The Compound 109 of the Present Invention:
¹H-NMR (CDCl₃) δ: 1.24-1.45 (3H, m), 1.72-1.80 (3H, m), 2.17-2.31 (2H, m), 2.44 (1H, t, J=2.4 Hz), 3.86-3.92 (7H, m), 3.99-4.12 (1H, m), 4.76 (2H, d, J=2.4 Hz), 6.52 (1H, d, J=8.0 Hz), 7.04 (2H, s).

PRODUCTION EXAMPLE 108

Step 1
According to the same method as that of Production Example 78, Step 1,3-fluoro-4-(2-propynyloxy)benzoic acid chloride was used in place of 3,5-difluoro-4-(2-propynyloxy) benzoic acid chloride to obtain 7-[3-fluoro-4-(2-propynyloxy)benzoyl]-azabicyclo[4.1.0]heptane represented by the formula:

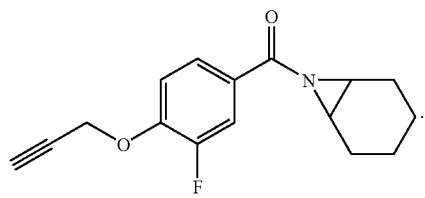

7-[3-Fluoro-4-(2-propynyloxy)benzoyl]-azabicyclo [4.1.0]heptane

¹H-NMR (CDCl₃) δ: 1.31-1.40 (2H, m), 1.51-1.60 (2H, m), 1.88-1.95 (2H, m), 2.02-2.09 (2H, m), 2.60 (1H, t, J=2.4 Hz), 2.75-2.76 (2H, m), 4.83 (2H, t, J=1.7 Hz), 7.12-7.17 (1H, m), 7.70-7.78 (2H, m).
Step 2
A mixture of 2 ml of chloroform and 229 mg of zinc (II) chloride was stirred at room temperature for 5 minutes. Then, a mixture of 230 mg of 7-[3-fluoro-4-(2-propynyloxy)benzoyl]-7-azabicyclo[4.1.0]heptane and 2 ml of chloroform was added dropwise thereto at room temperature, and the resulting mixture was stirred at room temperature for 5 hours. Then, an aqueous saturated ammonium chloride solution was added to the reaction mixture, and this was extracted with chloroform. The organic layer was dried over magnesium sulfate, and concentrated under reduced pressure. The residue was washed with hexane to obtain 0.20 g of N-(2-chlorocyclohexyl)-3-fluoro-4-(2-propynyloxy)benzamide (hereinafter, described as the compound 110 of the present invention) represented by the formula:

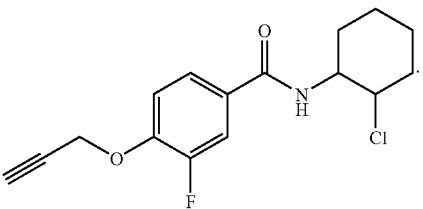

The Compound 110 of the Present Invention:
¹H-NMR (CDCl₃) δ: 1.25-1.53 (3H, m), 1.72-1.85 (3H, m), 2.28-2.34 (2H, m), 2.56 (1H, t, J=2.4 Hz), 3.86 (1H, td, J=10.5, 4.1 Hz), 3.98-4.06 (1H, m), 4.82 (2H, d, J=2.4 Hz), 6.10 (1H, d, J=7.3 Hz), 7.11-7.15 (1H, m), 7.52-7.58 (2H, m).

PRODUCTION EXAMPLE 109

According to the same method as that of Production Example 1, N-(2-hydroxycyclopentyl)-3,5-difluoro-4-(2-propynyloxy)benzamide (hereinafter, described as the compound 111 of the present invention) represented by the formula:

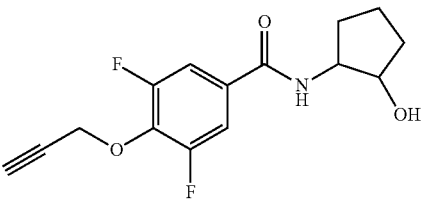

was obtained.
The Compound III of the Present Invention:
¹H-NMR (CDCl₃) δ: 1.49-1.58 (1H, m), 1.68-1.92 (3H, m), 2.03-2.12 (1H, m), 2.22-2.30 (1H, m), 2.52 (1H, t, J=2.4 Hz), 3.97-4.10 (2H, m), 4.15 (1H, br s), 4.89 (2H, d, J=2.4 Hz), 6.17 (1H, br s), 7.33-7.39 (2H, m)

PRODUCTION EXAMPLE 110

A mixture of 2 ml of chloroform and 450 mg of zinc (II) bromide was stirred at room temperature for 5 minutes. Then, a mixture of 291 mg of 7-[3,5-difluoro-4-(2-propynyloxy) benzoyl]-7-azabicyclo[4.1.0]heptane and 2 ml of chloroform was added dropwise thereto at room temperature, and the resulting mixture was stirred at room temperature for 12 hours. Then, an aqueous saturated ammonium chloride solution was added to the reaction mixture, and this was extracted with chloroform. The organic layer was dried over magnesium sulfate, and concentrated under reduced pressure. The residue was subjected to silica gel column chromatography. The resulting solid was washed with hexane to obtain 0.30 g of N-(2-bromocyclohexyl)-3,5-difluoro-4-(2-propynyloxy) benzamide (hereinafter, described as the compound 112 of the present invention) represented by the formula:

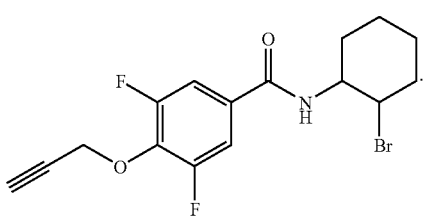
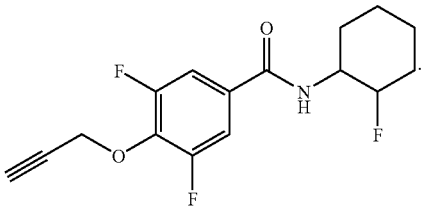

The Compound 112 of the Present Invention:

$^1$H-NMR (CDCl$_3$) δ: 1.24-1.53 (3H, m), 1.76-1.83 (2H, m), 1.92-2.02 (1H, m), 2.30-2.36 (1H, m), 2.42-2.48 (1H, m), 2.52 (1H, t, J=2.4 Hz), 3.98 (1H, td, J=10.7, 4.1 Hz), 4.04-4.11 (1H, m), 4.88 (2H, d, J=2.4 Hz), 6.02 (1H, d, J=7.7 Hz), 7.34-7.40 (2H, m).

The Compound 114 of the Present Invention:

$^1$H-NMR (CDCl$_3$) δ: 1.22-1.46 (3H, m), 1.56-1.73 (2H, m), 1.81-1.87 (1H, m), 2.15-2.25 (2H, m), 2.51 (1H, t, J=2.4 Hz), 4.02-4.15 (1H, m), 4.37 (1H, dtd, J=50.6, 10.0, 4.6 Hz), 4.88 (2H, d, J=2.4 Hz), 6.04 (1H, d, J=7.3 Hz), 7.33-7.40 (2H, m).

PRODUCTION EXAMPLE 113

According to the same method as that of Production Example 1, N-(1-(1-hydroxycyclohexyl)ethyl)-3-methoxy-4-(2-propynyloxy)benzamide (hereinafter, described as the compound 115 of the present invention) represented by the formula:

PRODUCTION EXAMPLE 111

According to the same method as that of Production Example 110 except that zinc (II) iodide was used in place of zinc (II) bromide, 0.40 g of N-(2-iodocyclohexyl)-3,5-difluoro-4-(2-propynyloxy)benzamide (hereinafter, described as the compound 113 of the present invention) represented by the formula:

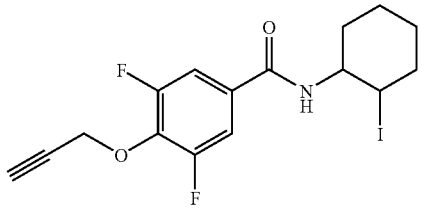

was obtained.

The Compound 113 of the Present Invention:

$^1$H-NMR (CDCl$_3$) δ: 1.26-1.65 (4H, m), 1.85-1.93 (1H, m), 2.11-2.29 (2H, m), 2.50-2.60 (2H, m), 4.06-4.16 (2H, m), 4.88 (2H, d, J=2.4 Hz), 6.05 (1H, br s), 7.35-7.42 (2H, m).

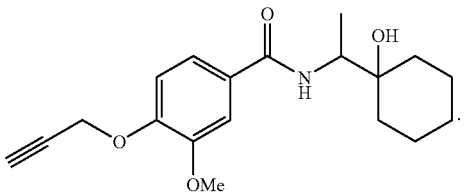

The Compound 115 of the Present Invention $^1$H-NMR (CDCl$_3$) δ: 1.22 (3H, d, J=7.0 Hz), 1.24-1.69 (11H, m), 2.52 (1H, t, J=2.4 Hz), 3.93 (3H, s), 4.19 (1H, dt, J=15.7, 7.0 Hz), 4.81 (2H, d, J=2.4 Hz), 6.45-6.47 (1H, br m), 7.02 (1H, d, J=8.4 Hz), 7.27 (1H, dd, J=8.4, 2.2 Hz), 7.48 (1H, d, J=2.2 Hz).

PRODUCTION EXAMPLE 114

According to the same method as that of Production Example 1, N-(1-(1-hydroxycyclohexyl)ethyl)-3,5-dimethoxy-4-(2-propynyloxy)benzamide (hereinafter, described as the compound 116 of the present invention) represented by the formula:

PRODUCTION EXAMPLE 112

At room temperature, 1.2 ml of tetrabutylammonium fluoride (1M tetrahydrofuran solution) was added dropwise to a mixture of 4 ml of tetrahydrofuran and 291 mg of 7-[3,5-difluoro-4-(2-propynyloxy)benzoyl]-7-azabicyclo[4.1.0]heptane. This mixture was stirred at room temperature for 1 hour. Then, an aqueous saturated ammonium chloride solution was added to the reaction mixture, and this was extracted with ethyl acetate. The organic layer was dried over magnesium sulfate, and concentrated under reduced pressure. The residue was subjected to silica gel column chromatography to obtain 0.13 g of N-(2-fluorocyclohexyl)-3,5-difluoro-4-(2-propynyloxy)benzamide (hereinafter, described as the compound 114 of the present invention) represented by the formula:

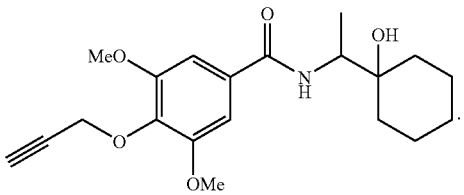

The Compound 116 of the Present Invention $^1$H-NMR (CDCl$_3$) δ: 1.23 (3H, d, J=6.8 Hz), 1.24-1.38 (1H, m), 1.43-1.72 (10H, m), 2.43 (1H, t, J=2.4 Hz), 3.91 (6H, s), 4.14-4.24 (1H, m), 4.77 (2H, d, J=2.4 Hz), 6.45-6.48 (1H, br m), 7.01 (2H, s).

PRODUCTION EXAMPLE 115

According to the same method as that of Production Example 1, N-(1-(1-hydroxycyclohexyl)ethyl)-3-fluoro-4-(2-propynyloxy)benzamide (hereinafter, described as the compound 117 of the present invention) represented by the formula:

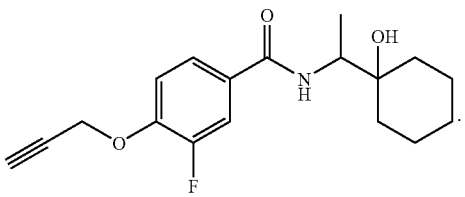

The Compound 117 of the Present Invention $^1$H-NMR (CDCl$_3$) δ: 1.21 (3H, d, J=6.8 Hz), 1.22-1.38 (1H, m), 1.42-1.76 (10H, m), 2.56 (1H, t, J=2.3 Hz), 4.13-4.22 (1H, m), 4.82 (2H, d, J=2.3 Hz), 6.41-6.43 (1H, br m), 7.12 (1H, t, J=8.3 Hz), 7.51-7.60 (2H, m).

PRODUCTION EXAMPLE 116

According to the same method as that of Production Example 1, N-(1-(1-hydroxycyclohexyl)ethyl)-3,5-difluoro-4-(2-propynyloxy)benzamide (hereinafter, described as the compound 118 of the present invention) represented by the formula:

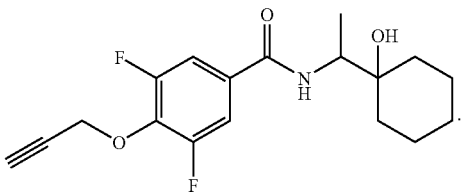

The Compound 118 of the Present Invention $^1$H-NMR (CDCl$_3$) δ: 1.21 (3H, d, J=6.8 Hz), 1.22-1.38 (1H, m), 1.41-1.67 (10H, m), 2.52 (1H, t, J=2.4 Hz), 4.11-4.20 (1H, m), 4.87 (2H, d, J=2.4 Hz), 6.59 (1H, d, J=8.9 Hz), 7.34-7.41 (2H, m).

Then, the production of the intermediates of the compounds of the present invention will be illustrated by Reference Production Examples.

REFERENCE PRODUCTION EXAMPLE 1

To 100 ml of DMF were added 11.8 g of 4-hydroxy-3,5-dimethoxybenzoic acid, 15.7 g of propargyl bromide and 18 g of potassium carbonate, and the mixture obtained was stirred at room temperature for 8 hours and at 80° C. for 4 hours. Then, ethyl acetate was added to the reaction mixture and the mixture was filtered through Celite. Water and dilute hydrochloric acid were added to the filtrate in order and it was extracted with ethyl acetate. The organic layer was dried over magnesium sulfate and concentrated under reduced pressure. The crystals obtained were washed with a mix solvent of hexane and MTBE to obtain 15.5 g of 2-propynyl 4-(2-propynyloxy)-3,5-dimethoxybenzoate represented by the formula:

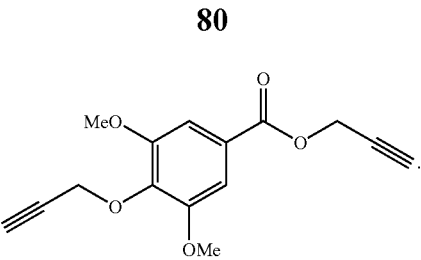

2-Propynyl 4-(2-propynyloxy)-3,5-dimethoxybenzoate $^1$H-NMR (CDCl$_3$) δ: 2.44 (1H, t, J=2.4 Hz), 2.52 (1H, t, J=2.4 Hz), 3.91 (6H, s), 4.81 (2H, d, J=2.4 Hz), 4.92 (2H, d, J=2.4 Hz), 7.33 (2H, s).

To 50 ml of methanol were added 15.5 g of 2-propynyl 4-(2-propynyloxy)-3,5-dimethoxybenzoate and 40 ml of 15% aqueous sodium hydroxide solution and the mixture obtained was stirred at 50° C. for 4 hours. Then, the reaction mixture was added to hydrochloric acid for acidification. Crystals precipitated were collected by filtration and dried to obtain 13.0 g of 4-(2-propynyloxy)-3,5-dimethoxybenzoic acid represented by the formula:

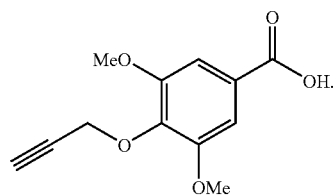

4-(2-Propynyloxy)-3,5-dimethoxybenzoic acid $^1$H-NMR (DMSO-d$_6$) δ: 3.35 (1H, br s), 3.45 (1H, t, J=2.4 Hz), 3.83 (6H, s), 4.70 (2H, d, J=2.4 Hz), 7.24 (2H, s).

To 100 ml of toluene were added 13.0 g of 4-(2-propynyloxy)-3,5-dimethoxybenzoic acid, 9.5 g of thionyl chloride and 50 mg of DMF and the mixture obtained was heated under reflux for 3 hours. Then, the reaction mixture was concentrated. The solid obtained was washed with hexane to obtain 12.0 g of 4-(2-propynyloxy)-3,5-dimethoxybenzoyl chloride represented by the formula:

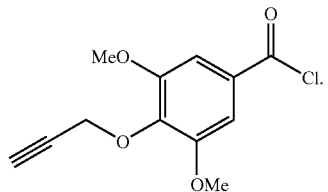

4-(2-Propynyloxy)-3,5-dimethoxybenzoyl chloride $^1$H-NMR (CDCl$_3$) δ: 2.46 (1H, t, J=2.4 Hz), 3.93 (6H, s), 4.87 (2H, d, J=2.4 Hz), 7.38 (2H, s).

REFERENCE PRODUCTION EXAMPLE 2

To 100 ml of DMF were added 10 g of 4-hydroxy-3-methoxybenzoic acid, 15.7 g of propargyl bromide and 18 g of potassium carbonate, and the mixture obtained was stirred at room temperature for 8 hours and at 80° C. for 2 hours. Then, ethyl acetate was added to the reaction mixture and the mixture was filtered through Celite. Water and dilute hydrochloric acid were added to the filtrate in order and it was extracted with ethyl acetate. The organic layer was dried over magnesium sulfate and concentrated under reduced pressure. The crystals obtained were washed with a mix solvent of hexane and MTBE to obtain 13.2 g of 2-propynyl 4-(2-propynyloxy)-3-methoxybenzoate represented by the formula:

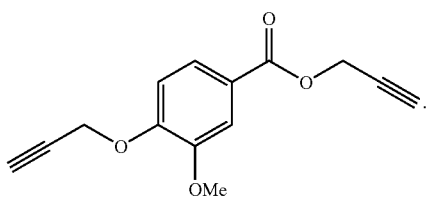

2-Propynyl 4-(2-propynyloxy)-3-methoxybenzoate $^1$H-NMR (CDCl$_3$) δ: 2.52 (1H, t, J=2.5 Hz), 2.55 (1H, t, J=2.4 Hz), 3.93 (3H, s), 4.83 (2H, d, J=2.4 Hz), 4.91 (2H, d, J=2.4 Hz), 7.05 (1H, d, J=8.7 Hz), 7.58 (1H, d, J=1.9 Hz), 7.72 (1H, dd, J=8.5, 1.9 Hz).

To 50 ml of methanol were added 13.2 g of 2-propynyl 4-(2-propynyloxy)-3-methoxybenzoate and 40 ml of 15% aqueous sodium hydroxide solution, and the mixture obtained was stirred at room temperature for 8 hours and at 50° C. for 2 hours. Then, the reaction mixture was added to hydrochloric acid for acidification. Crystals precipitated were collected by filtration and dried to obtain 12.0 g of 4-(2-propynyloxy)-3-methoxybenzoic acid represented by the formula:

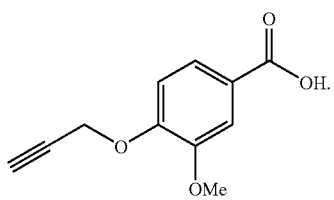

To 100 ml of toluene were added 12.0 g of 4-(2-propynyloxy)-3-methoxybenzoic acid, 9.0 g of thionyl chloride and 50 mg of DMF, and the mixture obtained was heated under reflux for 3 hours. Then, the reaction mixture was concentrated. The solid obtained was washed with hexane to obtain 11.0 g of 4-(2-propynyloxy)-3-methoxybenzoyl chloride represented by the formula.

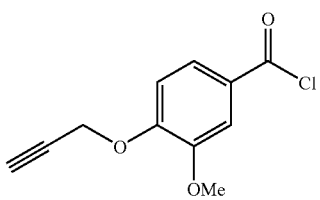

4-(2-Propynyloxy)-3-methoxybenzoyl chloride $^1$H-NMR (CDCl$_3$) δ: 2.59 (1H, t, J=2.4 Hz), 3.94 (3H, s), 4.87 (2H, d, J=2.4 Hz), 7.10 (1H, d, J=8.7 Hz), 7.56 (1H, d, J=2.2 Hz), 7.84 (1H, dd, J=8.7, 2.2 Hz).

REFERENCE PRODUCTION EXAMPLE 3

To 50 ml of DMF were added 5.5 g of 4-hydroxy-3-fluorobenzoic acid, 9.4 g of propargyl bromide and 11 g of potassium carbonate and the mixture was stirred at room temperature for 8 hours. Then, ethyl acetate was added to the reaction mixture and then, the mixture was filtered through Celite. Water and dilute hydrochloric acid were added to the filtrate in order and it was extracted with ethyl acetate. The organic layer was dried over magnesium sulfate and concentrated under reduced pressure. The residue was subjected to silica gel column chromatography to obtain 10.8 g of 2-propynyl 4-(2-propynyloxy)-3-fluorobenzoate represented by the formula:

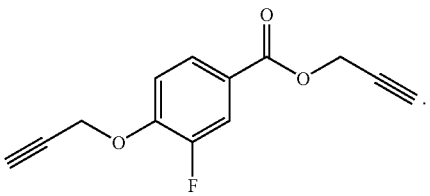

2-Propynyl 4-(2-propynyloxy)-3-fluorobenzoate $^1$H-NMR (CDCl$_3$) δ: 2.50 (1H, t, J=2.5 Hz), 2.56 (1H, t, J=2.4 Hz), 4.82 (2H, d, J=2.4 Hz), 4.89 (2H, d, J=2.4 Hz), 7.13 (1H, t, J=8.3 Hz), 7.78 (1H, dd, J=11.5, 2.1 Hz), 7.82-7.86 (1H, m).

To 50 ml of ethanol were added 10.8 g of 2-propynyl 4-(2-propynyloxy)-3-fluorobenzoate and 30 ml of 15% aqueous sodium hydroxide solution and the mixture obtained was stirred at room temperature for 2 hours. Then, the reaction mixture was added to hydrochloric acid for acidification. Crystals precipitated were collected by filtration and dried to obtain 8.0 g of 4-(2-propynyloxy)-3-fluorobenzoic acid represented by the formula:

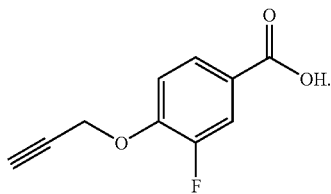

4-(2-Propynyloxy)-3-fluorobenzoic acid $^1$H-NMR (DMSO-d$_6$) δ: 3.21-3.59 (1H, m), 3.68 (1H, t, J=2.3 Hz), 5.01 (2H, d, J=2.2 Hz), 7.34 (1H, t, J=8.5 Hz), 7.71 (1H, dd, J=11.8, 1.9 Hz), 7.77-7.83 (1H, m)

REFERENCE PRODUCTION EXAMPLE 4

(a) To 50 ml of N-methylpyrrolidone were added 10 g of 3,4,5-trifluorobromobenzene and 8.5 g of copper cyanide, and the mixture obtained was stirred at 150° C. for 4 hours.

Then, aqueous ammonia was added to the reaction mixture and the mixture was extracted with ethyl acetate. The organic layer was dried over magnesium sulfate and concentrated under reduced pressure. The residue was subjected to silica gel column chromatography to obtain 5.0 g of 3,4,5-trifluorobenzonitrile.

To a solution of 5.0 g of 3,4,5-trifluorobenzonitrile and 4.5 g of benzyl alcohol in 25 ml of DMF was added 1.5 g of 60% sodium hydride (oily) at 0° C. The mixture was stirred at room temperature for 4 hours. Then, dilute hydrochloric acid was added to the reaction mixture and the mixture was extracted with ethyl acetate. The organic layer was dried over magnesium sulfate and concentrated under reduced pressure. The residue was subjected to silica gel column chromatography to obtain 7.0 g of 4-benzyloxy-3,5-difluorobenzonitrile represented by the formula:

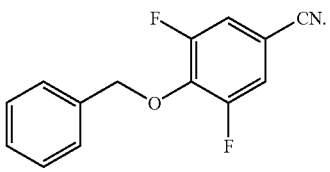

4-Benzyloxy-3,5-difluorobenzonitrile $^1$H-NMR (CDCl$_3$) δ: 5.29 (2H, s), 7.14-7.23 (2H, m), 7.29-7.43 (5H, m).

4-Benzyloxy-3,5-difluorobenzonitrile and 15 ml of concentrated sulfuric acid were added to 100 ml of methanol and the mixture was heated under reflux for 5 days. Then, water was added to the reaction mixture and the mixture was extracted with ethyl acetate. The organic layer was dried over magnesium sulfate and concentrated under reduced pressure. The residue was subjected to silica gel column chromatography to obtain 4.5 g of methyl 3,5-difluoro-4-hydroxybenzoate represented by the formula:

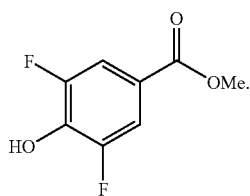

Methyl 3,5-difluoro-4-hydroxybenzoate $^1$H-NMR (CDCl$_3$) δ: 3.91 (3H, s), 6.00 (1H, br s), 7.58-7.67 (2H, m)

To 80 ml of acetonitrile were added 4.5 g of methyl 3,5-difluoro-4-hydroxybenzoate, 3.5 g of propargyl bromide and 9.4 g of cesium carbonate, and the mixture obtained was heated under reflux for 2 hours. The reaction mixture was filtered through Celite. The filtrate was concentrated under reduced pressure. The residue was subjected to silica gel column chromatography to obtain 5.5 g of methyl 3,5-difluoro-4-(2-propynyloxy)benzoate represented by the formula:

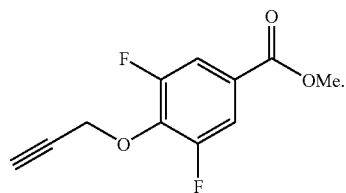

Methyl 3,5-difluoro-4-(2-propynyloxy)benzoate $^1$H-NMR (CDCl$_3$) δ: 2.53 (1H, t, J=2.4 Hz), 3.92 (3H, s), 4.91 (2H, d, J=2.4 Hz), 7.61 (2H, ddd, J=15.1, 7.5, 2.2 Hz).

To 30 ml of ethanol were added 5.5 g of methyl 3,5-difluoro-4-(2-propynyloxy)benzoate and 10 ml of 15% aqueous sodium hydroxide solution and the mixture obtained was stirred at room temperature for 2 hours. Then, the reaction mixture was concentrated under reduced pressure. Hydrochloric acid was added to the residue for acidification and then, solid precipitated was collected by filtration to obtain 5.0 g of 3,5-difluoro-4-(2-propynyloxy)benzoic acid represented by the formula:

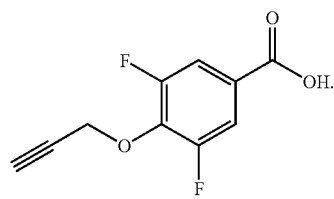

3,5-Difluoro-4-(2-propynyloxy)benzoic acid $^1$H-NMR (CDCl$_3$) δ: 2.54 (1H, t, J=2.2 Hz), 4.94 (2H, d, J=2.2 Hz), 7.65-7.72 (2H, m).

(b) To 50 ml of acetonitrile were added 12 g of propargyl alcohol, 16 g of 3,4,5-trifluorobenzaldehyde and 15 g of potassium carbonate, and the mixture obtained was stirred at room temperature for 1 day. Then, water was added to the reaction mixture and the mixture was extracted with ethyl acetate. The organic layer was washed with dilute hydrochloric acid and brine. The organic layer was dried over magnesium sulfate and concentrated under reduced pressure. The residue was subjected to silica gel column chromatography to obtain 20 g of 3,5-difluoro-4-(2-propynyloxy)benzaldehyde represented by the formula:

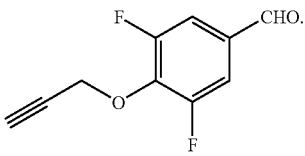

3,5-Difluoro-4-(2-propynyloxy)benzaldehyde $^1$H-NMR (CDCl$_3$) δ: 2.55 (1H, t, J=2.4 Hz), 4.96 (2H, d, J=2.4 Hz), 7.44-7.52 (2H, m), 9.87 (1H, t, J=1.8 Hz).

To 100 ml of chloroform were added 20 g of 3,5-difluoro-4-(2-propynyloxy)benzaldehyde and 25 g of 3-chloroperbenzoic acid and the mixture obtained was stirred at room temperature for overnight. Then, aqueous sodium sulfite solution was added to the reaction mixture and extracted with chloroform and ethyl acetate in order. The organic layers were combined, dried over magnesium sulfate and concentrated under reduced pressure to obtain 40 g of 3,5-difluoro-4-(2-propynyloxy)benzoic acid.

(c) To 50 ml of DMF were added 5.0 g of 3,4,5-trifluorobenzoic acid, 4.0 g of propargyl bromide and 4.7 g of potassium carbonate and the mixture obtained was stirred at room temperature for 30 minutes and then heated with stirring at 80° C. for 1 hour. Then, ethyl acetate was added to the reaction mixture and the mixture was filtered through Celite. Water and dilute hydrochloric acid were added to the filtrate in order and it was extracted with ethyl acetate. The organic layer was dried over magnesium sulfate and concentrated under reduced pressure to obtain 6.0 g of 2-propynyl 3,4,5-trifluorobenzoate represented by the formula:

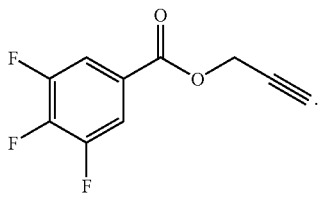

2-Propynyl 3,4,5-trifluorobenzoate $^1$H-NMR (CDCl$_3$) δ: 2.55 (1H, t, J=2.4 Hz), 4.93 (2H, d, J=2.4 Hz), 7.68-7.76 (2H, m).

To a solution of 5.0 g of 2-propynyl 3,4,5-trifluorobenzoate and 1.7 g of propargyl alcohol in 20 ml of DMF was added 1.1 g of 60% sodium hydride (oily) at 0° C. The mixture was stirred at 0° C. for 30 minutes and at room temperature for 1 hour. Then, water was added to the reaction mixture and the mixture was extracted with ethyl acetate. The organic layer was dried over magnesium sulfate and concentrated under reduced pressure. The residue was subjected to silica gel column chromatography to obtain 2.9 g of 2-propynyl 3,5-difluoro-4-(2-propynyloxy)benzoate represented by the formula:

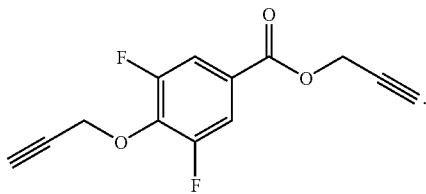

2-Propynyl 3,5-difluoro-4-(2-propynyloxy)benzoate $^1$H-NMR (CDCl$_3$) δ: 2.52 (1H, t, J=2.4 Hz), 2.54 (1H, t, J=2.4 Hz), 4.91 (2H, d, J=2.7 Hz), 4.92 (2H, d, J=2.7 Hz), 7.62-7.68 (2H, m).

To 10 ml of ethanol were added 2.2 g of 2-propynyl 3,5-difluoro-4-(2-propynyloxy)benzoate and 6 ml of 15% aqueous sodium hydroxide solution, and the mixture obtained was stirred at 50° C. for 1 hour. Then, the reaction mixture was concentrated under reduced pressure. Hydrochloric acid was added to the residue for acidification. Crystals precipitated were collected by filtration and dried to obtain 1.8 g of 3,5-difluoro-4-(2-propynyloxy)benzoic acid.

To 17 ml of toluene were added 1.8 g of 3,5-difluoro-4-(2-propynyloxy)benzoic acid, 1 ml of thionyl chloride and 10 mg of DMF and the mixture was heated under reflux for 4 hours. Then, the reaction mixture was concentrated under reduced pressure to obtain 1.9 g of 3,5-difluoro-4-(2-propynyloxy) benzoyl chloride represented by the formula:

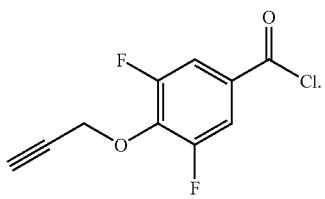

3,5-Difluoro-4-(2-propynyloxy)benzoyl chloride $^1$H-NMR (CDCl$_3$) δ: 2.55 (1H, t, J=2.4 Hz), 4.98 (2H, d, J=2.4 Hz), 7.69-7.76 (2H, m).

REFERENCE PRODUCTION EXAMPLE 5

To 40 ml of acetonitrile were added 7.3 g of 3-fluoro-4-hydroxy-5-methoxybenzaldehyde, 8.8 g of benzyl bromide, 16.8 g of cesium carbonate and 10 ml of DMF, and the mixture obtained was heated under reflux for 10 hours. The reaction mixture was concentrated under reduced pressure. Hydrochloric acid was added to the residue and extracted with ethyl acetate. The organic layer was dried over magnesium sulfate and concentrated under reduced pressure. The residue was subjected to silica gel column chromatography to obtain 7.5 g of 4-benzyloxy-3-fluoro-5-methoxybenzaldehyde represented by the formula:

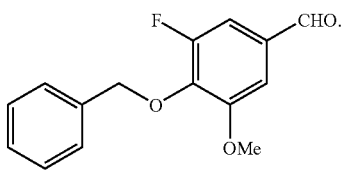

A solution of 7.5 g of 4-benzyloxy-3-fluoro-5-methoxybenzaldehyde in 200 ml of acetone was added dropwise at 15 to 20° C. to a mixture of 200 ml of water and 6.8 g of potassium permanganate. The mixture was stirred at room temperature for 3 days. The reaction mixture was concentrated to about a half amount under reduced pressure. Aqueous sodium hydrogen sulfite solution and dilute hydrochloric acid were added to the concentrate and extracted twice with ethyl acetate. The organic layer was dried over magnesium sulfate and concentrated under reduced pressure to obtain 4-benzyloxy-3-fluoro-5-methoxybenzoic acid.

To 4-benzyloxy-3-fluoro-5-methoxybenzoic acid were added 20 ml of methanol, 20 ml of ethyl acetate and 50 mg of 10% palladium-carbon and the mixture was stirred at room temperature for 4 hours under hydrogen atmosphere. Then, the reaction mixture was filtered through Celite. The filtrate was concentrated under reduced pressure to obtain 4.5 g of 3-fluoro-4-hydroxy-5-methoxybenzoic acid represented by the formula:

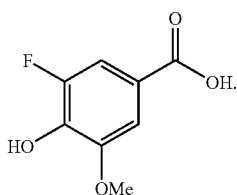

3-Fluoro-4-hydroxy-5-methoxybenzoic acid $^1$H-NMR (DMSO-d$_6$) δ: 3.87 (3H, s), 7.32-7.36 (2H, m)

To 80 ml of DMF were added 4.5 g of 3-fluoro-4-hydroxy-5-methoxybenzoic acid, 7.0 g of propargyl bromide and 9.1 g of potassium carbonate, and the mixture obtained was stirred at room temperature for 2 days. Then, hydrochloric acid was added to the reaction mixture and the mixture was extracted with ethyl acetate. The organic layer was dried over magnesium sulfate and concentrated under reduced pressure. The residue was subjected to silica gel column chromatography to obtain 4.5 g of 2-propynyl 3-fluoro-5-methoxy-4-(2-propynyloxy)benzoate represented by the formula:

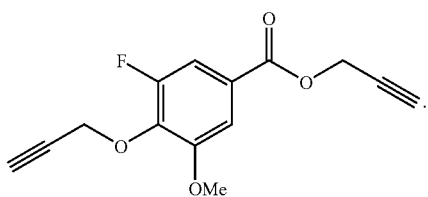

2-Propynyl 3-fluoro-5-methoxy-4-(2-propynyloxy)benzoate $^1$H-NMR (CDCl$_3$) δ: 2.49 (1H, t, J=2.4 Hz), 2.54 (1H, t, J=2.4 Hz), 3.94 (3H, s), 4.87 (2H, d, J=2.4 Hz), 4.91 (2H, d, J=2.4 Hz), 7.43 (1H, dd, J=1.8, 1.8 Hz), 7.48 (1H, dd, J=10.4, 1.8 Hz).

To 40 ml of methanol were added 4.5 g of 2-propynyl 3-fluoro-5-methoxy-4-(2-propynyloxy)benzoate and 20 ml of 15% aqueous sodium hydroxide solution and the mixture obtained was stirred at room temperature for 8 hours. Then, the reaction mixture was concentrated. Hydrochloric acid was added to the residue for acidification. Solids precipitated were collected by filtration and dried to obtain 3.7 g of 3-fluoro-5-methoxy-4-(2-propynyloxy)benzoic acid represented by the formula:

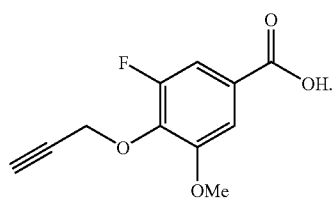

3-Fluoro-5-methoxy-4-(2-propynyloxy)benzoic acid $^1$H-NMR (CDCl$_3$) δ: 2.50 (1H, t, J=2.4 Hz), 3.95 (3H, s), 4.89 (2H, d, J=2.4 Hz), 7.46-7.57 (2H, m).

Then, Formulation Examples are shown. All the parts are parts by weight.

FORMULATION EXAMPLE 1

A wettable powder for each compound of the present invention is obtained by thoroughly pulverizing and mixing 50 parts of each of the compounds 1 to 70 of the present invention, 3 parts of calcium lignin sulfonate, 2 parts of magnesium lauryl sulfonate and 45 parts of synthetic hydrous silicon oxide.

FORMULATION EXAMPLE 2

After mixing 20 parts of each of the compounds 1 to 70 of the present invention and 1.5 parts of sorbitan trioleate with 28.5 parts of aqueous solution containing 2 parts of polyvinyl alcohol, the mixture is finely pulverized by a wet pulverization method. Then, 40 parts of aqueous solution containing 0.05 part of xanthan gum and 0.1 part of aluminum magnesium silicate are added thereto. Further, 10 parts of propylene glycol is added thereto and the mixture was mixed to obtain a flowable preparation for each compound of the present invention.

FORMULATION EXAMPLE 3

A dust for each compound of the present invention is obtained by thoroughly pulverizing and mixing 2 parts of each of the compounds 1 to 70 of the present invention, 88 parts of kaolin clay and 10 parts of talc.

FORMULATION EXAMPLE 4

An emulsion for each compound of the present invention is obtained by thoroughly mixing 5 parts of each of the compounds 1 to 70 of the present invention, 14 parts of polyoxyethylene styrylphenyl ether, 6 parts of calcium dodecylbenzene sulfonate and 75 parts of xylene.

FORMULATION EXAMPLE 5

A granule for each compound of the present invention is obtained by thoroughly pulverizing and mixing 2 parts of each of the compounds 1 to 70 of the present invention, 1 part of synthetic hydrous silicon oxide, 2 parts of calcium lignin sulfonate, 30 parts of bentonite and 65 parts of kaolin clay, adding water, thoroughly kneading the mixture, granulating and drying.

FORMULATION EXAMPLE 6

A flowable preparation for each compound of the present invention is obtained by mixing 10 parts of each of the compounds 1 to 70 of the present invention, 35 parts of white carbon containing 50 parts of ammonium polyoxyethylene alkyl ether sulfate and 55 parts of water and thoroughly pulverizing the mixture by a wet pulverization method.

Next, the following Test Examples will demonstrate that the compounds of the present invention are useful for controlling plant diseases.

In Test Examples, the controlling activity was evaluated by visually observing the areas of lesions on plants tested and comparing the area of the lesion of a plant treated with the compound of the present invention with the area of the lesion of a plant without the treatment.

TEST EXAMPLE 1

Sandy loam was packed in plastic pots and seeds of tomato (variety: Patio) were sowed and grown in a greenhouse for 20 days. A flowable preparation for each of the compounds 2, 3, 5, 6, 10, 11, 13, 15, 16, 17, 19, 21, 22, 23, 24, 25, 27, 28, 29, 31, 32, 34, 36, 37, 38 39, 43, 44, 46, 48, 49, 54, 55, 59, 63, 64, 65, 66, 68, 69, 74, 76, 80, 100, 103, 104, 105, 106, 108, 110, 115, 116 and 117 of the present invention was prepared according to Formulation Example 6, and then the preparation was diluted with water so that the concentration of the compound of the present invention was 500 ppm to prepare a test solution. The test solution was sprayed on the leaves and stems so that the solution thoroughly adhered to the leaf surfaces of the above-mentioned tomato seedling. After air-drying the test solution on the leaf surfaces, an aqueous suspension of zoosporangia of *Phytophthora infestans* (about 30,000/ml) was sprayed on the tomato seedling (at a proportion of about 2 ml per one seedling). The tomato seedling was cultivated under conditions of 23° C. and a relative humidity of 90% or more for one day, transferred to a greenhouse at 24° C. during daytime and 20° C. at night, and then cultivated for 4 days, followed by examining the lesion area of *Phytophthora infestans* of the tomato seedling.

The lesion areas in the seedlings treated with the compounds 2, 3, 5, 6, 10, 11, 13, 15, 16, 17, 19, 21, 22, 23, 24, 25, 27, 28, 29, 31, 32, 33, 34, 36, 37, 38 39, 43, 44, 46, 48, 49, 54, 55, 59, 63, 64, 65, 66, 68, 69, 74, 76, 80, 100, 103, 104, 105, 106, 108, 110, 115, 116 and 117 of the present invention were 30% or less as compared with the lesion areas in seedlings without the treatment.

TEST EXAMPLE 2

Sandy loam was packed in plastic pots and the seeds of tomato (variety: Patio) were sowed and grown in a greenhouse for 20 days. A flowable preparation for each of the compounds 1, 2, 5, 6, 11, 13, 14, 15, 16, 17, 19, 21, 22, 23, 24, 25, 29, 30, 31, 32, 33, 34, 35, 36, 37, 38, 39, 43, 44, 46, 48, 49, 54, 55, 56, 59, 66, 68, 69, 70, 74, 89, 105, 106, 108, 109, 110, 111, 115, 116 and 117 of the present invention was prepared according to Formulation Example 6, and the preparation was diluted with water so that the concentration of the compound of the present invention was 200 ppm to prepare a test solution. The test solution was sprayed on the leaves and stems so that the test solution thoroughly adhered to the leaf surfaces of the above-mentioned tomato seedling. After air-drying the test solution on the leaf surfaces, an aqueous suspension of zoosporangia of *Phytophthora infestans* (about 30,000/ml) was sprayed on the tomato seedling (at a proportion of about 2 ml per one plant). The tomato seedling was cultivated under conditions of 23° C. and a relative humidity of 90% or more for one day, transferred to a greenhouse at 24° C. during daytime and 20° C. at night, and cultivated for 4 days, followed by examining the lesion area of *Phytophthora infestans* in the tomato seedling.

The lesion areas in the seedlings treated with the compounds 1, 2, 5, 6, 11, 13, 14, 15, 16, 17, 19, 21, 22, 23, 24, 25, 29, 30, 31, 32, 33, 34, 35, 36, 37, 38, 39, 43, 44, 46, 48, 49, 54, 55, 56, 59, 66, 68, 69, 70, 74, 89, 105, 106, 108, 109, 110, 111, 115, 116 and 117 of the present invention were 30% or less as compared with the lesion areas in seedlings without treatment.

TEST EXAMPLE 3

Sandy loam was packed in plastic pots with a volume of 160 ml and seeds of tomato (variety: Patio) were sowed and grown in a greenhouse for 13 days. A flowable preparation for each of the compounds 1, 2, 6, 16, 17, 21, 22, 23, 24, 26, 27, 28, 30, 34, 39, 42, 48, 54, 55, 56, 64, 68, 69, 70, 75, 81, 87, 89, 95, 101, 102, 103, 104, 108, 111, 112, 115, 116 and 117 of the present invention was prepared according to Formulation Example 6, and the preparation was diluted with water so that the concentration of the compound of the present invention was 200 ppm to prepare a test solution. The test solution was applied to the plant bottom of the above-mentioned tomato seedling by irrigation treatment at a rate of 20 ml per one pot. The tomato seedling was transferred to a greenhouse at 24° C. during daytime and 20° C. at night and cultivated for 7 days. Then, an aqueous suspension of zoosporangia of *Phytophthora infestans* (about 30,000/ml) was sprayed on the tomato seedling (at a proportion of about 2 ml per one plant). The tomato seedling was cultivated under conditions of 23° C. and a relative humidity of 90% or more for one day, transferred to a greenhouse at 24° C. during daytime and 20° C. at night and cultivated for 4 days, followed by examining the lesion area of *Phytophthora infestans* of the tomato seedling.

The lesion areas in the seedlings treated with the compounds 1, 2, 6, 16, 17, 21, 22, 23, 24, 26, 27, 28, 30, 34, 39, 42, 48, 54, 55, 56, 64, 68, 69, 70, 75, 81, 87, 89, 95, 101, 102, 103, 104, 108, 111, 112, 115, 116 and 117 of the present invention were 30% or less as compared with the lesion areas in seedlings without treatment.

INDUSTRIAL APPLICABILITY

Since the compound of the present invention is very effective for controlling plant diseases, it is useful as an effective ingredient of a composition for controlling plant diseases.

The invention claimed is:

1. An amide compound represented by the formula (1)

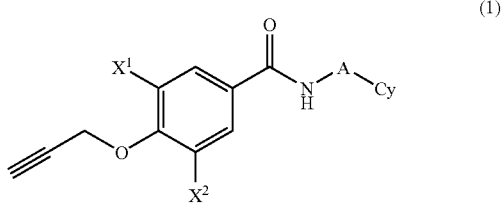

(1)

wherein $X^1$ represents a fluorine atom or a methoxy group,
$X^2$ represents a hydrogen atom, a fluorine atom or a methoxy group,
Z represents an oxygen atom or a sulfur atom,
A represents a single bond or a $CH_2$ group, a $CH(CH_3)$ group, a $C(CH_3)_2$ group or a $CH(CH_2CH_3)$ group,
Cy represents a C3 to C6 cycloalkyl group optionally substituted with at least one group selected from the group consisting of a C1 to C4 alkyl group, a C2 to C4 alkenyl group, a C2 to C4 alkynyl group, a halogen atom, a hydroxyl group, a cyano group, a carboxyl group, or a (C1 to C3 alkoxy)carbonyl group.

2. The amide compound according to claim 1, wherein, in the formula (1), Z is an oxygen atom.

3. The amide compound according to claim 1, wherein, in the formula (1), $X^1$ is a fluorine atom and $X^2$ is a hydrogen atom; or $X^1$ is a fluorine atom and $X^2$ is a fluorine atom; $X^1$ is a methoxy group and $X^2$ is a hydrogen atom; or $X^1$ is a methoxy group and X is a methoxy group.

4. The amide compound according to claim 1, wherein, in the formula (1), $X^1$ is a methoxy group and $X^2$ is a methoxy group.

5. The amide compound according to claim 1, wherein, in the formula (1), $X^1$ is a methoxy group and $X^2$ is a hydrogen atom.

6. The amide compound according to claim 1, wherein, in the formula (1), A is a single bond, a $CH_2$ group or a $CH(CH_3)$ group and Cy is a C3 to C6 cycloalkyl group optionally substituted with a C1 to C4 alkyl group.

7. The amide compound according to claim 1, wherein, in the formula (1), A is a single bond, a $CH_2$ group or a $CH(CH_3)$ group and Cy is a cyclohexyl group optionally substituted with a C1 to C4 alkyl group.

8. The amide compound according to claim 1, wherein, in the formula (1), A is a single bond, a $CH_2$ group or a $CH(CH_3)$ group and Cy is a cyclohexyl group optionally substituted with a methyl group.

9. The amide compound according to claim 1, wherein in the formula (1), $X^1$ is a fluorine atom and $X^2$ is a fluorine atom.

10. A composition for controlling plant diseases which comprises the amide compound according to claim 1 as an effective ingredient and an inactive carrier.

11. The amide compound according to claim 2, wherein, in the formula (1), $X^1$ is a fluorine atom and $X^2$ is a hydrogen atom; or $X^1$ is a fluorine atom and $X^2$ is a fluorine atom; $X^1$ is a methoxy group and $X^2$ is a hydrogen atom; or $X^1$ is a methoxy group and $X^2$ is a methoxy group.

12. The amide compound according to claim 2, wherein, in the formula (1), $X^1$ is a methoxy group and $X^2$ is a methoxy group.

13. The amide compound according to claim 2, wherein, in the formula (1), $X^1$ is a methoxy group and $X^2$ is a hydrogen atom.

14. The amide compound according to claim 2, wherein, in the formula (1), A is a single bond, a $CH_2$ group or a $CH(CH_3)$ group and Cy is a cyclohexyl group optionally substituted with a methyl group.

15. The amide compound according to claim 3, wherein, in the formula (1), A is a single bond, a $CH_2$ group or a $CH(CH_3)$ group and Cy is a cyclohexyl group optionally substituted with a methyl group.

16. The amide compound according to claim 4, wherein, in the formula (1), A is a single bond, a $CH_2$ group or a $CH(CH_3)$ group and Cy is a cyclohexyl group optionally substituted with a methyl group.

17. The amide compound according to claim 5, wherein, in the formula (1), A is a single bond, a $CH_2$ group or a $CH(CH_3)$ group and Cy is a cyclohexyl group optionally substituted with a methyl group.

* * * * *